United States Patent
Gilula et al.

(10) Patent No.: US 6,271,015 B1
(45) Date of Patent: *Aug. 7, 2001

(54) FATTY-ACID AMIDE HYDROLASE

(75) Inventors: Norton B. Gilula, La Jolla; Benjamin F. Cravatt, San Diego; Richard A. Lerner, La Jolla, all of CA (US)

(73) Assignee: The Scripps Research Institute, La Jolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/743,168

(22) Filed: Nov. 4, 1996

Related U.S. Application Data

(63) Continuation-in-part of application No. 08/489,535, filed on Jun. 12, 1995, now abandoned.

(51) Int. Cl.$^7$ ..................................................... C12N 9/80

(52) U.S. Cl. ........................................ 435/228; 435/227

(58) Field of Search .................................. 435/227, 228, 435/134, 129, 7.71; 532/62; 536/91.9

(56) References Cited

U.S. PATENT DOCUMENTS 4,165,258    8/1979   Pye et al. .

OTHER PUBLICATIONS

Mayaux et al., Journal of Bacteriology, Dec. 1990, vol. 172, No. 12, pp. 6764–6773.*
Cravatt et al., Science, Jun. 09, 1995, pp. 1506–1509.*
Maurelli et al., Federation of European Biochemical Societies Letters. 1995. vol. 377, pp. 82–86.*
Ohkawa et al., Journal of Antibacterial, Antifungal Agents, 1990, vol. 18, No. 8, p. 371374.*
Scopes, R.K. Protein Purification. New York: Springer Verlag. 1987, pp. 100–114.*
Koutek et al., Journal of Biological Chemistry, Sep. 16, 1994, vol. 269, No. 37, pp. 2293–2940.*
Matsuzaki, et al., "Paradoxical Phase of Sleep: Its Artificial Induction in the Cat by Sodium Butyrate", *Science 146*: 1328–1329 (1964).
Pappenheimer, et al., "Sleep–Promoting Effects of Cerebrospinal Fluid From Sleep–Deprived Goats", *Proc. Natl. Acad. Sci. USA 58*: 513–517 (1967).
Yanagisawa, et al., "A Bromine Compound Isolated from Human Cerebrospinal Fluid", *Biochim. Biophys. Acta. 329*: 283–294 (1973).
Sallanon, et al., "Restoration of Paradoxical Sleep by Cerebrospinal Fluid Transfer to PCPA Pretreated Insomniac Cats", *Brain Res. 251*: 137–147 (1982).
Dewasmes, et al., "Sleep Changes in Long–Term Fasting Geese in Relation to Lipid and Protein Metabolism", *Amer. J. Physiol. 247*: R663–R671 (1984).
Prospéro–Garcia, et al., "Vasoactive Intestinal Polypeptide (VIP) and cerebrospinal fluid (CSF) of Sleep–Deprived Cats Restores REM Sleep in Insomniac Recipients", *Brain Res. 385*: 169–173 (1986).
Abeles, et al., "Enzyme Inhibitors: Ground–State/Transition–State Analogs", *Drug Development Research 10*: 221–234 (1987).
Fagioli, et al., "Decrease of Slow–Wave Sleep in Children with Prolonged Absence of Essential Lipids Intake", *Sleep 12*: 495–499 (1989).
Arafat, et al., "Identification of Fatty Acid Amides in Human Plasma", *Life Sciences 45*: 1679–1687 (1989).
Wakamatsu, et al., "Isolation of Fatty Acid Amide as an Angiogenic Principle from Bovine Mesentery", *Biochem. Biophys. Res. Commun. 168*: 423–429 (1990).
Ohkawa, et al., "Microbial Degradation of Fatty Acid Diethanolamide", *J. Antibact. Antifung. Agents 18*: 371–374 (1990).
Mayaux, et al., "Purification, Cloning, and Primary Structure of an Enantiomer–Selective Amidase from *Brevibacterium* sp. Strain R312: Structural Evidence for Genetic Coupling with Nitrile Hydratase", *J. Bacteriology 172*: 6764–6773 (1990).
Jain, et al., "Fatty Acid Amides: Scooting Mode–Based Discovery of Tight–Binding Competitive Inhibitors of Secreted Phospholipases $A_2$", *J. Med. Chem. 35*: 3584–3586 (1992).
Deutsch, et al., "Enzymatic Synthesis and Degradation of Anandamide, A Cannabinoid Receptor Agonist", *Biochem. Pharmacol. 46*: 791–796 (1993).
Childers, et al., "Effects of Anandamide on Cannabinoid Receptors in Rat Brain Membranes", *Biochem. Pharmacol. 47*: 711–715 (1994).
Koutek, et al., "Inhibitors of Arachidonoyl Ethanolamide Hdyrolysis", *J. Biol. Chem. 269*: 22937–22940 (1994).

(List continued on next page.)

*Primary Examiner*—Irene Marx
(74) *Attorney, Agent, or Firm*—Thomas E. Northrup; Thomas Fitting; Emily Holmes

(57) ABSTRACT

The soporific activity of cis-9,10-octadecenoamide and other soporific fatty acid primary(amides is neutralized by hydrolysis in the presence of fatty-acid amide hydrolase (FAAH). Hydrolysis of cis-9,10-octadecenoamide by FAAH leads to the formation of oleic acid, a compound without soporific activity. FAAH has be isolated and the gene encoding FAAH has been cloned, sequenced, and used to express recombinant FAAH. Inhibitors of FAAH are disclosed to block the hydrolase activity.

6 Claims, 26 Drawing Sheets

OTHER PUBLICATIONS

Cravatt, et al., "Chemical Characterization of a Family of Brain Lipids that Induce Sleep", *Science 268*: 1506–1509 (1995).

Ueda, et al., "Partial Purification and Characterization of the Porcine Brain Enzyme Hydrolyzing and Synthesizing Anandamide", *J. Biol. Chem. 270*: 23823–23827 (1995).

Maurelli, et al., "Two Novel Classes of Neuroactive Fatty Acid Amides are Substrates for Mouse Neuroblastoma 'Anandamide Amidohydrolase'", *FEBS Letters 377*: 82–86 (1995).

Patterson, et al., "Inhibition of Oleamide Hydrolase Catalyzed Hydrolysis of the Endogenous Sleep–Inducing Lipid cis–9–Octadecenamide", *J. Am. Chem. Soc. 118*: 5938–5945 (1996).

Rosell, et al., "New Trifluoromethyl Ketones as Potent Inhibitors of Esterases: $^{19}$F NMR Spectroscopy of Transition State Analog Complexes and Structure–Activity Relationships", *Biochem. Biophys. Res. Commun. 226*: 287–292 (1996).

\* cited by examiner

SPGGSSGGEGALIGSGGSPLGLGTDIGGSIRFPSAFC
GICGLKPTGNRLSKSGLKGCVYGQTAVQLSLGPMARD
VESLALCLKALLCEHLFTLDPTVPPFPFREEVYRSSR
PLRVGYYETDNYTMPSPAMRRALIETKQRLEAAGHTL
IPFLPNNIPYALEVLSAGGLFSDGGRSFLQNFKGDFV
DPCLGDLILILRLPSWFKRLLSLLLKPLFPRLAAFLN
SMRPRSAEKLWKLQHEIEMYRQSVIAQWKAMNLDVLL
TPMLGPALDLNTPGR

FIG. 2

Rat Liver

1) Sucrose gradient of liver membrane 2) 100 mM $Na_2CO_3$ wash

3) Solublization in Triton-based buffer

Liver Plasma Membrane

1) DEAE column (ion exchange)

2) Hg column

3) Heparin column (detergent xchng)

4) Affinity column with trifluoroketone inhibitor

Amidase activity 20-30 fold enriched, 10-15% yield

Assay used: $^{14}C$ radiolabeled substrate and TLC analysis

FIG. 3

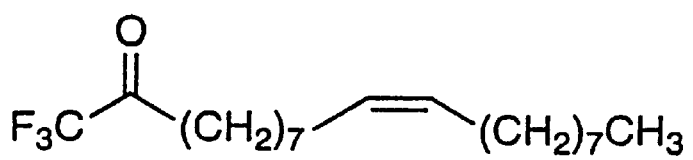
Trifluoroketone Inhibitor: $K_i$ = 1 nM
---
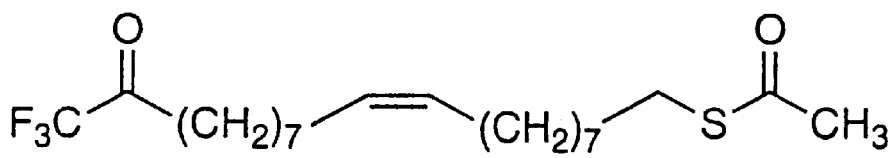
base deprotection of thioacetate, and immediate linkage | Link to disulfide-derivatized solid support
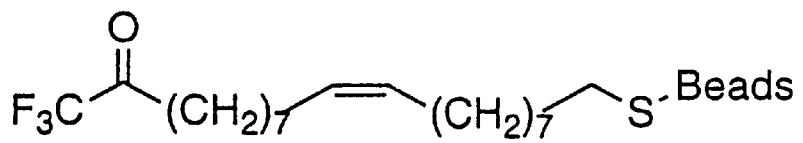
Advantage: thioacetate equivalent inhibitory potential to unmodified inhibitor, remove protein with reducing agent (20 mM DTT, 4° o/n)
FIG. 4

1-MVLSEVWTTLSGVSGVCLACSLLSAAVVLRWTGRQKARGAATRARQKQRA

51-SLETMDKAVQRFRLQNPDLDSEALLTLPLLQLVQKLQSGELSPEAVFFTY

101-LGKAWEVNKGTNCVTSYLTDCETQLSQAPRQGLLYGVPVSLKECFSYKGH

151-DSTLGLSLNEGMPSESDCVVVQVLKLQGAVPFVHTNVPQSMLSFDCSNPL

201-FGQTMNPWKSSKSPGGSSGGEGALIGSGGSPLGLGTDIGGSIRFPSAFCG

251-ICGLKPTGNRLSKSGLKGCVYGQTAVQLSLGPMARDVESLALCLKALLCE

301-HLFTLDPTVPPLPFREEVYRSSRPLRVGYYETDNYTMPSPAMRRALIETK

351-QRLEAAGHTLIPFLPNNIPYALEVLSAGGLFSDGGRSFLQNFKGDFVDPC

401-LGDLILILRLPSWFKRLLSLLLKPLFPRLAAFLNSMRPRSAEKLWKLQHE

451-IEMYRQSVIAQWKAMNLDVLLTPMLGPALDLNTPGRATGAISYTVLYNCL

501-DFPAGVVPVTTVTAEDDAQMELYKGYFGDIWDIILKKAMKNSVGLPVAVQ

551-CVALPWQEELCLRFMREVEQLMTPQKQPS-579

FIG. 9

```
              10              20              30              40
              *               *               *               *
    GGT TTG TGC GAG CCG AGT TCT CTC GGG TGG CGG TCG GCT GCA GGA GAT 50              60              70              80              90
     *               *               *               *               *
    CAT GGT GCT GAG CGA AGT GTG GAC CAC GCT GTC TGG GGT CTC CGG GGT
     M   V   L   S   E   V   W   T   T   L   S   G   V   S   G   V>

100             110             120             130             140
         *               *               *               *               *
    TTG CCT AGC CTG CAG CTT GTT GTC GGC GGC GGT GGT CCT GCG ATG GAC
     C   L   A   C   S   L   L   S   A   A   V   V   L   R   W   T>

150             160             170             180             190
         *               *               *               *               *
    CGG GCG CCA GAA GGC CCG GGG CGC GGC GAC CAG GGC GCG GCA GAA GCA
     G   R   Q   K   A   R   G   A   A   T   R   A   R   Q   K   Q>

200             210             220             230             240
         *               *               *               *               *
    GCG AGC CAG CCT GGA GAC CAT GGA CAA GGC GGT GCA GCG CTT CCG GCT
     R   A   S   L   E   T   M   D   K   A   V   Q   R   F   R   L>

250             260             270             280
         *               *               *               *
    GCA GAA TCC TGA CCT GGA CTC GGA GGC CTT GCT GAC CCT GCC CCT ACT
     Q   N   P   D   L   D   S   E   A   L   L   T   L   P   L   L>

290             300             310             320             330
     *               *               *               *               *
    CCA ACT GGT ACA GAA GTT ACA GAG TGG AGA GCT GTC CCC AGA GGC TGT
     Q   L   V   Q   K   L   Q   S   G   E   L   S   P   E   A   V>

340             350             360             370             380
     *               *               *               *               *
    GTT CTT TAC TTA CCT GGG AAA GGC CTG GGA AGT GAA CAA AGG GAC CAA
     F   F   T   Y   L   G   K   A   W   E   V   N   K   G   T   N>

390             400             410             420             430
         *               *               *               *               *
    CTG CGT GAC CTC CTA TCT GAC CGA CTG TGA GAC TCA GCT GTC CCA GGC
     C   V   T   S   Y   L   T   D   C   E   T   Q   L   S   Q   A>
```

FIG. 10-1

```
         440             450             460             470             480
          *               *               *               *               *
CCC ACG GCA GGG CCT GCT CTA TGG TGT CCC TGT GAG CCT CAA GGA ATG
 P   R   Q   G   L   L   Y   G   V   P   V   S   L   K   E   C>

490             500             510             520
              *               *               *               *
CTT CAG CTA CAA GGG CCA CGA CTC CAC ACT GGG CTT GAG CCT GAA TGA
 F   S   Y   K   G   H   D   S   T   L   G   L   S   L   N   E>

530             540             550             560             570
  *               *               *               *               *
GGG CAT GCC ATC GGA ATC TGA CTG TGT GGT GGT GCA AGT GTT GAA GCT
 G   M   P   S   E   S   D   C   V   V   V   Q   V   L   K   L>

580             590             600             610             620
  *               *               *               *               *
GCA GGG AGC TGT GCC CTT TGT GCA TAC CAA TGT CCC CCA GTC CAT GTT
 Q   G   A   V   P   F   V   H   T   N   V   P   Q   S   M   L>

630             640             650             660             670
              *               *               *               *               *
AAG CTT TGA CTG CAG TAA CCC TCT CTT TGG CCA GAC CAT GAA CCC ATG
 S   F   D   C   S   N   P   L   F   G   Q   T   M   N   P   W>

680             690             700             710             720
              *               *               *               *               *
GAA GTC CTC CAA GAG CCC AGG AGG TTC CTC AGG GGG TGA GGG GGC TCT
 K   S   S   K   S   P   G   G   S   S   G   G   E   G   A   L>

730             740             750             760
              *               *               *               *
CAT TGG ATC TGG AGG TTC CCC TCT GGG TTT AGG CAC TGA CAT TGG CGG
 I   G   S   G   G   S   P   L   G   L   G   T   D   I   G   G>

770             780             790             800             810
  *               *               *               *               *
CAG CAT CCG GTT CCC TTC TGC CTT CTG CGG CAT CTG TGG CCT CAA GCC
 S   I   R   F   P   S   A   F   C   G   I   C   G   L   K   P>

820             830             840             850             860
  *               *               *               *               *
TAC TGG CAA CCG CCT CAG CAA GAG TGG CCT GAA GGG CTG TGT CTA TGG
 T   G   N   R   L   S   K   S   G   L   K   G   C   V   Y   G>

870             880             890             900             910
  *               *               *               *               *
ACA GAC GGC AGT GCA GCT TTC TCT TGG CCC CAT GGC CGG GGA TGT GGA
 Q   T   A   V   Q   L   S   L   G   P   M   A   R   D   V   E>

920             930             940             950             960
  *               *               *               *               *
GAG CCT GGC GCT ATG CCT GAA AGC TCT ACT GTG TGA GCA CTT GTT CAC
 S   L   A   L   C   L   K   A   L   L   C   E   H   L   F   T>
```

FIG. 10-2

```
         970         980         990        1000
          *           *           *           *
CTT GGA CCC TAC CGT GCC TCC CTT GCC CTT CAG AGA GGA GGT CTA TAG
 L   D   P   T   V   P   P   L   P   F   R   E   E   V   Y   R>

1010        1020        1030        1040        1050
    *           *           *           *           *
AAG TTC TAG ACC CCT GCG TGT GGG GTA CTA TGA GAC TGA CAA CTA TAC
 S   S   R   P   L   R   V   G   Y   Y   E   T   D   N   Y   T>

1060        1070        1080        1090        1100
          *           *           *           *           *
CAT GCC CAG CCC AGC TAT GAG GAG GGC TCT GAT AGA GAC CAA GCA GAG
 M   P   S   P   A   M   R   R   A   L   I   E   T   K   Q   R>

1110        1120        1130        1140        1150
    *           *           *           *           *
ACT TGA GGC TGC TGG CCA CAC GCT GAT TCC CTT CTT ACC CAA CAA CAT
 L   E   A   A   G   H   T   L   I   P   F   L   P   N   N   I>

1160        1170        1180        1190        1200
          *           *           *           *           *
ACC CTA CGC CCT GGA GGT CCT GTC TGC GGG CGG CCT GTT CAG TGA CGG
 P   Y   A   L   E   V   L   S   A   G   L   F   S   D   G>

1210        1220        1230        1240
          *           *           *           *
TGG CCG CAG TTT TCT CCA AAA CTT CAA AGG TGA CTT TGT GGA TCC CTG
 G   R   S   F   L   Q   N   F   K   G   D   F   V   D   P   C>

1250        1260        1270        1280        1290
    *           *           *           *           *
CTT GGG AGA CCT GAT CTT AAT TCT GAG GCT GCC CAG CTG GTT TAA AAG
 L   G   D   L   I   L   I   L   R   L   P   S   W   F   K   R>

1300        1310        1320        1330        1340
    *           *           *           *           *
ACT GCT GAG CCT CCT GCT GAA GCC TCT GTT TCC TCG GCT GGC AGC TTT
 L   L   S   L   L   L   K   P   L   F   P   R   L   A   A   F>

1350        1360        1370        1380        1390
    *           *           *           *           *
TCT CAA CAG TAT GCG TCC TCG GTC AGC TGA AAA GCT GTG GAA ACT GCA
 L   N   S   M   R   P   R   S   A   E   K   L   W   K   L   Q>

1400        1410        1420        1430        1440
    *           *           *           *           *
GCA TGA GAT TGA GAT GTA TCG CCA GTC TGT GAT TGC CCA GTG GAA AGC
 H   E   I   E   M   Y   R   Q   S   V   I   A   Q   W   K   A>

1450        1460        1470        1480
          *           *           *           *
GAT GAA CTT GGA TGT GCT GCT GAC CCC CAT GTT GGG CCC TGC TCT GGA
 M   N   L   D   V   L   L   T   P   M   L   G   P   A   L   D>
```

FIG. 10-3

```
         10              20              30              40
          *               *               *               *
TGG GTC ATG GTG CTG AGC GAA GTG TGG ACC GCG CTG TCT GGA CTC TCC
ACC CAG TAC CAC GAC TCG CTT CAC ACC TGG CGC GAC AGA CCT GAG AGG
 W   V  [M]  V   L   S   E   V   W   T   A   L   S   G   L   S>

50              60              70              80              90
   *               *               *               *               *
GGG GTT TGC CTA GCC TGC AGC TTG CTG TCG GCG GCG GTG GTC CTG CGA
CCC CAA ACG GAT CGG ACG TCG AAC GAC AGC CGC CGC CAC CAG GAC GCT
 G   V   C   L   A   C   S   L   L   S   A   A   V   V   L   R>

100             110             120             130             140
     *               *               *               *               *
TGG ACC AGG AGC CAG ACC GCC CGG GGC GCG GTG ACC AGG GCG CGG CAG
ACC TGG TCC TCG GTC TGG CGG GCC CCG CGC CAC TGG TCC CGC GCC GTC
 W   T   R   S   Q   T   A   R   G   A   V   T   R   A   R   Q>

150             160             170             180             190
      *               *               *               *               *
AAG CAG CGA GCC GGC CTG GAG ACC ATG GAC AAG GCG GTG CAG CGC TTC
TTC GTC GCT CGG CCG GAC CTC TGG TAC CTG TTC CGC CAC GTC GCG AAG
 K   Q   R   A   G   L   E   T   M   D   K   A   V   Q   R   F>

200             210             220             230             240
          *               *               *               *               *
CGG CTG CAG AAT CCT GAC CTG GAT TCA GAG GCC TTG CTG GCT CTG CCC
GCC GAC GTC TTA GGA CTG GAC CTA AGT CTC CGG AAC GAC CGA GAC GGG
 R   L   Q   N   P   D   L   D   S   E   A   L   L   A   L   P>

250             260             270             280
              *               *               *               *
CTG CTC CAA CTG GTA CAG AAG TTA CAG AGT GGG GAA CTG TCC CCA GAA
GAC GAG GTT GAC CAT GTC TTC AAT GTC TCA CCC CTT GAC AGG GGT CTT
 L   L   Q   L   V   Q   K   L   Q   S   G   E   L   S   P   E>

290             300             310             320             330
  *               *               *               *               *
GCT GTG CTC TTT ACC TAC CTG GGA AAG GCC TGG GAA GTG AAC AAA GGG
CGA CAC GAG AAA TGG ATG GAC CCT TTC CGG ACC CTT CAC TTG TTT CCC
 A   V   L   F   T   Y   L   G   K   A   W   E   V   N   K   G>

340             350             360             370             380
      *               *               *               *               *
ACC AAC TGT GTG ACC TCC TAT CTG ACT GAC TGT GAG ACT CAG CTG TCC
TGG TTG ACA CAC TGG AGG ATA GAC TGA CTG ACA CTC TGA GTC GAC AGG
 T   N   C   V   T   S   Y   L   T   D   C   E   T   Q   L   S>

390             400             410             420             430
          *               *               *               *               *
CAG GCC CCA CGG CAG GGC CTG CTC TAT GGC GTC CCC GTG AGC CTC AAG
GTC CGG GGT GCC GTC CCG GAC GAG ATA CCG CAG GGG CAC TCG GAG TTC
 Q   A   P   R   Q   G   L   L   Y   G   V   P   V   S   L   K>

440             450             460             470             480
              *               *               *               *               *
GAA TGC TTC AGC TAC AAG GGC CAT GCT TCC ACA CTG GGC TTA AGT TTG
CTT ACG AAG TCG ATG TTC CCG GTA CGA AGG TGT GAC CCG AAT TCA AAC
 E   C   F   S   Y   K   G   H   A   S   T   L   G   L   S   L>
```

FIG. 13-1

```
      2070          2080          2090          2100          2110
        *             *             *             *             *
TCT GGG TAT CTC CAT TAG GGC CCT GGG AAC CAG AGT GCT GGG AAG GCT 2120          2130          2140          2150          2160
        *             *             *             *             *
GTC CAG ACC CTC CAG AGC TGG CTG TAA CCA CAT CAC TCT CCT GCT CCA 2170          2180          2190          2200
        *             *             *             *
AAG CCT CCC TAG TTC TGT CAC CCA CAA GAT AGA CAC AGG GAC ATG TCC 2210          2220          2230          2240          2250
  *             *             *             *             *
TTG GCA CTT GAC TCC TGT CCT TCC TTT CTT ATT CAG ATT GAC CCC AGC 2260          2270          2280          2290          2300
        *             *             *             *             *
CTT GAT GGA CCC TGC CCC TGC ACT TCC TTC CTC AGT CCA CCT CTC TGC 2310          2320          2330          2340          2350
        *             *             *             *             *
CGA CAC GCC CTT TTT ATG GCT CCT CTA TTT GTT GTG GAG ACA AGG TTT 2360          2370          2380          2390          2400
        *             *             *             *             *
CTC TCA GTA GCC CTG GCT GTC CAG GAC CTC ACT CTG TAG ATG AGG CTG 2410          2420          2430          2440
        *             *             *             *
GCT TTC AAC TCA CAA GGC TGC CTG CCT GGG TGC TGG GAT TAA AGG CGT 2450          2460          2470
  *             *             *
ATG CCA CCA CAA AGA AAA AAA AAA
```

FIG. 10-5

| | |
|---|---|
| Oleamide Hydrolase (Rat) | 215-GGSSGGEGALIGSGGSPLGLGTDIGGSIRFPS-246 |
| Propionamidase (Chick) | 222-GGSSGGEGALIAGGGSLLGIGSDVAGSIRLPS-253 |
| Putative Amidase (C. elegans) | 212-GGSSGGEGALIGAGGSLIGIGTDVGGSVRIPC-243 |
| Putative Amidase (C. elegans) | 213-GGSSGGESALISADGSLLGIGGDVGGSIRIPC-244 |
| Putative Amidase (S. cervevisiae) | 207-GGSSGGEGSLIGAHGSLLGLGTDIGGSIRIPS-238 |
| Acetamidase (Aspergillus) | 202-GGSSGGEGAIVGIRGGVIGVGTDIGGSIDVPA-233 |
| Indoleacetamidase (Agrobacterium) | 147-GGSSGGVAAAVASRLMLGGIGTDTGASVRLPA-178 |
| Indoleacetamidase (Pseudomonas) | 144-GGSSGGVAAAVASGIVPLSVGTDTGGSIRIPA-175 |

FIG. 11

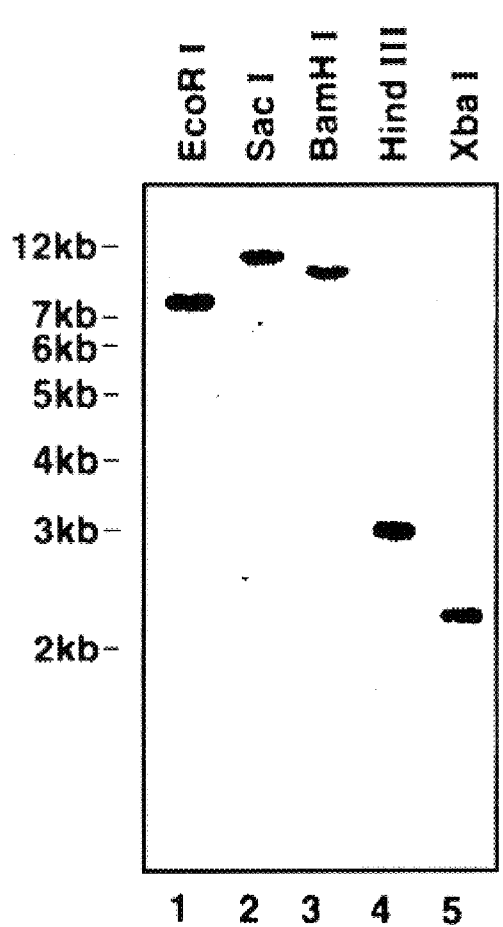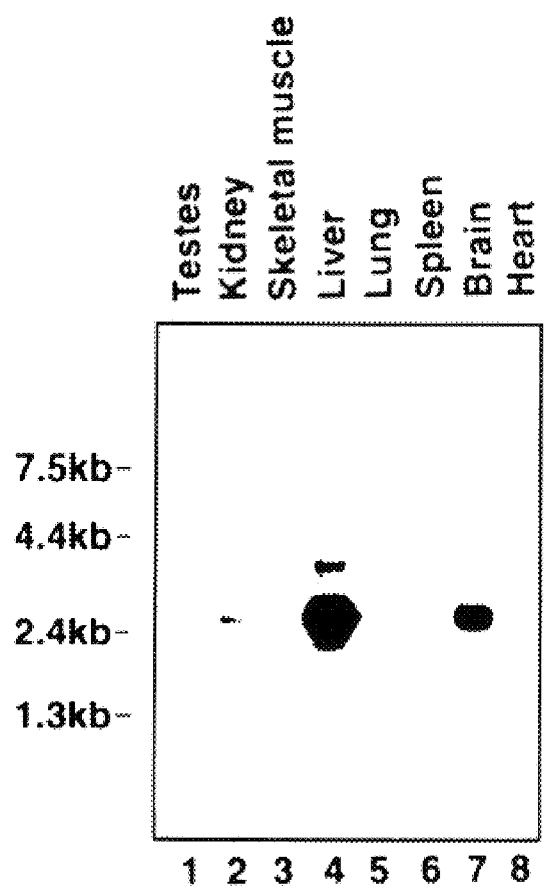
FIG. 12A
FIG. 12B

```
         10            20            30            40
          *             *             *             *
TGG GTC ATG GTG CTG AGC GAA GTG TGG ACC GCG CTG TCT GGA CTC TCC
ACC CAG TAC CAC GAC TCG CTT CAC ACC TGG CGC GAC AGA CCT GAG AGG
 W   V  [M]  V   L   S   E   V   W   T   A   L   S   G   L   S>

50            60            70            80            90
  *             *             *             *             *
GGG GTT TGC CTA GCC TGC AGC TTG CTG TCG GCG GCG GTG GTC CTG CGA
CCC CAA ACG GAT CGG ACG TCG AAC GAC AGC CGC CGC CAC CAG GAC GCT
 G   V   C   L   A   C   S   L   L   S   A   A   V   V   L   R>

100           110           120           130           140
  *             *             *             *             *
TGG ACC AGG AGC CAG ACC GCC CGG GGC GCG GTG ACC AGG GCG CGG CAG
ACC TGG TCC TCG GTC TGG CGG GCC CCG CGC CAC TGG TCC CGC GCC GTC
 W   T   R   S   Q   T   A   R   G   A   V   T   R   A   R   Q>

150           160           170           180           190
  *             *             *             *             *
AAG CAG CGA GCC GGC CTG GAG ACC ATG GAC AAG GCG GTG CAG CGC TTC
TTC GTC GCT CGG CCG GAC CTC TGG TAC CTG TTC CGC CAC GTC GCG AAG
 K   Q   R   A   G   L   E   T   M   D   K   A   V   Q   R   F>

200           210           220           230           240
  *             *             *             *             *
CGG CTG CAG AAT CCT GAC CTG GAT TCA GAG GCC TTG CTG GCT CTG CCC
GCC GAC GTC TTA GGA CTG GAC CTA AGT CTC CGG AAC GAC CGA GAC GGG
 R   L   Q   N   P   D   L   D   S   E   A   L   L   A   L   P>

250           260           270           280
  *             *             *             *
CTG CTC CAA CTG GTA CAG AAG TTA CAG AGT GGG GAA CTG TCC CCA GAA
GAC GAG GTT GAC CAT GTC TTC AAT GTC TCA CCC CTT GAC AGG GGT CTT
 L   L   Q   L   V   Q   K   L   Q   S   G   E   L   S   P   E>

290           300           310           320           330
  *             *             *             *             *
GCT GTG CTC TTT ACC TAC CTG GGA AAG GCC TGG GAA GTG AAC AAA GGG
CGA CAC GAG AAA TGG ATG GAC CCT TTC CGG ACC CTT CAC TTG TTT CCC
 A   V   L   F   T   Y   L   G   K   A   W   E   V   N   K   G>

340           350           360           370           380
  *             *             *             *             *
ACC AAC TGT GTG ACC TCC TAT CTG ACT GAC TGT GAG ACT CAG CTG TCC
TGG TTG ACA CAC TGG AGG ATA GAC TGA CTG ACA CTC TGA GTC GAC AGG
 T   N   C   V   T   S   Y   L   T   D   C   E   T   Q   L   S>

390           400           410           420           430
  *             *             *             *             *
CAG GCC CCA CGG CAG GGC CTG CTC TAT GGC GTC CCC GTG AGC CTC AAG
GTC CGG GGT GCC GTC CCG GAC GAG ATA CCG CAG GGG CAC TCG GAG TTC
 Q   A   P   R   Q   G   L   L   Y   G   V   P   V   S   L   K>

440           450           460           470           480
  *             *             *             *             *
GAA TGC TTC AGC TAC AAG GGC CAT GCT TCC ACA CTG GGC TTA AGT TTG
CTT ACG AAG TCG ATG TTC CCG GTA CGA AGG TGT GAC CCG AAT TCA AAC
 E   C   F   S   Y   K   G   H   A   S   T   L   G   L   S   L>
```

FIG. 13-1

```
                490             500             510             520
                 *               *               *               *
        AAC GAG GGT GTG ACA TCG GAG AGT GAC TGT GTG GTG GTG CAG GTA CTG
        TTG CTC CCA CAC TGT AGC CTC TCA CTG ACA CAC CAC CAC GTC CAT GAC
         N   E   G   V   T   S   E   S   D   C   V   V   V   Q   V   L>

530             540             550             560             570
     *               *               *               *               *
    AAG CTG CAG GGA GCT GTG CCC TTT GTG CAC ACC AAC GTC CCC CAG TCC
    TTC GAC GTC CCT CGA CAC GGG AAA CAC GTG TGG TTG CAG GGG GTC AGG
     K   L   Q   G   A   V   P   F   V   H   T   N   V   P   Q   S>

580             590             600             610             620
         *               *               *               *               *
        ATG CTA AGC TAT GAC TGC AGT AAC CCC CTC TTT GGC CAG ACC ATG AAC
        TAC GAT TCG ATA CTG ACG TCA TTG GGG GAG AAA CCG GTC TGG TAC TTG
         M   L   S   Y   D   C   S   N   P   L   F   G   Q   T   M   N>

630             640             650             660             670
             *               *               *               *               *
            CCG TGG AAG CCC TCC AAG AGT CCA GGA GGT TCC TCA GGG GGT GAG GGG
            GGC ACC TTC GGG AGG TTC TCA GGT CCT CCA AGG AGT CCC CCA CTC CCC
             P   W   K   P   S   K   S   P   G   G   S   S   G   G   E   G>

680             690             700             710             720
                 *               *               *               *               *
                GCT CTC ATT GGA TCT GGA GGC TCC CCT CTG GGT TTA GGC ACT GAC ATC
                CGA GAG TAA CCT AGA CCT CCG AGG GGA GAC CCA AAT CCG TGA CTG TAG
                 A   L   I   G   S   G   G   S   P   L   G   L   G   T   D   I>

730             740             750             760
                     *               *               *               *
                    GGC GGC AGC ATC CGG TTC CCT TCT GCC TTC TGT GGC ATC TGT GGC CTC
                    CCG CCG TCG TAG GCC AAG GGA AGA CGG AAG ACA CCG TAG ACA CCG GAG
                     G   G   S   I   R   F   P   S   A   F   C   G   I   C   G   L>

770             780             790             800             810
     *               *               *               *               *
    AAG CCT ACT GGG AAC CGC CTC AGC AAG AGT GGC CTG AAG AGC TGT GTT
    TTC GGA TGA CCC TTG GCG GAG TCG TTC TCA CCG GAC TTC TCG ACA CAA
     K   P   T   G   N   R   L   S   K   S   G   L   K   S   C   V>

820             830             840             850             860
         *               *               *               *               *
        TAT GGA CAG ACA GCA GTG CAG CTT TCT GTT GGC CCC ATG GCA CGG GAT
        ATA CCT GTC TGT CGT CAC GTC GAA AGA CAA CCG GGG TAC CGT GCC CTA
         Y   G   Q   T   A   V   Q   L   S   V   G   P   M   A   R   D>

870             880             890             900             910
             *               *               *               *               *
            GTG GAT AGC CTG GCA TTG TGC ATG AAA GCC CTA CTT TGT GAG GAT TTG
            CAC CTA TCG GAC CGT AAC ACG TAC TTT CGG GAT GAA ACA CTC CTA AAC
             V   D   S   L   A   L   C   M   K   A   L   L   C   E   D   L>

920             930             940             950             960
                 *               *               *               *               *
                TTC CGC TTG GAC TCC ACC ATC CCC CCC TTG CCC TTC AGG GAG GAG ATC
                AAG GCG AAC CTG AGG TGG TAG GGG GGG AAC GGG AAG TCC CTC CTC TAG
                 F   R   L   D   S   T   I   P   P   L   P   F   R   E   E   I>

```
TAC AGA AGT TCT CGA CCC CTT CGT GTG GGA TAC TAT GAA ACT GAC AAC
ATG TCT TCA AGA GCT GGG GAA GCA CAC CCT ATG ATA CTT TGA CTG TTG
 Y   R   S   S   R   P   L   R   V   G   Y   Y   E   T   D   N>

1010        1020        1030        1040        1050
     *           *           *           *           *
TAC ACC ATG CCC ACT CCA GCC ATG AGG AGG GCT GTG ATG GAG ACC AAG
ATG TGG TAC GGG TGA GGT CGG TAC TCC TCC CGA CAC TAC CTC TGG TTC
 Y   T   M   P   T   P   A   M   R   R   A   V   M   E   T   K>

1060        1070        1080        1090        1100
     *           *           *           *           *
CAG AGT CTC GAG GCT GCT GGC CAC ACG CTG GTC CCC TTC TTA CCA AAC
GTC TCA GAG CTC CGA CGA CCG GTG TGC GAC CAG GGG AAG AAT GGT TTG
 Q   S   L   E   A   A   G   H   T   L   V   P   F   L   P   N>

1110        1120        1130        1140        1150
     *           *           *           *           *
AAC ATA CCT TAT GCC CTG GAG GTC CTG TCG GCA GGT GGG CTG TTC AGT
TTG TAT GGA ATA CGG GAC CTC CAG GAC AGC CGT CCA CCC GAC AAG TCA
 N   I   P   Y   A   L   E   V   L   S   A   G   G   L   F   S>

1160        1170        1180        1190        1200
     *           *           *           *           *
GAT GGT GGC TGC TCT TTT CTC CAA AAC TTC AAA GGC GAC TTT GTG GAT
CTA CCA CCG ACG AGA AAA GAG GTT TTG AAG TTT CCG CTG AAA CAC CTA
 D   G   G   C   S   F   L   Q   N   F   K   G   D   F   V   D>

1210        1220        1230        1240
     *           *           *           *
CCC TGC TTG GGG GAC CTG GTC TTA GTG CTG AAG CTG CCC AGG TGG TTT
GGG ACG AAC CCC CTG GAC CAG AAT CAC GAC TTC GAC GGG TCC ACC AAA
 P   C   L   G   D   L   V   L   V   L   K   L   P   R   W   F>

1250        1260        1270        1280        1290
 *           *           *           *           *
AAA AAA CTG CTG AGC TTC CTG CTG AAG CCT CTG TTT CCT CGG CTG GCA
TTT TTT GAC GAC TCG AAG GAC GAC TTC GGA GAC AAA GGA GCC GAC CGT
 K   K   L   L   S   F   L   L   K   P   L   F   P   R   L   A>

1300        1310        1320        1330        1340
     *           *           *           *           *
GCC TTT CTC AAC AGT ATG TGT CCT CGG TCA GCC GAA AAG CTG TGG GAA
CGG AAA GAG TTG TCA TAC ACA GGA GCC AGT CGG CTT TTC GAC ACC CTT
 A   F   L   N   S   M   C   P   R   S   A   E   K   L   W   E>

1350        1360        1370        1380        1390
     *           *           *           *           *
CTG CAG CAT GAG ATT GAG ATG TAT CGC CAG TCC GTC ATT GCC CAG TGG
GAC GTC GTA CTC TAA CTC TAC ATA GCG GTC AGG CAG TAA CGG GTC ACC
 L   Q   H   E   I   E   M   Y   R   Q   S   V   I   A   Q   W>

1400        1410        1420        1430        1440
     *           *           *           *           *
AAG GCA ATG AAC TTG GAC GTG GTG CTA ACC CCC ATG CTG GGT CCT GCT
TTC CGT TAC TTG AAC CTG CAC CAC GAT TGG GGG TAC GAC CCA GGA CGA
 K   A   M   N   L   D   V   V   L   T   P   M   L   G   P   A>

1450        1460        1470        1480
     *           *           *           *
CTG GAT TTG AAC ACA CCG GGC AGA GCC ACA GGG GCT ATC AGC TAC ACT
GAC CTA AAC TTG TGT GGC CCG TCT CGG TGT CCC CGA TAG TCG ATG TGA
```

FIG. 13-3

```
          L   D   L   N   T   P   G   R   A   T   G   A   I   S   Y   T>
        1490        1500        1510        1520        1530
         *           *           *           *           *
        GTT CTC TAT AAC TGC CTG GAC TTC CCT GCG GGG GTG GTG CCT GTC ACC
        CAA GAG ATA TTG ACG GAC CTG AAG GGA CGC CCC CAC CAC GGA CAG TGG
         V   L   Y   N   C   L   D   F   P   A   G   V   V   P   V   T>

1540        1550        1560        1570        1580
              *           *           *           *           *
        ACT GTG ACC GCT GAG GAC GAT GCC CAG ATG GAA CAC TAC AAA GGC TAC
        TGA CAC TGG CGA CTC CTG CTA CGG GTC TAC CTT GTG ATG TTT CCG ATG
         T   V   T   A   E   D   D   A   Q   M   E   H   Y   K   G   Y>

1590        1600        1610        1620        1630
              *           *           *           *           *
        TTT GGG GAT ATG TGG GAC AAC ATT CTG AAG AAG GGC ATG AAA AAG GGT
        AAA CCC CTA TAC ACC CTG TTG TAA GAC TTC TTC CCG TAC TTT TTC CCA
         F   G   D   M   W   D   N   I   L   K   K   G   M   K   K   G>

1640        1650        1660        1670        1680
                 *           *           *           *           *
        ATA GGC CTG CCT GTG GCT GTG CAG TGC GTG GCT CTG CCC TGG CAG GAA
        TAT CCG GAC GGA CAC CGA CAC GTC ACG CAC CGA GAC GGG ACC GTC CTT
         I   G   L   P   V   A   V   Q   C   V   A   L   P   W   Q   E>

1690        1700        1710        1720
                    *           *           *           *
        GAG CTG TGT CTG CGG TTC ATG CGG GAG GTG GAA CGG CTG ATG ACC CCT
        CTC GAC ACA GAC GCC AAG TAC GCC CTC CAC CTT GCC GAC TAC TGG GGA
         E   L   C   L   R   F   M   R   E   V   E   R   L   M   T   P>

1730        1740        1750        1760        1770
         *           *           *           *           *
        GAA AAG CGG CCA TCT TGA GGG TCA TTC ATC TGC CCA GCT CTG GAG GAC
        CTT TTC GCC GGT AGA ACT CCC AGT AAG TAG ACG GGT CGA GAC CTC CTG
         E   K   R   P   S   [*]

1780        1790        1800        1810        1820
               *           *           *           *           *
        CTA AGG CCC ATG CGC TCT GCA CTG CAG CCC CAT CTA TTC AGG ATC CTG
        GAT TCC GGG TAC GCG AGA CGT GAC GTC GGG GTA GAT AAG TCC TAG GAC 1830        1840        1850        1860        1870
               *           *           *           *           *
        CCA CCC ATG AGG AGA TGC CCA GCA CGG GAA GAG GCA ACC ACC TGC CCT
        GGT GGG TAC TCC TCT ACG GGT CGT GCC CTT CTC CGT TGG TGG ACG GGA 1880        1890        1900        1910        1920
               *           *           *           *           *
        CCC CTG GAC TCC TAC AGA AAC CCA GGA CAT GCC CTC CAT AAC CAA GTC
        GGG GAC CTG AGG ATG TCT TTG GGT CCT GTA CGG GAG GTA TTG GTT CAG 1930        1940        1950
                  *           *           *
        TGG ACC AGC TCC CCC GGA ATT CCT GCA GCC CGG GGG ATC
        ACC TGG TCG AGG GGG CCT TAA GGA CGT CGG GCC CCC TAG
```

FIG. 13-4

```
          10           20           30           40           50
           *            *            *            *            *
TG  CCG GGC GGT AGG CAG CAG CAG GCT GAA GGG ATC ATG GTG CAG TAC GAG
AC  GGC CCG CCA TCC GTC GTC GTC CGA CTT CCC TAG TAC CAC GTC ATG CTC
     P   G   G   R   Q   Q   Q   A   E   G   I  [M]  V   Q   Y   E>

60           70           80           90
           *            *            *            *
CTG TGG GCC GCG CTG CCT GGC GCC TCC GGG GTC GCC CTG GCC TGC TGC
GAC ACC CGG CGC GAC GGA CCG CGG AGG CCC CAG CGG GAC CGG ACG ACG
 L   W   A   A   L   P   G   A   S   G   V   A   L   A   C   C>

100          110          120          130          140
  *            *            *            *            *
TTC GTG GCG GCG GCC GTG GCC CTG CGC TGG TCC GGG CGC CGG ACG GCG
AAG CAC CGC CGC CGG CAC CGG GAC GCG ACC AGG CCC GCG GCC TGC CGC
 F   V   A   A   A   V   A   L   R   W   S   G   R   R   T   A>

150          160          170          180          190
           *            *            *            *            *
CGG GGC GCG GTG GTC CGG GCG CGA CAG AAG CAG CGA GCG GGC CTG GAG
GCC CCG CGC CAC CAG GCC CGC GCT GTC TTC GTC GCT CGC CCG GAC CTC
 R   G   A   V   V   R   A   R   Q   K   Q   R   A   G   L   E>

200          210          220          230          240
           *            *            *            *            *
AAC ATG GAC AGG GCG GCG CAG CGC TTC CGG CTC CAG AAC CCA GAC CTG
TTG TAC CTG TCC CGC CGC GTC GCG AAG GCC GAG GTC TTG GGT CTG GAC
 N   M   D   R   A   A   Q   R   F   R   L   Q   N   P   D   L>

250          260          270          280          290
           *            *            *            *            *
GAC TCA GAG GCG CTG CTA GCC CTG CCC CTG CCT CAG CTG GTG CAG AAG
CTG AGT CTC CGC GAC GAT CGG GAC GGG GAC GGA GTC GAC CAC GTC TTC
 D   S   E   A   L   L   A   L   P   L   P   Q   L   V   Q   K>

300          310          320          330
           *            *            *            *
TTA CAC AGT AGA GAG CTG GCC CCT GAG GCC GTG CTC TTC ACC TAT GTG
AAT GTG TCA TCT CTC GAC CGG GGA CTC CGG CAC GAG AAG TGG ATA CAC
 L   H   S   R   E   L   A   P   E   A   V   L   F   T   Y   V>

340          350          360          370          380
  *            *            *            *            *
GGA AAG GCC TGG GAA GTG AAC AAA GGG ACC AAC TGT GTG ACC TCC TAT
CCT TTC CGG ACC CTT CAC TTG TTT CCC TGG TTG ACA CAC TGG AGG ATA
 G   K   A   W   E   V   N   K   G   T   N   C   V   T   S   Y>

390          400          410          420          430
           *            *            *            *            *
CTG GCT GAC TGT GAG ACT CAG CTG TCT CAG GCC CCA AGG CAG GGC CTG
GAC CGA CTG ACA CTC TGA GTC GAC AGA GTC CGG GGT TCC GTC CCG GAC
 L   A   D   C   E   T   Q   L   S   Q   A   P   R   Q   G   L>

440          450          460          470          480
           *            *            *            *            *
CTC TAT GGC GTC CCT GTG AGC CTC AAG GAG TGC TTC ACC TAC AAG GGC
GAG ATA CCG CAG GGA CAC TCG GAG TTC CTC ACG AAG TGG ATG TTC CCG
 L   Y   G   V   P   V   S   L   K   E   C   F   T   Y   K   G>
```

FIG. 14-1

```
              490           500           510           520           530
               *             *             *             *             *
         CAG GAC TCC ACG CTG GGC TTG AGC CTG AAT GAA GGG GTG CCG GCG GAG
         GTC CTG AGG TGC GAC CCG AAC TCG GAC TTA CTT CCC CAC GGC CGC CTC
          Q   D   S   T   L   G   L   S   L   N   E   G   V   P   A   E>

540           550           560           570
                    *             *             *             *
         TGC GAC AGC GTA GTG GTG CAT GTG CTG AAG CTG CAG GGT GCC GTG CCC
         ACG CTG TCG CAT CAC CAC GTA CAC GAC TTC GAC GTC CCA CGG CAC GGG
          C   D   S   V   V   V   H   V   L   K   L   Q   G   A   V   P>

580           590           600           610           620
           *             *             *             *             *
         TTC GTG CAC ACC AAT GTT CCA CAG TCC ATG TTC AGC TAT GAC TGC AGT
         AAG CAC GTG TGG TTA CAA GGT GTC AGG TAC AAG TCG ATA CTG ACG TCA
          F   V   H   T   N   V   P   Q   S   M   F   S   Y   D   C   S>

630           640           650           660           670
               *             *             *             *             *
         AAC CCC CTC TTT GGC CAG ACC GTG AAC CCA TGG AAG TCC TCC AAA AGC
         TTG GGG GAG AAA CCG GTC TGG CAC TTG GGT ACC TTC AGG AGG TTT TCG
          N   P   L   F   G   Q   T   V   N   P   W   K   S   S   K   S>

680           690           700           710           720
                   *             *             *             *             *
         CCA GGG GGC TCC TCA GGG GGT GAA GGG GCC CTC ATC GGG TCT GGA GGC
         GGT CCC CCG AGG AGT CCC CCA CTT CCC CGG GAG TAG CCC AGA CCT CCG
          P   G   G   S   S   G   G   E   G   A   L   I   G   S   G   G>

730           740           750           760           770
                       *             *             *             *             *
         TCC CCC CTG GGC TTA GGC ACT GAT ATC GGA GGC AGC ATC CGC TTC CCC
         AGG GGG GAC CCG AAT CCG TGA CTA TAG CCT CCG TCG TAG GCG AAG GGG
          S   P   L   G   L   G   T   D   I   G   G   S   I   R   F   P>

780           790           800           810
                           *             *             *             *
         TCC TCC TTC TGC GGC ATC TGC GGC CTC AAG CCC ACA GGG AAC CGC CTC
         AGG AGG AAG ACG CCG TAG ACG CCG GAG TTC GGG TGT CCC TTG GCG GAG
          S   S   F   C   G   I   C   G   L   K   P   T   G   N   R   L>

820           830           840           850           860
           *             *             *             *             *
         AGC AAG AGT GGC CTG AAG GGC TGT GTC TAT GGA CAG GAG GCA GTG CGT
         TCG TTC TCA CCG GAC TTC CCG ACA CAG ATA CCT GTC CTC CGT CAC GCA
          S   K   S   G   L   K   G   C   V   Y   G   Q   E   A   V   R>

870           880           890           900           910
               *             *             *             *             *
         CTC TCC GTG GGC CCC ATG GCC CGG GAC GTG GAG AGC CTG GCA CTG TGC
         GAG AGG CAC CCG GGG TAC CGG GCC CTG CAC CTC TCG GAC CGT GAC ACG
          L   S   V   G   P   M   A   R   D   V   E   S   L   A   L   C>

920           930           940           950           960
                   *             *             *             *             *
         CTG CGA GCC CTG CTG TGC GAG GAC ATG TTC CGC TTG GAC CCC ACT GTG
         GAC GCT CGG GAC GAC ACG CTC CTG TAC AAG GCG AAC CTG GGG TGA CAC
          L   R   A   L   L   C   E   D   M   F   R   L   D   P   T   V>

```
CCT CCC TTG CCC TTC AGA GAA GAG GTC TAC ACC AGC TCT CAG CCC CTG
GGA GGG AAC GGG AAG TCT CTT CTC CAG ATG TGG TCG AGA GTC GGG GAC
 P   P   L   P   F   R   E   E   V   Y   T   S   S   Q   P   L>

1020           1030           1040           1050
          *              *              *              *
CGT GTG GGG TAC TAT GAG ACT GAC AAC TAT ACC ATG CCC TCC CCG GCC
GCA CAC CCC ATG ATA CTC TGA CTG TTG ATA TGG TAC GGG AGG GGC CGG
 R   V   G   Y   Y   E   T   D   N   Y   T   M   P   S   P   A>

1060           1070           1080           1090           1100
 *              *              *              *              *
ATG AGG CGG GCC GTG CTG GAG ACC AAA CAG AGC CTT GAG GCT GCG GGG
TAC TCC GCC CGG CAC GAC CTC TGG TTT GTC TCG GAA CTC CGA CGC CCC
 M   R   R   A   V   L   E   T   K   Q   S   L   E   A   A   G>

1110           1120           1130           1140           1150
         *              *              *              *              *
CAC ACG CTG GTT CCC TTC TTG CCA AGC AAC ATA CCC CAT GCT CTG GAG
GTG TGC GAC CAA GGG AAG AAC GGT TCG TTG TAT GGG GTA CGA GAC CTC
 H   T   L   V   P   F   L   P   S   N   I   P   H   A   L   E>

1160           1170           1180           1190           1200
         *              *              *              *              *
ACC CTG TCA ACA GGT GGG CTC TTC AGT GAT GGT GGC CAC ACC TTC CTA
TGG GAC AGT TGT CCA CCC GAG AAG TCA CTA CCA CCG GTG TGG AAG GAT
 T   L   S   T   G   G   L   F   S   D   G   G   H   T   F   L>

1210           1220           1230           1240           1250
         *              *              *              *              *
CAG AAC TTC AAA GGT GAT TTC GTG GAC CCC TGC CTG GGG GAC CTG GTC
GTC TTG AAG TTT CCA CTA AAG CAC CTG GGG ACG GAC CCC CTG GAC CAG
 Q   N   F   K   G   D   F   V   D   P   C   L   G   D   L   V>

1260           1270           1280           1290
              *              *              *              *
TCA ATT CTG AAG CTT CCC CAA TGG CTT AAA GGA CTG CTG GCC TTC CTG
AGT TAA GAC TTC GAA GGG GTT ACC GAA TTT CCT GAC GAC CGG AAG GAC
 S   I   L   K   L   P   Q   W   L   K   G   L   L   A   F   L>

1300           1310           1320           1330           1340
 *              *              *              *              *
GTG AAG CCT CTG CTG CCA AGG CTG TCA GCT TTC CTC AGC AAC ATG AAG
CAC TTC GGA GAC GAC GGT TCC GAC AGT CGA AAG GAG TCG TTG TAC TTC
 V   K   P   L   L   P   R   L   S   A   F   L   S   N   M   K>

1350           1360           1370           1380           1390
         *              *              *              *              *
TCT CGT TCG GCT GGA AAA CTC TGG GAA CTG CAG CAC GAG ATC GAG GTG
AGA GCA AGC CGA CCT TTT GAG ACC CTT GAC GTC GTG CTC TAG CTC CAC
 S   R   S   A   G   K   L   W   E   L   Q   H   E   I   E   V>

1400           1410           1420           1430           1440
         *              *              *              *              *
TAC CGC AAA ACC GTG ATT GCC CAG TGG AGG GCG CTG GAC CTG GAT GTG
ATG GCG TTT TGG CAC TAA CGG GTC ACC TCC CGC GAC CTG GAC CTA CAC
 Y   R   K   T   V   I   A   Q   W   R   A   L   D   L   D   V>

1450           1460           1470           1480           1490
         *              *              *              *              *
GTG CTG ACC CCC ATG CTG GCC CCT GCT CTG GAC TTG AAT GCC CCA GGC
CAC GAC TGG GGG TAC GAC CGG GGA CGA GAC CTG AAC TTA CGG GGT CCG
```

FIG. 14-3

```
        V    L    T    P    M    L    A    A    L    D    L    N    A    P    G>
          1500          1510          1520          1530
            *             *             *             *
        AGG  GCC  ACA  GGG  GCC  GTC  AGC  TAC  ACT  ATG  CTG  TAC  AAC  TGC  CTG  GAC
        TCC  CGG  TGT  CCC  CGG  CAG  TCG  ATG  TGA  TAC  GAC  ATG  TTG  ACG  GAC  CTG
         R    A    T    G    A    V    S    Y    T    M    L    Y    N    C    L    D>
 1540          1550          1560          1570          1580
   *             *             *             *             *
 TTC  CCT  GCA  GGG  GTG  GTG  CCT  GTC  ACC  ACG  GTG  ACT  GCT  GAG  GAC  GAG
 AAG  GGA  CGT  CCC  CAC  CAC  GGA  CAG  TGG  TGC  CAC  TGA  CGA  CTC  CTG  CTC
  F    P    A    G    V    V    P    V    T    T    V    T    A    E    D    E>
 1590          1600          1610          1620          1630
   *             *             *             *             *
 GCC  CAG  ATG  GAA  CAT  TAC  AGG  GGC  TAC  TTT  GGG  GAT  ATC  TGG  GAC  AAG
 CGG  GTC  TAC  CTT  GTA  ATG  TCC  CCG  ATG  AAA  CCC  CTA  TAG  ACC  CTG  TTC
  A    Q    M    E    H    Y    R    G    Y    F    G    D    I    W    D    K>
        1640          1650          1660          1670          1680
          *             *             *             *             *
        ATG  CTG  CAG  AAG  GGC  ATG  AAG  AAG  AGT  GTG  GGG  CTG  CCG  GTG  GCC  GTG
        TAC  GAC  GTC  TTC  CCG  TAC  TTC  TTC  TCA  CAC  CCC  GAC  GGC  CAC  CGG  CAC
         M    L    Q    K    G    M    K    K    S    V    G    L    P    V    A    V>
            1690          1700          1710          1720          1730
              *             *             *             *             *
            CAG  TGT  GTG  GCT  CTG  CCC  TGG  CAA  GAA  GAG  TTG  TGT  CTG  CGG  TTC  ATG
            GTC  ACA  CAC  CGA  GAC  GGG  ACC  GTT  CTT  CTC  AAC  ACA  GAC  GCC  AAG  TAC
             Q    C    V    A    L    P    W    Q    E    E    L    C    L    R    F    M>
                  1740          1750          1760          1770
                    *             *             *             *
                  CGG  GAG  GTG  GAG  CGA  CTG  ATG  ACC  CCT  GAA  AAG  CAG  TCA  TCC  TGA  TGG
                  GCC  CTC  CAC  CTC  GCT  GAC  TAC  TGG  GGA  CTT  TTC  GTC  AGT  AGG  ACT  ACC
                   R    E    V    E    R    L    M    T    P    E    K    Q    S    S   [*]
 1780          1790          1800          1810          1820
   *             *             *             *             *
 CTC  TGG  CTC  CAG  AGG  ACC  TGA  GAC  TCA  CAC  TCT  CTG  CAG  CCC  AGC  CTA
 GAG  ACC  GAG  GTC  TCC  TGG  ACT  CTG  AGT  GTG  AGA  GAC  GTC  GGG  TCG  GAT
        1830          1840          1850          1860          1870
          *             *             *             *             *
        GTC  AGG  GCA  CAG  CTG  CCC  TGC  TGC  CAC  AGC  AAG  GAA  ATG  TCC  TGC  ATG
        CAG  TCC  CGT  GTC  GAC  GGG  ACG  ACG  GTG  TCG  TTC  CTT  TAC  AGG  ACG  TAC
                1880          1890          1900          1910          1920
                  *             *             *             *             *
                GGG  CAG  AGG  CTT  CCG  TGT  CCT  CTC  CCC  CAA  CCC  CCT  GCA  AGA  AGC  GCC
                CCC  GTC  TCC  GAA  GGC  ACA  GGA  GAG  GGG  GTT  GGG  GGA  CGT  TCT  TCG  CGG
                        1930          1940          1950          1960          1970
                          *             *             *             *             *
                        GAC  TCC  CTG  AGT  CTG  GAC  CTC  CAT  CCC  TGC  TCT  GGT  CCC  CTC  TCT  TCG
                        CTG  AGG  GAC  TCA  GAC  CTG  GAG  GTA  GGG  ACG  AGA  CCA  GGG  GAG  AGA  AGC
```

FIG. 14-4

```
            1980            1990            2000            2010
             *               *               *               *
   TCC TGA TCC CTC CAC CCC CAT GTG GCA GCC CAT GGG TAT GAC ATA GGC
   AGG ACT AGG GAG GTG GGG GTA CAC CGT CGG GTA CCC ATA CTG TAT CCG 2020            2030            2040
   *               *               *
 CAA GGC CCA ACT AAC AGC CCC GGA ATT
 GTT CCG GGT TGA TTG TCG GGG CCT TAA
```

FIG. 14-5

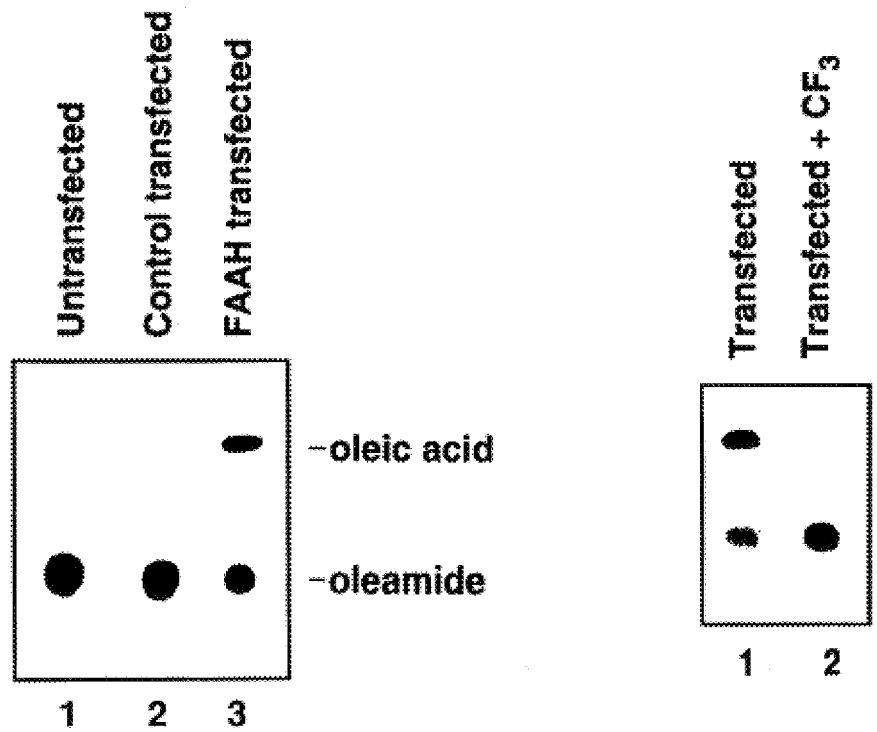
FIG. 15A
FIG. 15B
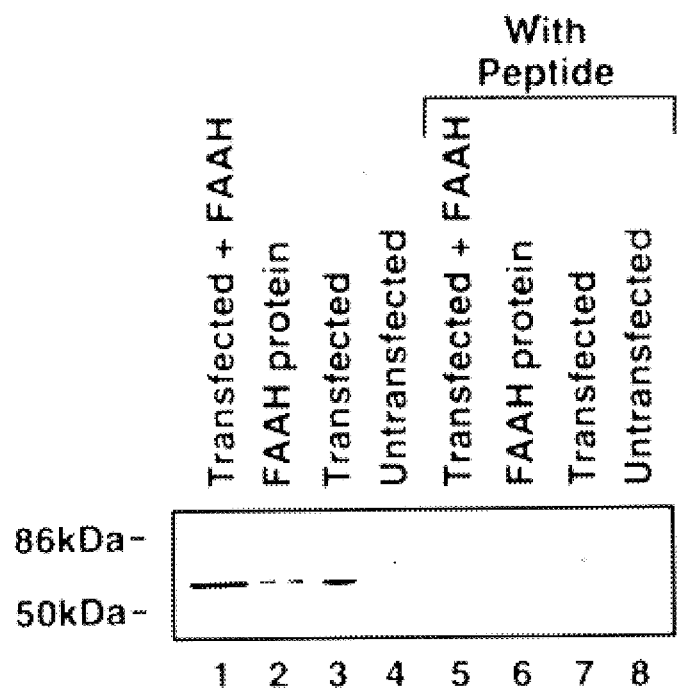
FIG. 15C

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
      (A) LENGTH: 783 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 1..783

(xi) SEQUENCE DESCRIPTION: SEQ ID NO:1:

```
AGC CCA GGA GGT TCC TCA GGG GGT GAG GGG GCT CTC ATT GGA TCT GGA    48
Ser Pro Gly Gly Ser Ser Gly Gly Glu Gly Ala Leu Ile Gly Ser Gly
 1               5                  10                  15

GGT TCC CCT CTG GGT TTA GGC ACT GAC ATT GGC GGC AGC ATC CGG TTC    96
Gly Ser Pro Leu Gly Leu Gly Thr Asp Ile Gly Gly Ser Ile Arg Phe
            20                  25                  30

CCT TCT GCC TTC TGC GGC ATC TGT GGC CTC AAG CCT ACT GGC AAC CGC   144
Pro Ser Ala Phe Cys Gly Ile Cys Gly Leu Lys Pro Thr Gly Asn Arg
        35                  40                  45

CTC AGC AAG AGT GGC CTG AAG GGC TGT GTC TAT GGA CAG ACG GCA GTG   192
Leu Ser Lys Ser Gly Leu Lys Gly Cys Val Tyr Gly Gln Thr Ala Val
    50                  55                  60

CAG CTT TCT CTT GGC CCC ATG GCC CGG GAT GTG GAG AGC CTG GCG CTA   240
Gln Leu Ser Leu Gly Pro Met Ala Arg Asp Val Glu Ser Leu Ala Leu
 65                 70                  75                  80

TGC CTG AAA GCT CTA CTG TGT GAG CAC TTG TTC ACC TTG GAC CCT ACC   288
Cys Leu Lys Ala Leu Leu Cys Glu His Leu Phe Thr Leu Asp Pro Thr
                85                  90                  95

GTG CCT CCC TTT CCC TTC AGA GAG GAG GTC TAT AGA AGT TCT AGA CCC   336
Val Pro Pro Phe Pro Phe Arg Glu Glu Val Tyr Arg Ser Ser Arg Pro
            100                 105                 110

CTG CGT GTG GGG TAC TAT GAG ACT GAC AAC TAT ACC ATG CCC AGC CCA   384
Leu Arg Val Gly Tyr Tyr Glu Thr Asp Asn Tyr Thr Met Pro Ser Pro
        115                 120                 125

GCT ATG AGG AGG GCT CTG ATA GAG ACC AAG CAG AGA CTT GAG GCT GCT   432
Ala Met Arg Arg Ala Leu Ile Glu Thr Lys Gln Arg Leu Glu Ala Ala
130                 135                 140

GGC CAC ACG CTG ATT CCC TTC TTA CCC AAC AAC ATA CCC TAC GCC CTG   480
Gly His Thr Leu Ile Pro Phe Leu Pro Asn Asn Ile Pro Tyr Ala Leu
145                 150                 155                 160

GAG GTC CTG TCT GCG GGC GGC CTG TTC AGT GAC GGT GGC CGC AGT TTT   528
Glu Val Leu Ser Ala Gly Gly Leu Phe Ser Asp Gly Gly Arg Ser Phe
                165                 170                 175

CTC CAA AAC TTC AAA GGT GAC TTT GTG GAT CCC TGC TTG GGA GAC CTG   576
Leu Gln Asn Phe Lys Gly Asp Phe Val Asp Pro Cys Leu Gly Asp Leu
            180                 185                 190

ATC TTA ATT CTG AGG CTG CCC AGC TGG TTT AAA AGA CTG CTG AGC CTC   624
Ile Leu Ile Leu Arg Leu Pro Ser Trp Phe Lys Arg Leu Leu Ser Leu
        195                 200                 205

CTG CTG AAG CCT CTG TTT CCT CGG CTG GCA GCC TTT CTC AAC AGT ATG   672
Leu Leu Lys Pro Leu Phe Pro Arg Leu Ala Ala Phe Leu Asn Ser Met
210                 215                 220

CGT CCT CGG TCA GCT GAA AAG CTG TGG AAA CTG CAG CAT GAG ATT GAG   720
Arg Pro Arg Ser Ala Glu Lys Leu Trp Lys Leu Gln His Glu Ile Glu
225                 230                 235                 240

ATG TAT CGC CAG TCT GTG ATT GCC CAG TGG AAA GCG ATG AAC TTG GAT   768
Met Tyr Arg Gln Ser Val Ile Ala Gln Trp Lys Ala Met Asn Leu Asp
                245                 250                 255

GTG CTG CTG ACC TAA                                                783
Val Leu Leu Thr
            260
```

(2) INFORMATION FOR SEQ ID NO:2:

(i) SEQUENCE CHARACTERISTICS:
        (A) LENGTH: 260 amino acids
        (B) TYPE: amino acid
        (D) TOPOLOGY: linear (ii) MOLECULE TYPE: protein (xi) SEQUENCE DESCRIPTION: SEQ ID NO:2:

```
Ser Pro Gly Gly Ser Ser Gly Gly Glu Gly Ala Leu Ile Gly Ser Gly
  1               5                  10                  15

Gly Ser Pro Leu Gly Leu Gly Thr Asp Ile Gly Gly Ser Ile Arg Phe
              20                  25                  30

Pro Ser Ala Phe Cys Gly Ile Cys Gly Leu Lys Pro Thr Gly Asn Arg
              35                  40                  45

Leu Ser Lys Ser Gly Leu Lys Gly Cys Val Tyr Gly Gln Thr Ala Val
          50                  55                  60

Gln Leu Ser Leu Gly Pro Met Ala Arg Asp Val Glu Ser Leu Ala Leu
 65                  70                  75                  80

Cys Leu Lys Ala Leu Leu Cys Glu His Leu Phe Thr Leu Asp Pro Thr
                  85                  90                  95

Val Pro Pro Phe Pro Phe Arg Glu Glu Val Tyr Arg Ser Ser Arg Pro
              100                 105                 110

Leu Arg Val Gly Tyr Tyr Glu Thr Asp Asn Tyr Thr Met Pro Ser Pro
              115                 120                 125

Ala Met Arg Arg Ala Leu Ile Glu Thr Lys Gln Arg Leu Glu Ala Ala
    130                 135                 140

Gly His Thr Leu Ile Pro Phe Leu Pro Asn Asn Ile Pro Tyr Ala Leu
145                 150                 155                 160

Glu Val Leu Ser Ala Gly Gly Leu Phe Ser Asp Gly Gly Arg Ser Phe
                165                 170                 175

Leu Gln Asn Phe Lys Gly Asp Phe Val Asp Pro Cys Leu Gly Asp Leu
              180                 185                 190

Ile Leu Ile Leu Arg Leu Pro Ser Trp Phe Lys Arg Leu Leu Ser Leu
          195                 200                 205

Leu Leu Lys Pro Leu Phe Pro Arg Leu Ala Ala Phe Leu Asn Ser Met
 210                 215                 220

Arg Pro Arg Ser Ala Glu Lys Leu Trp Lys Leu Gln His Glu Ile Glu
225                 230                 235                 240

Met Tyr Arg Gln Ser Val Ile Ala Gln Trp Lys Ala Met Asn Leu Asp
              245                 250                 255

Val Leu Leu Thr
              260

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

CGGAATTCGG NGGNGARGGN GC                                                   22

(2) INFORMATION FOR SEQ ID NO:4:

(i) SEQUENCE CHARACTERISTICS:
        (A) LENGTH: 5 amino acids
        (B) TYPE: amino acid
        (D) TOPOLOGY: linear
```

(ii) MOLECULE TYPE: peptide (v) FRAGMENT TYPE: internal (xi) SEQUENCE DESCRIPTION: SEQ ID NO:4:

Gly Gly Glu Gly Ala
1               5

(2) INFORMATION FOR SEQ ID NO:5:

(i) SEQUENCE CHARACTERISTICS:
            (A) LENGTH: 31 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:5:

Gly Gly Ser Ser Gly Gly Glu Gly Ala Leu Ile Gly Ser Gly Gly Ser
1               5                  10                  15

Pro Leu Gly Leu Gly Thr Asp Ile Gly Gly Ser Ile Arg Phe Pro
            20                  25                  30

(2) INFORMATION FOR SEQ ID NO:6:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:6:

Ser Pro Gly Gly Ser Ser Gly Gly Glu Gly Ala Leu Ile Gly Ser
1               5                  10                  15

(2) INFORMATION FOR SEQ ID NO:7:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:7:

Ala Leu Ile Gly Ser Gly Gly Ser Pro Leu Gly Leu Gly Thr Asp
1               5                  10                  15

(2) INFORMATION FOR SEQ ID NO:8:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:8:

Gly Leu Gly Thr Asp Ile Gly Gly Ser Ile Arg Phe Pro Ser Ala
1               5                  10                  15

(2) INFORMATION FOR SEQ ID NO:9:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:9:

```
Arg Phe Pro Ser Ala Phe Cys Gly Ile Cys Gly Leu Lys Pro Thr
1               5                  10                  15
```

(2) INFORMATION FOR SEQ ID NO:10:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:10:

```
Gly Leu Lys Pro Thr Gly Asn Arg Leu Ser Lys Ser Gly Leu Lys
1               5                  10                  15
```

(2) INFORMATION FOR SEQ ID NO:11:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:11:

```
Lys Ser Gly Leu Lys Gly Cys Val Tyr Gly Gln Thr Ala Val Gln
1               5                  10                  15
```

(2) INFORMATION FOR SEQ ID NO:12:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

```
Gln Thr Ala Val Gln Leu Ser Leu Gly Pro Met Ala Arg Asp Val
1               5                  10                  15
```

(2) INFORMATION FOR SEQ ID NO:13:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:13:

Met Ala Arg Asp Val Glu Ser Leu Ala Leu Cys Leu Lys Ala Leu
1               5                   10                  15

(2) INFORMATION FOR SEQ ID NO:14:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:14:

Cys Leu Lys Ala Leu Leu Cys Glu His Leu Phe Thr Leu Asp Pro
1               5                   10                  15

(2) INFORMATION FOR SEQ ID NO:15:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:15:

Phe Thr Leu Asp Pro Thr Val Pro Pro Phe Pro Phe Arg Glu Glu
1               5                   10                  15

(2) INFORMATION FOR SEQ ID NO:16:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:16:

Pro Phe Arg Glu Glu Val Tyr Arg Ser Ser Arg Pro Leu Arg Val
1               5                   10                  15

(2) INFORMATION FOR SEQ ID NO:17:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:17:

Arg Pro Leu Arg Val Gly Tyr Tyr Glu Thr Asp Asn Tyr Thr Met
1               5                   10                  15

(2) INFORMATION FOR SEQ ID NO:18:

(i) SEQUENCE CHARACTERISTICS:

(A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:18:

Asp Asn Tyr Thr Met Pro Ser Pro Ala Met Arg Arg Ala Leu Ile
1               5                  10                  15

(2) INFORMATION FOR SEQ ID NO:19:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:19:

Arg Arg Ala Leu Ile Glu Thr Lys Gln Arg Leu Glu Ala Ala Gly
1               5                  10                  15

(2) INFORMATION FOR SEQ ID NO:20:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:20:

Leu Glu Ala Ala Gly His Thr Leu Ile Pro Phe Leu Pro Asn Asn
1               5                  10                  15

(2) INFORMATION FOR SEQ ID NO:21:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:21:

Phe Leu Pro Asn Asn Ile Pro Tyr Ala Leu Glu Val Leu Ser Ala
1               5                  10                  15

(2) INFORMATION FOR SEQ ID NO:22:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:22:

Glu Val Leu Ser Ala Gly Gly Leu Phe Ser Asp Gly Gly Arg Ser 1               5                  10                 15

(2) INFORMATION FOR SEQ ID NO:23:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:23:

Asp Gly Gly Arg Ser Phe Leu Gln Asn Phe Lys Gly Asp Phe Val
1               5                  10                 15

(2) INFORMATION FOR SEQ ID NO:24:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:24:

Lys Gly Asp Phe Val Asp Pro Cys Leu Gly Asp Leu Ile Leu Ile
1               5                  10                 15

(2) INFORMATION FOR SEQ ID NO:25:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:25:

Asp Leu Ile Leu Ile Leu Arg Leu Pro Ser Trp Phe Lys Arg Leu
1               5                  10                 15

(2) INFORMATION FOR SEQ ID NO:26:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:26:

Trp Phe Lys Arg Leu Leu Ser Leu Leu Leu Lys Pro Leu Phe Pro
1               5                  10                 15

(2) INFORMATION FOR SEQ ID NO:27:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:27:

Lys Pro Leu Phe Pro Arg Leu Ala Ala Phe Leu Asn Ser Met Arg
1               5                   10                  15

(2) INFORMATION FOR SEQ ID NO:28:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:28:

Leu Asn Ser Met Arg Pro Arg Ser Ala Glu Lys Leu Trp Lys Leu
1               5                   10                  15

(2) INFORMATION FOR SEQ ID NO:29:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:29:

Lys Leu Trp Lys Leu Gln His Glu Ile Glu Met Tyr Arg Gln Ser
1               5                   10                  15

(2) INFORMATION FOR SEQ ID NO:30:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:30:

Met Tyr Arg Gln Ser Val Ile Ala Gln Trp Lys Ala Met Asn Leu
1               5                   10                  15

(2) INFORMATION FOR SEQ ID NO:31:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:31:

Lys Ala Met Asn Leu Asp Val Leu Leu Thr Pro Met Leu Gly Pro
1               5                   10                  15

(2) INFORMATION FOR SEQ ID NO:32:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:32:

Pro Met Leu Gly Pro Ala Leu Asp Leu Asn Thr Pro Gly Arg
1               5                   10

(2) INFORMATION FOR SEQ ID NO:33:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:33:

CGGGATCCGG CATNGTRTAR TTRTC                                           25

(2) INFORMATION FOR SEQ ID NO:34:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:34:

Asp Asn Tyr Thr Met Pro
1               5

(2) INFORMATION FOR SEQ ID NO:35:

(i) SEQUENCE CHARACTERISTICS:
            (A) LENGTH: 2472 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: CDS
            (B) LOCATION: 50..1789

(xi) SEQUENCE DESCRIPTION: SEQ ID NO:35:

GGTTTGTGCG AGCCGAGTTC TCTCGGGTGG CGGTCGGCTG CAGGAGATC ATG GTG        55
                                                       Met Val
                                                         1

CTG AGC GAA GTG TGG ACC ACG CTG TCT GGG GTC TCC GGG GTT TGC CTA     103
Leu Ser Glu Val Trp Thr Thr Leu Ser Gly Val Ser Gly Val Cys Leu
        5                  10                  15

```
GCC TGC AGC TTG TTG TCG GCG GCG GTG GTC CTG CGA TGG ACC GGG CGC        151
Ala Cys Ser Leu Leu Ser Ala Ala Val Val Leu Arg Trp Thr Gly Arg
 20              25                  30

CAG AAG GCC CGG GGC GCG GCG ACC AGG GCG CGG CAG AAG CAG CGA GCC        199
Gln Lys Ala Arg Gly Ala Ala Thr Arg Ala Arg Gln Lys Gln Arg Ala
 35              40                  45                  50

AGC CTG GAG ACC ATG GAC AAG GCG GTG CAG CGC TTC CGG CTG CAG AAT        247
Ser Leu Glu Thr Met Asp Lys Ala Val Gln Arg Phe Arg Leu Gln Asn
                 55                  60                  65

CCT GAC CTG GAC TCG GAG GCC TTG CTA ACC CTG CCC CTA CTC CAA CTG        295
Pro Asp Leu Asp Ser Glu Ala Leu Leu Thr Leu Pro Leu Leu Gln Leu
         70                  75                  80

GTA CAG AAG TTA CAG AGT GGA GAG CTG TCC CCA GAG GCT GTG TTC TTT        343
Val Gln Lys Leu Gln Ser Gly Glu Leu Ser Pro Glu Ala Val Phe Phe
             85                  90                  95

ACT TAC CTG GGA AAG GCC TGG GAA GTG AAC AAA GGG ACC AAC TGC GTG        391
Thr Tyr Leu Gly Lys Ala Trp Glu Val Asn Lys Gly Thr Asn Cys Val
100                 105                 110

ACC TCC TAT CTG ACC GAC TGT GAG ACT CAG CTG TCC CAG GCC CCA CGG        439
Thr Ser Tyr Leu Thr Asp Cys Glu Thr Gln Leu Ser Gln Ala Pro Arg
115                 120                 125                 130

CAG GGC CTG CTC TAT GGT GTC CCT GTG AGC CTC AAG GAA TGC TTC AGC        487
Gln Gly Leu Leu Tyr Gly Val Pro Val Ser Leu Lys Glu Cys Phe Ser
                135                 140                 145

TAC AAG GGC CAC GAC TCC ACA CTG GGC TTG AGC CTG AAT GAG GGC ATG        535
Tyr Lys Gly His Asp Ser Thr Leu Gly Leu Ser Leu Asn Glu Gly Met
                150                 155                 160

CCA TCG GAA TCT GAC TGT GTG GTG GTG CAA GTG TTG AAG CTG CAG GGA        583
Pro Ser Glu Ser Asp Cys Val Val Val Gln Val Leu Lys Leu Gln Gly
                165                 170                 175

GCT GTG CCC TTT GTG CAT ACC AAT GTC CCC CAG TCC ATG TTA AGC TTT        631
Ala Val Pro Phe Val His Thr Asn Val Pro Gln Ser Met Leu Ser Phe
180                 185                 190

GAC TGC AGT AAC CCT CTC TTT GGC CAG ACC ATG AAC CCA TGG AAG TCC        679
Asp Cys Ser Asn Pro Leu Phe Gly Gln Thr Met Asn Pro Trp Lys Ser
195                 200                 205                 210

TCC AAG AGC CCA GGA GGT TCC TCA GGG GGT GAG GGG GCT CTC ATT GGA        727
Ser Lys Ser Pro Gly Gly Ser Ser Gly Gly Glu Gly Ala Leu Ile Gly
                215                 220                 225

TCT GGA GGT TCC CCT CTG GGT TTA GGC ACT GAC ATT GGC GGC AGC ATC        775
Ser Gly Gly Ser Pro Leu Gly Leu Gly Thr Asp Ile Gly Gly Ser Ile
                230                 235                 240

CGG TTC CCT TCT GCC TTC TGC GGC ATC TGT GGC CTC AAG CCT ACT GGC        823
Arg Phe Pro Ser Ala Phe Cys Gly Ile Cys Gly Leu Lys Pro Thr Gly
                245                 250                 255

AAC CGC CTC AGC AAG AGT GGC CTG AAG GGC TGT GTC TAT GGA CAG ACG        871
Asn Arg Leu Ser Lys Ser Gly Leu Lys Gly Cys Val Tyr Gly Gln Thr
260                 265                 270

GCA GTG CAG CTT TCT CTT GGC CCC ATG GCC CGG GAT GTG GAG AGC CTG        919
Ala Val Gln Leu Ser Leu Gly Pro Met Ala Arg Asp Val Glu Ser Leu
275                 280                 285                 290

GCG CTA TGC CTG AAA GCT CTA CTG TGT GAG CAC TTG TTC ACC TTG GAC        967
Ala Leu Cys Leu Lys Ala Leu Leu Cys Glu His Leu Phe Thr Leu Asp
                295                 300                 305

CCT ACC GTG CCT CCC TTG CCC TTC AGA GAG GAG GTC TAT AGA AGT TCT       1015
Pro Thr Val Pro Pro Leu Pro Phe Arg Glu Glu Val Tyr Arg Ser Ser
                310                 315                 320

AGA CCC CTG CGT GTG GGG TAC TAT GAG ACT GAC AAC TAT ACC ATG CCC       1063
Arg Pro Leu Arg Val Gly Tyr Tyr Glu Thr Asp Asn Tyr Thr Met Pro
325                 330                 335
```

```
AGC CCA GCT ATG AGG AGG GCT CTG ATA GAG ACC AAG CAG AGA CTT GAG      1111
Ser Pro Ala Met Arg Arg Ala Leu Ile Glu Thr Lys Gln Arg Leu Glu
    340                 345                 350

GCT GCT GGC CAC ACG CTG ATT CCC TTC TTA CCC AAC AAC ATA CCC TAC      1159
Ala Ala Gly His Thr Leu Ile Pro Phe Leu Pro Asn Asn Ile Pro Tyr
355                 360                 365                 370

GCC CTG GAG GTC CTG TCT GCG GGC GGC CTG TTC AGT GAC GGT GGC CGC      1207
Ala Leu Glu Val Leu Ser Ala Gly Gly Leu Phe Ser Asp Gly Gly Arg
            375                 380                 385

AGT TTT CTC CAA AAC TTC AAA GGT GAC TTT GTG GAT CCC TGC TTG GGA      1255
Ser Phe Leu Gln Asn Phe Lys Gly Asp Phe Val Asp Pro Cys Leu Gly
390                 395                 400

GAC CTG ATC TTA ATT CTG AGG CTG CCC AGC TGG TTT AAA AGA CTG CTG      1303
Asp Leu Ile Leu Ile Leu Arg Leu Pro Ser Trp Phe Lys Arg Leu Leu
    405                 410                 415

AGC CTC CTG CTG AAG CCT CTG TTT CCT CGG CTG GCA GCC TTT CTC AAC      1351
Ser Leu Leu Leu Lys Pro Leu Phe Pro Arg Leu Ala Ala Phe Leu Asn
420                 425                 430

AGT ATG CGT CCT CGG TCA GCT GAA AAG CTG TGG AAA CTG CAG CAT GAG      1399
Ser Met Arg Pro Arg Ser Ala Glu Lys Leu Trp Lys Leu Gln His Glu
435                 440                 445                 450

ATT GAG ATG TAT CGC CAG TCT GTG ATT GCC CAG TGG AAA GCG ATG AAC      1447
Ile Glu Met Tyr Arg Gln Ser Val Ile Ala Gln Trp Lys Ala Met Asn
                455                 460                 465

TTG GAT GTG CTG CTG ACC CCC ATG TTG GGC CCT GCT CTG GAT TTG AAC      1495
Leu Asp Val Leu Leu Thr Pro Met Leu Gly Pro Ala Leu Asp Leu Asn
            470                 475                 480

ACA CCG GGC AGA GCC ACA GGG GCT ATC AGC TAC ACC GTT CTC TAC AAC      1543
Thr Pro Gly Arg Ala Thr Gly Ala Ile Ser Tyr Thr Val Leu Tyr Asn
            485                 490                 495

TGC CTG GAC TTC CCT GCG GGG GTG GTG CCT GTC ACC ACT GTG ACC GCC      1591
Cys Leu Asp Phe Pro Ala Gly Val Val Pro Val Thr Thr Val Thr Ala
500                 505                 510

GAG GAC GAT GCC CAG ATG GAA CTC TAC AAA GGC TAC TTT GGG GAT ATC      1639
Glu Asp Asp Ala Gln Met Glu Leu Tyr Lys Gly Tyr Phe Gly Asp Ile
515                 520                 525                 530

TGG GAC ATC ATC CTG AAG AAG GCC ATG AAA AAT AGT GTC GGT CTG CCT      1687
Trp Asp Ile Ile Leu Lys Lys Ala Met Lys Asn Ser Val Gly Leu Pro
                535                 540                 545

GTG GCT GTG CAG TGC GTG GCT CTG CCC TGG CAG GAA GAG CTG TGT CTG      1735
Val Ala Val Gln Cys Val Ala Leu Pro Trp Gln Glu Glu Leu Cys Leu
            550                 555                 560

AGG TTC ATG CGG GAG GTG GAA CAG CTG ATG ACC CCT CAA AAG CAG CCA      1783
Arg Phe Met Arg Glu Val Glu Gln Leu Met Thr Pro Gln Lys Gln Pro
            565                 570                 575

TCG TGAGGGTCGT TCATCCGCCA GCTCTGGAGG ACCTAAGGCC CATGCGCTGT           1836
Ser
580

GCACTGTAGC CCCATGTATT CAGGAGCCAC CACCCACGAG GGAACGCCCA GCACAGGGAA    1896

GAGGTGTCTA CCTGCCCTCC CCTGGACTCC TGCAGCCACA ACCAAGTCTG GACCTTCCTC    1956

CCCGTTATGG TCTACTTTCC ATCCTGATTC CCTGCTTTTT ATGGCAGCCA GCAGGAATGA    2016

CGTGGGCCAA GGATCACCAA CATTCAAAAA CAATGCGTTT ATCTATTTTC TGGGTATCTC    2076

CATTAGGGCC CTGGGAACCA GAGTGCTGGG AAGGCTGTCC AGACCCTCCA GAGCTGGCTG    2136

TAACCACATC ACTCTCCTGC TCCAAAGCCT CCCTAGTTCT GTCACCCACA AGATAGACAC    2196

AGGGACATGT CCTTGGCACT TGACTCCTGT CCTTCCTTTC TTATTCAGAT TGACCCCAGC    2256
```

```
CTTGATGGAC CCTGCCCCTG CACTTCCTTC CTCAGTCCAC CTCTCTGCCG ACACGCCCTT      2316

TTTATGGCTC CTCTATTTGT TGTGGAGACA AGGTTTCTCT CAGTAGCCCT GGCTGTCCAG      2376

GACCTCACTC TGTAGATGAG GCTGGCTTTC AACTCACAAG GCTGCCTGCC TGGGTGCTGG      2436

GATTAAAGGC GTATGCCACC ACAAAGAAAA AAAAAA                                2472
```

(2) INFORMATION FOR SEQ ID NO:36:

(i) SEQUENCE CHARACTERISTICS:
        (A) LENGTH: 579 amino acids
        (B) TYPE: amino acid
        (D) TOPOLOGY: linear (ii) MOLECULE TYPE: protein (xi) SEQUENCE DESCRIPTION: SEQ ID NO:36:

```
Met Val Leu Ser Glu Val Trp Thr Thr Leu Ser Gly Val Ser Gly Val
  1               5                  10                  15

Cys Leu Ala Cys Ser Leu Leu Ser Ala Ala Val Val Leu Arg Trp Thr
                 20                  25                  30

Gly Arg Gln Lys Ala Arg Gly Ala Ala Thr Arg Ala Arg Gln Lys Gln
             35                  40                  45

Arg Ala Ser Leu Glu Thr Met Asp Lys Ala Val Gln Arg Phe Arg Leu
         50                  55                  60

Gln Asn Pro Asp Leu Asp Ser Glu Ala Leu Leu Thr Leu Pro Leu Leu
 65                  70                  75                  80

Gln Leu Val Gln Lys Leu Gln Ser Gly Glu Leu Ser Pro Glu Ala Val
                 85                  90                  95

Phe Phe Thr Tyr Leu Gly Lys Ala Trp Glu Val Asn Lys Gly Thr Asn
            100                 105                 110

Cys Val Thr Ser Tyr Leu Thr Asp Cys Glu Thr Gln Leu Ser Gln Ala
        115                 120                 125

Pro Arg Gln Gly Leu Leu Tyr Gly Val Pro Val Ser Leu Lys Glu Cys
    130                 135                 140

Phe Ser Tyr Lys Gly His Asp Ser Thr Leu Gly Leu Ser Leu Asn Glu
145                 150                 155                 160

Gly Met Pro Ser Glu Ser Asp Cys Val Val Gln Val Leu Lys Leu
                165                 170                 175

Gln Gly Ala Val Pro Phe Val His Thr Asn Val Pro Gln Ser Met Leu
            180                 185                 190

Ser Phe Asp Cys Ser Asn Pro Leu Phe Gly Gln Thr Met Asn Pro Trp
        195                 200                 205

Lys Ser Ser Lys Ser Pro Gly Gly Ser Gly Gly Glu Gly Ala Leu
    210                 215                 220

Ile Gly Ser Gly Gly Ser Pro Leu Gly Leu Gly Thr Asp Ile Gly Gly
225                 230                 235                 240

Ser Ile Arg Phe Pro Ser Ala Phe Cys Gly Ile Cys Gly Leu Lys Pro
                245                 250                 255

Thr Gly Asn Arg Leu Ser Lys Ser Gly Leu Lys Gly Cys Val Tyr Gly
            260                 265                 270

Gln Thr Ala Val Gln Leu Ser Leu Gly Pro Met Ala Arg Asp Val Glu
        275                 280                 285

Ser Leu Ala Leu Cys Leu Lys Ala Leu Leu Cys Glu His Leu Phe Thr
    290                 295                 300

Leu Asp Pro Thr Val Pro Pro Leu Pro Phe Arg Glu Glu Val Tyr Arg
305                 310                 315                 320
```

```
Ser Ser Arg Pro Leu Arg Val Gly Tyr Tyr Glu Thr Asp Asn Tyr Thr
            325                 330                 335

Met Pro Ser Pro Ala Met Arg Arg Ala Leu Ile Glu Thr Lys Gln Arg
            340                 345                 350

Leu Glu Ala Ala Gly His Thr Leu Ile Pro Phe Leu Pro Asn Asn Ile
            355                 360                 365

Pro Tyr Ala Leu Glu Val Leu Ser Ala Gly Gly Leu Phe Ser Asp Gly
            370                 375             380

Gly Arg Ser Phe Leu Gln Asn Phe Lys Gly Asp Phe Val Asp Pro Cys
385                 390                 395                 400

Leu Gly Asp Leu Ile Leu Ile Leu Arg Leu Pro Ser Trp Phe Lys Arg
            405                 410                 415

Leu Leu Ser Leu Leu Leu Lys Pro Leu Phe Pro Arg Leu Ala Ala Phe
            420                 425             430

Leu Asn Ser Met Arg Pro Arg Ser Ala Glu Lys Leu Trp Lys Leu Gln
            435                 440                 445

His Glu Ile Glu Met Tyr Arg Gln Ser Val Ile Ala Gln Trp Lys Ala
            450                 455             460

Met Asn Leu Asp Val Leu Leu Thr Pro Met Leu Gly Pro Ala Leu Asp
465                 470                 475                 480

Leu Asn Thr Pro Gly Arg Ala Thr Gly Ala Ile Ser Tyr Thr Val Leu
            485                 490                 495

Tyr Asn Cys Leu Asp Phe Pro Ala Gly Val Val Pro Val Thr Thr Val
            500                 505             510

Thr Ala Glu Asp Asp Ala Gln Met Glu Leu Tyr Lys Gly Tyr Phe Gly
            515                 520                 525

Asp Ile Trp Asp Ile Ile Leu Lys Lys Ala Met Lys Asn Ser Val Gly
            530                 535             540

Leu Pro Val Ala Val Gln Cys Val Ala Leu Pro Trp Gln Glu Glu Leu
545                 550                 555                 560

Cys Leu Arg Phe Met Arg Glu Val Glu Gln Leu Met Thr Pro Gln Lys
            565                 570                 575

Gln Pro Ser (2) INFORMATION FOR SEQ ID NO:37:

(i) SEQUENCE CHARACTERISTICS:
        (A) LENGTH: 2472 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:37:

TTTTTTTTTT CTTTGTGGTG GCATACGCCT TTAATCCCAG CACCCAGGCA GGCAGCCTTG      60

TGAGTTGAAA GCCAGCCTCA TCTACAGAGT GAGGTCCTGG ACAGCCAGGG CTACTGAGAG    120

AAACCTTGTC TCCACAACAA ATAGAGGAGC CATAAAAAGG GCGTGTCGGC AGAGAGGTGG    180

ACTGAGGAAG GAAGTGCAGG GGCAGGGTCC ATCAAGGCTG GGGTCAATCT GAATAAGAAA    240

GGAAGGACAG GAGTCAAGTG CCAAGGACAT GTCCCTGTGT CTATCTTGTG GGTGACAGAA    300

CTAGGGAGGC TTTGGAGCAG GAGAGTGATG TGGTTACAGC CAGCTCTGGA GGGTCTGGAC    360
```

```
AGCCTTCCCA GCACTCTGGT TCCCAGGGCC CTAATGGAGA TACCCAGAAA ATAGATAAAC    420

GCATTGTTTT TGAATGTTGG TGATCCTTGG CCCACGTCAT TCCTGCTGGC TGCCATAAAA    480

AGCAGGGAAT CAGGATGGAA AGTAGACCAT AACGGGGAGG AAGGTCCAGA CTTGGTTGTG    540

GCTGCAGGAG TCCAGGGGAG GGCAGGTAGA CACCTCTTCC CTGTGCTGGG CGTTCCCTCG    600

TGGGTGGTGG CTCCTGAATA CATGGGGCTA CAGTGCACAG CGCATGGGCC TTAGGTCCTC    660

CAGAGCTGGC GGATGAACGA CCCTCACGAT GGCTGCTTTT GAGGGGTCAT CAGCTGTTCC    720

ACCTCCCGCA TGAACCTCAG ACACAGCTCT TCCTGCCAGG GCAGAGCCAC GCACTGCACA    780

GCCACAGGCA GACCGACACT ATTTTTCATG GCCTTCTTCA GGATGATGTC CCAGATATCC    840

CCAAAGTAGC CTTTGTAGAG TTCCATCTGG GCATCGTCCT CGGCGGTCAC AGTGGTGACA    900

GGCACCACCC CCGCAGGGAA GTCCAGGCAG TTGTAGAGAA CGGTGTAGCT GATAGCCCCT    960

GTGGCTCTGC CCGGTGTGTT CAAATCCAGA GCAGGGCCCA ACATGGGGGT CAGCAGCACA   1020

TCCAAGTTCA TCGCTTTCCA CTGGGCAATC ACAGACTGGC GATACATCTC AATCTCATGC   1080

TGCAGTTTCC ACAGCTTTTC AGCTGACCGA GGACGCATAC TGTTGAGAAA GGCTGCCAGC   1140

CGAGGAAACA GAGGCTTCAG CAGGAGGCTC AGCAGTCTTT TAAACCAGCT GGGCAGCCTC   1200

AGAATTAAGA TCAGGTCTCC CAAGCAGGGA TCCACAAAGT CACCTTTGAA GTTTTGGAGA   1260

AAACTGCGGC CACCGTCACT GAACAGGCCG CCCGCAGACA GGACCTCCAG GGCGTAGGGT   1320

ATGTTGTTGG GTAAGAAGGG AATCAGCGTG TGGCCAGCAG CCTCAAGTCT CTGCTTGGTC   1380

TCTATCAGAG CCCTCCTCAT AGCTGGGCTG GCATGGTAT  AGTTGTCAGT CTCATAGTAC   1440

CCCACACGCA GGGGTCTAGA ACTTCTATAG ACCTCCTCTC TGAAGGGCAA GGGAGGCACG   1500

GTAGGGTCCA AGGTGAACAA GTGCTCACAC AGTAGAGCTT TCAGGCATAG CGCCAGGCTC   1560

TCCACATCCC GGGCCATGGG GCCAAGAGAA AGCTGCACTG CCGTCTGTCC ATAGACACAG   1620

CCCTTCAGGC CACTCTTGCT GAGGCGGTTG CCAGTAGGCT TGAGGCCACA GATGCCGCAG   1680

AAGGCAGAAG GGAACCGGAT GCTGCCGCCA ATGTCAGTGC CTAAACCCAG AGGGGAACCT   1740

CCAGATCCAA TGAGAGCCCC CTCACCCCCT GAGGAACCTC CTGGGCTCTT GGAGGACTTC   1800

CATGGGTTCA TGGTCTGGCC AAAGAGAGGG TTACTGCAGT CAAAGCTTAA CATGGACTGG   1860

GGGACATTGG TATGCACAAA GGGCACAGCT CCCTGCAGCT TCAACACTTG CACCACCACA   1920

CAGTCAGATT CCGATGGCAT GCCCTCATTC AGGCTCAAGC CCAGTGTGGA GTCGTGGCCC   1980

TTGTAGCTGA AGCATTCCTT GAGGCTCACA GGGACACCAT AGAGCAGGCC CTGCCGTGGG   2040

GCCTGGGACA GCTGAGTCTC ACAGTCGGTC AGATAGGAGG TCACGCAGTT GGTCCCTTTG   2100

TTCACTTCCC AGGCCTTTCC CAGGTAAGTA AAGAACACAG CCTCTGGGGA CAGCTCTCCA   2160

CTCTGTAACT TCTGTACCAG TTGGAGTAGG GGCAGGGTCA GCAAGGCCTC CGAGTCCAGG   2220

TCAGGATTCT GCAGCCGGAA GCGCTGCACC GCCTTGTCCA TGGTCTCCAG GCTGGCTCGC   2280

TGCTTCTGCC GCGCCCTGGT CGCCGCGCCC CGGGCCTTCT GGCGCCCGGT CCATCGCAGG   2340

ACCACCGCCG CCGACAACAA GCTGCAGGCT AGGCAAACCC CGGAGACCCC AGACAGCGTG   2400

GTCCACACTT CGCTCAGCAC CATGATCTCC TGCAGCCGAC CGCCACCCGA GAGAACTCGG   2460

CTCGCACAAA CC                                                      2472
```

(2) INFORMATION FOR SEQ ID NO:38:

(i) SEQUENCE CHARACTERISTICS:
        (A) LENGTH: 6 amino acids
        (B) TYPE: amino acid (D) TOPOLOGY: linear (ii) MOLECULE TYPE: peptide (v) FRAGMENT TYPE: internal (xi) SEQUENCE DESCRIPTION: SEQ ID NO:38:

Pro Pro Leu Pro Xaa Arg
1               5

(2) INFORMATION FOR SEQ ID NO:39:

(i) SEQUENCE CHARACTERISTICS:
         (A) LENGTH: 1959 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (ix) FEATURE:
         (A) NAME/KEY: CDS
         (B) LOCATION: 1..1746

(xi) SEQUENCE DESCRIPTION: SEQ ID NO:39:

```
TGG GTC ATG GTG CTG AGC GAA GTG TGG ACC GCG CTG TCT GGA CTC TCC        48
Trp Val Met Val Leu Ser Glu Val Trp Thr Ala Leu Ser Gly Leu Ser
 1               5                  10                  15

GGG GTT TGC CTA GCC TGC AGC TTG CTG TCG GCG GCG GTG GTC CTG CGA        96
Gly Val Cys Leu Ala Cys Ser Leu Leu Ser Ala Ala Val Val Leu Arg
                20                  25                  30

TGG ACC AGG AGC CAG ACC GCC CGG GGC GCG GTG ACC AGG GCG CGG CAG       144
Trp Thr Arg Ser Gln Thr Ala Arg Gly Ala Val Thr Arg Ala Arg Gln
            35                  40                  45

AAG CAG CGA GCC GGC CTG GAG ACC ATG GAC AAG GCG GTG CAG CGC TTC       192
Lys Gln Arg Ala Gly Leu Glu Thr Met Asp Lys Ala Val Gln Arg Phe
        50                  55                  60

CGG CTG CAG AAT CCT GAC CTG GAT TCA GAG GCC TTG CTG GCT CTG CCC       240
Arg Leu Gln Asn Pro Asp Leu Asp Ser Glu Ala Leu Leu Ala Leu Pro
 65                  70                  75                  80

CTG CTC CAA CTG GTA CAG AAG TTA CAG AGT GGG GAA CTG TCC CCA GAA       288
Leu Leu Gln Leu Val Gln Lys Leu Gln Ser Gly Glu Leu Ser Pro Glu
                85                  90                  95

GCT GTG CTC TTT ACC TAC CTG GGA AAG GCC TGG GAA GTG AAC AAA GGG       336
Ala Val Leu Phe Thr Tyr Leu Gly Lys Ala Trp Glu Val Asn Lys Gly
               100                 105                 110

ACC AAC TGT GTG ACC TCC TAT CTG ACT GAC TGT GAG ACT CAG CTG TCC       384
Thr Asn Cys Val Thr Ser Tyr Leu Thr Asp Cys Glu Thr Gln Leu Ser
           115                 120                 125

CAG GCC CCA CGG CAG GGC CTG CTC TAT GGC GTC CCC GTG AGC CTC AAG       432
Gln Ala Pro Arg Gln Gly Leu Leu Tyr Gly Val Pro Val Ser Leu Lys
       130                 135                 140

GAA TGC TTC AGC TAC AAG GGC CAT GCT TCC ACA CTG GGC TTA AGT TTG       480
Glu Cys Phe Ser Tyr Lys Gly His Ala Ser Thr Leu Gly Leu Ser Leu
145                 150                 155                 160

AAC GAG GGT GTG ACA TCG GAG AGT GAC TGT GTG GTG GTG CAG GTA CTG       528
Asn Glu Gly Val Thr Ser Glu Ser Asp Cys Val Val Val Gln Val Leu
               165                 170                 175

AAG CTG CAG GGA GCT GTG CCC TTT GTG CAC ACC AAC GTC CCC CAG TCC       576
Lys Leu Gln Gly Ala Val Pro Phe Val His Thr Asn Val Pro Gln Ser
           180                 185                 190
```

```
ATG CTA AGC TAT GAC TGC AGT AAC CCC CTC TTT GGC CAG ACC ATG AAC        624
Met Leu Ser Tyr Asp Cys Ser Asn Pro Leu Phe Gly Gln Thr Met Asn
        195                 200                 205

CCG TGG AAG CCC TCC AAG AGT CCA GGA GGT TCC TCA GGG GGT GAG GGG        672
Pro Trp Lys Pro Ser Lys Ser Pro Gly Gly Ser Ser Gly Gly Glu Gly
    210                 215                 220

GCT CTC ATT GGA TCT GGA GGC TCC CCT CTG GGT TTA GGC ACT GAC ATC        720
Ala Leu Ile Gly Ser Gly Gly Ser Pro Leu Gly Leu Gly Thr Asp Ile
225                 230                 235                 240

GGC GGC AGC ATC CGG TTC CCT TCT GCC TTC TGT GGC ATC TGT GGC CTC        768
Gly Gly Ser Ile Arg Phe Pro Ser Ala Phe Cys Gly Ile Cys Gly Leu
            245                 250                 255

AAG CCT ACT GGG AAC CGC CTC AGC AAG AGT GGC CTG AAG AGC TGT GTT        816
Lys Pro Thr Gly Asn Arg Leu Ser Lys Ser Gly Leu Lys Ser Cys Val
                260                 265                 270

TAT GGA CAG ACA GCA GTG CAG CTT TCT GTT GGC CCC ATG GCA CGG GAT        864
Tyr Gly Gln Thr Ala Val Gln Leu Ser Val Gly Pro Met Ala Arg Asp
            275                 280                 285

GTG GAT AGC CTG GCA TTG TGC ATG AAA GCC CTA CTT TGT GAG GAT TTG        912
Val Asp Ser Leu Ala Leu Cys Met Lys Ala Leu Leu Cys Glu Asp Leu
    290                 295                 300

TTC CGC TTG GAC TCC ACC ATC CCC CCC TTG CCC TTC AGG GAG GAG ATC        960
Phe Arg Leu Asp Ser Thr Ile Pro Pro Leu Pro Phe Arg Glu Glu Ile
305                 310                 315                 320

TAC AGA AGT TCT CGA CCC CTT CGT GTG GGA TAC TAT GAA ACT GAC AAC       1008
Tyr Arg Ser Ser Arg Pro Leu Arg Val Gly Tyr Tyr Glu Thr Asp Asn
            325                 330                 335

TAC ACC ATG CCC ACT CCA GCC ATG AGG AGG GCT GTG ATG GAG ACC AAG       1056
Tyr Thr Met Pro Thr Pro Ala Met Arg Arg Ala Val Met Glu Thr Lys
                340                 345                 350

CAG AGT CTC GAG GCT GCT GGC CAC ACG CTG GTC CCC TTC TTA CCA AAC       1104
Gln Ser Leu Glu Ala Ala Gly His Thr Leu Val Pro Phe Leu Pro Asn
            355                 360                 365

AAC ATA CCT TAT GCC CTG GAG GTC CTG TCG GCA GGT GGG CTG TTC AGT       1152
Asn Ile Pro Tyr Ala Leu Glu Val Leu Ser Ala Gly Gly Leu Phe Ser
    370                 375                 380

GAT GGT GGC TGC TCT TTT CTC CAA AAC TTC AAA GGC GAC TTT GTG GAT       1200
Asp Gly Gly Cys Ser Phe Leu Gln Asn Phe Lys Gly Asp Phe Val Asp
385                 390                 395                 400

CCC TGC TTG GGG GAC CTG GTC TTA GTG CTG AAG CTG CCC AGG TGG TTT       1248
Pro Cys Leu Gly Asp Leu Val Leu Val Leu Lys Leu Pro Arg Trp Phe
            405                 410                 415

AAA AAA CTG CTG AGC TTC CTG CTG AAG CCT CTG TTT CCT CGG CTG GCA       1296
Lys Lys Leu Leu Ser Phe Leu Leu Lys Pro Leu Phe Pro Arg Leu Ala
                420                 425                 430

GCC TTT CTC AAC AGT ATG TGT CCT CGG TCA GCC GAA AAG CTG TGG GAA       1344
Ala Phe Leu Asn Ser Met Cys Pro Arg Ser Ala Glu Lys Leu Trp Glu
            435                 440                 445

CTG CAG CAT GAG ATT GAG ATG TAT CGC CAG TCC GTC ATT GCC CAG TGG       1392
Leu Gln His Glu Ile Glu Met Tyr Arg Gln Ser Val Ile Ala Gln Trp
    450                 455                 460

AAG GCA ATG AAC TTG GAC GTG GTG CTA ACC CCC ATG CTG GGT CCT GCT       1440
Lys Ala Met Asn Leu Asp Val Val Leu Thr Pro Met Leu Gly Pro Ala
465                 470                 475                 480

CTG GAT TTG AAC ACA CCG GGC AGA GCC ACA GGG GCT ATC AGC TAC ACT       1488
Leu Asp Leu Asn Thr Pro Gly Arg Ala Thr Gly Ala Ile Ser Tyr Thr
            485                 490                 495

GTT CTC TAT AAC TGC CTG GAC TTC CCT GCG GGG GTG GTG CCT GTC ACC       1536
Val Leu Tyr Asn Cys Leu Asp Phe Pro Ala Gly Val Val Pro Val Thr
```

```
                500              505              510
ACT GTG ACC GCT GAG GAC GAT GCC CAG ATG GAA CAC TAC AAA GGC TAC    1584
Thr Val Thr Ala Glu Asp Asp Ala Gln Met Glu His Tyr Lys Gly Tyr
        515                  520                  525

TTT GGG GAT ATG TGG GAC AAC ATT CTG AAG AAG GGC ATG AAA AAG GGT    1632
Phe Gly Asp Met Trp Asp Asn Ile Leu Lys Lys Gly Met Lys Lys Gly
    530                  535                  540

ATA GGC CTG CCT GTG GCT GTG CAG TGC GTG GCT CTG CCC TGG CAG GAA    1680
Ile Gly Leu Pro Val Ala Val Gln Cys Val Ala Leu Pro Trp Gln Glu
545                  550                  555                  560

GAG CTG TGT CTG CGG TTC ATG CGG GAG GTG GAA CGG CTG ATG ACC CCT    1728
Glu Leu Cys Leu Arg Phe Met Arg Glu Val Glu Arg Leu Met Thr Pro
                565                  570                  575

GAA AAG CGG CCA TCT TGAGGGTCAT TCATCTGCCC AGCTCTGGAG GACCTAAGGC    1783
Glu Lys Arg Pro Ser
            580

CCATGCGCTC TGCACTGCAG CCCCATCTAT TCAGGATCCT GCCACCCATG AGGAGATGCC    1843

CAGCACGGGA AGAGGCAACC ACCTGCCCTC CCCTGGACTC CTACAGAAAC CCAGGACATG    1903

CCCTCCATAA CCAAGTCTGG ACCAGCTCCC CCGGAATTCC TGCAGCCCGG GGGATC        1959

(2) INFORMATION FOR SEQ ID NO:40:

(i) SEQUENCE CHARACTERISTICS:
        (A) LENGTH: 581 amino acids
        (B) TYPE: amino acid
        (D) TOPOLOGY: linear (ii) MOLECULE TYPE: protein (xi) SEQUENCE DESCRIPTION: SEQ ID NO:40:

Trp Val Met Val Leu Ser Glu Val Trp Thr Ala Leu Ser Gly Leu Ser
 1               5                  10                  15

Gly Val Cys Leu Ala Cys Ser Leu Leu Ser Ala Ala Val Val Leu Arg
            20                  25                  30

Trp Thr Arg Ser Gln Thr Ala Arg Gly Ala Val Thr Arg Ala Arg Gln
        35                  40                  45

Lys Gln Arg Ala Gly Leu Glu Thr Met Asp Lys Ala Val Gln Arg Phe
    50                  55                  60

Arg Leu Gln Asn Pro Asp Leu Asp Ser Glu Ala Leu Leu Ala Leu Pro
65                  70                  75                  80

Leu Leu Gln Leu Val Gln Lys Leu Gln Ser Gly Glu Leu Ser Pro Glu
                85                  90                  95

Ala Val Leu Phe Thr Tyr Leu Gly Lys Ala Trp Glu Val Asn Lys Gly
            100                 105                 110

Thr Asn Cys Val Thr Ser Tyr Leu Thr Asp Cys Glu Thr Gln Leu Ser
        115                 120                 125

Gln Ala Pro Arg Gln Gly Leu Leu Tyr Gly Val Pro Val Ser Leu Lys
    130                 135                 140

Glu Cys Phe Ser Tyr Lys Gly His Ala Ser Thr Leu Gly Leu Ser Leu
145                 150                 155                 160

Asn Glu Gly Val Thr Ser Glu Ser Asp Cys Val Val Val Gln Val Leu
                165                 170                 175

Lys Leu Gln Gly Ala Val Pro Phe Val His Thr Asn Val Pro Gln Ser
            180                 185                 190

Met Leu Ser Tyr Asp Cys Ser Asn Pro Leu Phe Gly Gln Thr Met Asn
        195                 200                 205
```

```
Pro Trp Lys Pro Ser Lys Ser Pro Gly Gly Ser Ser Gly Gly Glu Gly
    210                 215                 220

Ala Leu Ile Gly Ser Gly Gly Ser Pro Leu Gly Leu Gly Thr Asp Ile
225                 230                 235                 240

Gly Gly Ser Ile Arg Phe Pro Ser Ala Phe Cys Gly Ile Cys Gly Leu
                245                 250                 255

Lys Pro Thr Gly Asn Arg Leu Ser Lys Ser Gly Leu Lys Ser Cys Val
                260                 265                 270

Tyr Gly Gln Thr Ala Val Gln Leu Ser Val Gly Pro Met Ala Arg Asp
                275                 280                 285

Val Asp Ser Leu Ala Leu Cys Met Lys Ala Leu Leu Cys Glu Asp Leu
    290                 295                 300

Phe Arg Leu Asp Ser Thr Ile Pro Pro Leu Pro Phe Arg Glu Glu Ile
305                 310                 315                 320

Tyr Arg Ser Ser Arg Pro Leu Arg Val Gly Tyr Tyr Glu Thr Asp Asn
                325                 330                 335

Tyr Thr Met Pro Thr Pro Ala Met Arg Arg Ala Val Met Glu Thr Lys
                340                 345                 350

Gln Ser Leu Glu Ala Ala Gly His Thr Leu Val Pro Phe Leu Pro Asn
    355                 360                 365

Asn Ile Pro Tyr Ala Leu Glu Val Leu Ser Ala Gly Gly Leu Phe Ser
370                 375                 380

Asp Gly Gly Cys Ser Phe Leu Gln Asn Phe Lys Gly Asp Phe Val Asp
385                 390                 395                 400

Pro Cys Leu Gly Asp Leu Val Leu Val Leu Lys Leu Pro Arg Trp Phe
                405                 410                 415

Lys Lys Leu Leu Ser Phe Leu Leu Lys Pro Leu Phe Pro Arg Leu Ala
                420                 425                 430

Ala Phe Leu Asn Ser Met Cys Pro Arg Ser Ala Glu Lys Leu Trp Glu
                435                 440                 445

Leu Gln His Glu Ile Glu Met Tyr Arg Gln Ser Val Ile Ala Gln Trp
    450                 455                 460

Lys Ala Met Asn Leu Asp Val Val Leu Thr Pro Met Leu Gly Pro Ala
465                 470                 475                 480

Leu Asp Leu Asn Thr Pro Gly Arg Ala Thr Gly Ala Ile Ser Tyr Thr
                485                 490                 495

Val Leu Tyr Asn Cys Leu Asp Phe Pro Ala Gly Val Val Pro Val Thr
                500                 505                 510

Thr Val Thr Ala Glu Asp Asp Ala Gln Met Glu His Tyr Lys Gly Tyr
    515                 520                 525

Phe Gly Asp Met Trp Asp Asn Ile Leu Lys Lys Gly Met Lys Lys Gly
530                 535                 540

Ile Gly Leu Pro Val Ala Val Gln Cys Val Ala Leu Pro Trp Gln Glu
545                 550                 555                 560

Glu Leu Cys Leu Arg Phe Met Arg Glu Val Glu Arg Leu Met Thr Pro
                565                 570                 575

Glu Lys Arg Pro Ser
                580

(2) INFORMATION FOR SEQ ID NO:41:

(i) SEQUENCE CHARACTERISTICS:
        (A) LENGTH: 1959 base pairs
        (B) TYPE: nucleic acid
        (C) STRANDEDNESS: double
```

(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:41:

```
GATCCCCCGG GCTGCAGGAA TTCCGGGGGA GCTGGTCCAG ACTTGGTTAT GGAGGGCATG      60

TCCTGGGTTT CTGTAGGAGT CCAGGGGAGG GCAGGTGGTT GCCTCTTCCC GTGCTGGGCA     120

TCTCCTCATG GGTGGCAGGA TCCTGAATAG ATGGGGCTGC AGTGCAGAGC GCATGGGCCT     180

TAGGTCCTCC AGAGCTGGGC AGATGAATGA CCCTCAAGAT GGCCGCTTTT CAGGGGTCAT     240

CAGCCGTTCC ACCTCCCGCA TGAACCGCAG ACACAGCTCT TCCTGCCAGG GCAGAGCCAC     300

GCACTGCACA GCCACAGGCA GGCCTATACC CTTTTTCATG CCCTTCTTCA GAATGTTGTC     360

CCACATATCC CCAAAGTAGC CTTTGTAGTG TTCCATCTGG GCATCGTCCT CAGCGGTCAC     420

AGTGGTGACA GCACCACCCC CCGCAGGGAA GTCCAGGCAG TTATAGAGAA CAGTGTAGCT     480

GATAGCCCCT GTGGCTCTGC CCGGTGTGTT CAAATCCAGA GCAGGACCCA GCATGGGGGT     540

TAGCACCACG TCCAAGTTCA TTGCCTTCCA CTGGGCAATG ACGGACTGGC GATACATCTC     600

AATCTCATGC TGCAGTTCCC ACAGCTTTTC GGCTGACCGA GGACACATAC TGTTGAGAAA     660

GGCTGCCAGC CGAGGAAACA GAGGCTTCAG CAGGAAGCTC AGCAGTTTTT TAAACCACCT     720

GGGCAGCTTC AGCACTAAGA CCAGGTCCCC CAAGCAGGGA TCCACAAAGT CGCCTTTGAA     780

GTTTTGGAGA AAAGAGCAGC CACCATCACT GAACAGCCCA CCTGCCGACA GGACCTCCAG     840

GGCATAAGGT ATGTTGTTTG GTAAGAAGGG GACCAGCGTG TGGCCAGCAG CCTCGAGACT     900

CTGCTTGGTC TCCATCACAG CCCTCCTCAT GGCTGGAGTG GGCATGGTGT AGTTGTCAGT     960

TTCATAGTAT CCCACACGAA GGGGTCGAGA ACTTCTGTAG ATCTCCTCCC TGAAGGGCAA    1020

GGGGGGGATG GTGGAGTCCA AGCGGAACAA ATCCTCACAA AGTAGGGCTT TCATGCACAA    1080

TGCCAGGCTA TCCACATCCC GTGCCATGGG GCCAACAGAA AGCTGCACTG CTGTCTGTCC    1140

ATAAACACAG CTCTTCAGGC CACTCTTGCT GAGGCGGTTC CCAGTAGGCT TGAGGCCACA    1200

GATGCCACAG AAGGCAGAAG GGAACCGGAT GCTGCCGCCG ATGTCAGTGC CTAAACCCAG    1260

AGGGGAGCCT CCAGATCCAA TGAGAGCCCC CTCACCCCCT GAGGAACCTC CTGGACTCTT    1320

GGAGGGCTTC CACGGGTTCA TGGTCTGGCC AAAGAGGGGG TTACTGCAGT CATAGCTTAG    1380

CATGGACTGG GGGACGTTGG TGTGCACAAA GGGCACAGCT CCCTGCAGCT TCAGTACCTG    1440

CACCACCACA CAGTCACTCT CCGATGTCAC ACCCTCGTTC AAACTTAAGC CCAGTGTGGA    1500

AGCATGGCCC TTGTAGCTGA AGCATTCCTT GAGGCTCACG GGGACGCCAT AGAGCAGGCC    1560

CTGCCGTGGG GCCTGGGACA GCTGAGTCTC ACAGTCAGTC AGATAGGAGG TCACACAGTT    1620

GGTCCCTTTG TTCACTTCCC AGGCCTTTCC CAGGTAGGTA AAGAGCACAG CTTCTGGGGA    1680

CAGTTCCCCA CTCTGTAACT TCTGTACCAG TTGGAGCAGG GGCAGAGCCA GCAAGGCCTC    1740

TGAATCCAGG TCAGGATTCT GCAGCCGGAA GCGCTGCACC GCCTTGTCCA TGGTCTCCAG    1800

GCCGGCTCGC TGCTTCTGCC GCGCCCTGGT CACCGCGCCC CGGGCGGTCT GGCTCCTGGT    1860

CCATCGCAGG ACCACCGCCG CCGACAGCAA GCTGCAGGCT AGGCAAACCC CGGAGAGTCC    1920

AGACAGCGCG GTCCACACTT CGCTCAGCAC CATGACCCA                           1959
```

(2) INFORMATION FOR SEQ ID NO:42:

(i) SEQUENCE CHARACTERISTICS:
    (A) LENGTH: 2045 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (ix) FEATURE:
    (A) NAME/KEY: CDS
    (B) LOCATION: 3..1775

(xi) SEQUENCE DESCRIPTION: SEQ ID NO:42:

```
TG CCG GGC GGT AGG CAG CAG CAG GCT GAA GGG ATC ATG GTG CAG TAC          47
   Pro Gly Gly Arg Gln Gln Gln Ala Glu Gly Ile Met Val Gln Tyr
     1               5                  10                  15

GAG CTG TGG GCC GCG CTG CCT GGC GCC TCC GGG GTC GCC CTG GCC TGC          95
Glu Leu Trp Ala Ala Leu Pro Gly Ala Ser Gly Val Ala Leu Ala Cys
                20                  25                  30

TGC TTC GTG GCG GCG GCC GTG GCC CTG CGC TGG TCC GGG CGC CGG ACG         143
Cys Phe Val Ala Ala Ala Val Ala Leu Arg Trp Ser Gly Arg Arg Thr
                    35                  40                  45

GCG CGG GGC GCG GTG GTC CGG GCG CGA CAG AAG CAG CGA GCG GGC CTG         191
Ala Arg Gly Ala Val Val Arg Ala Arg Gln Lys Gln Arg Ala Gly Leu
                        50                  55                  60

GAG AAC ATG GAC AGG GCG GCG CAG CGC TTC CGG CTC CAG AAC CCA GAC         239
Glu Asn Met Asp Arg Ala Ala Gln Arg Phe Arg Leu Gln Asn Pro Asp
 65                  70                  75

CTG GAC TCA GAG GCG CTG CTA GCC CTG CCC CTG CCT CAG CTG GTG CAG         287
Leu Asp Ser Glu Ala Leu Leu Ala Leu Pro Leu Pro Gln Leu Val Gln
 80                  85                  90                  95

AAG TTA CAC AGT AGA GAG CTG GCC CCT GAG GCC GTG CTC TTC ACC TAT         335
Lys Leu His Ser Arg Glu Leu Ala Pro Glu Ala Val Leu Phe Thr Tyr
                    100                 105                 110

GTG GGA AAG GCC TGG GAA GTG AAC AAA GGG ACC AAC TGT GTG ACC TCC         383
Val Gly Lys Ala Trp Glu Val Asn Lys Gly Thr Asn Cys Val Thr Ser
                115                 120                 125

TAT CTG GCT GAC TGT GAG ACT CAG CTG TCT CAG GCC CCA AGG CAG GGC         431
Tyr Leu Ala Asp Cys Glu Thr Gln Leu Ser Gln Ala Pro Arg Gln Gly
            130                 135                 140

CTG CTC TAT GGC GTC CCT GTG AGC CTC AAG GAG TGC TTC ACC TAC AAG         479
Leu Leu Tyr Gly Val Pro Val Ser Leu Lys Glu Cys Phe Thr Tyr Lys
        145                 150                 155

GGC CAG GAC TCC ACG CTG GGC TTG AGC CTG AAT GAA GGG GTG CCG GCG         527
Gly Gln Asp Ser Thr Leu Gly Leu Ser Leu Asn Glu Gly Val Pro Ala
160                 165                 170                 175

GAG TGC GAC AGC GTA GTG GTG CAT GTG CTG AAG CTG CAG GGT GCC GTG         575
Glu Cys Asp Ser Val Val Val His Val Leu Lys Leu Gln Gly Ala Val
                    180                 185                 190

CCC TTC GTG CAC ACC AAT GTT CCA CAG TCC ATG TTC AGC TAT GAC TGC         623
Pro Phe Val His Thr Asn Val Pro Gln Ser Met Phe Ser Tyr Asp Cys
                195                 200                 205

AGT AAC CCC CTC TTT GGC CAG ACC GTG AAC CCA TGG AAG TCC TCC AAA         671
Ser Asn Pro Leu Phe Gly Gln Thr Val Asn Pro Trp Lys Ser Ser Lys
            210                 215                 220

AGC CCA GGG GGC TCC TCA GGG GGT GAA GGG GCC CTC ATC GGG TCT GGA         719
Ser Pro Gly Gly Ser Ser Gly Gly Glu Gly Ala Leu Ile Gly Ser Gly
        225                 230                 235

GGC TCC CCC CTG GGC TTA GGC ACT GAT ATC GGA GGC AGC ATC CGC TTC         767
```

-continued

```
Gly Ser Pro Leu Gly Leu Gly Thr Asp Ile Gly Gly Ser Ile Arg Phe
240                 245                 250                 255

CCC TCC TCC TTC TGC GGC ATC TGC GGC CTC AAG CCC ACA GGG AAC CGC       815
Pro Ser Ser Phe Cys Gly Ile Cys Gly Leu Lys Pro Thr Gly Asn Arg
                    260                 265                 270

CTC AGC AAG AGT GGC CTG AAG GGC TGT GTC TAT GGA CAG GAG GCA GTG       863
Leu Ser Lys Ser Gly Leu Lys Gly Cys Val Tyr Gly Gln Glu Ala Val
                275                 280                 285

CGT CTC TCC GTG GGC CCC ATG GCC CGG GAC GTG GAG AGC CTG GCA CTG       911
Arg Leu Ser Val Gly Pro Met Ala Arg Asp Val Glu Ser Leu Ala Leu
            290                 295                 300

TGC CTG CGA GCC CTG CTG TGC GAG GAC ATG TTC CGC TTG GAC CCC ACT       959
Cys Leu Arg Ala Leu Leu Cys Glu Asp Met Phe Arg Leu Asp Pro Thr
        305                 310                 315

GTG CCT CCC TTG CCC TTC AGA GAA GAG GTC TAC ACC AGC TCT CAG CCC      1007
Val Pro Pro Leu Pro Phe Arg Glu Glu Val Tyr Thr Ser Ser Gln Pro
320                 325                 330                 335

CTG CGT GTG GGG TAC TAT GAG ACT GAC AAC TAT ACC ATG CCC TCC CCG      1055
Leu Arg Val Gly Tyr Tyr Glu Thr Asp Asn Tyr Thr Met Pro Ser Pro
                    340                 345                 350

GCC ATG AGG CGG GCC GTG CTG GAG ACC AAA CAG AGC CTT GAG GCT GCG      1103
Ala Met Arg Arg Ala Val Leu Glu Thr Lys Gln Ser Leu Glu Ala Ala
                355                 360                 365

GGG CAC ACG CTG GTT CCC TTC TTG CCA AGC AAC ATA CCC CAT GCT CTG      1151
Gly His Thr Leu Val Pro Phe Leu Pro Ser Asn Ile Pro His Ala Leu
            370                 375                 380

GAG ACC CTG TCA ACA GGT GGG CTC TTC AGT GAT GGT GGC CAC ACC TTC      1199
Glu Thr Leu Ser Thr Gly Gly Leu Phe Ser Asp Gly Gly His Thr Phe
        385                 390                 395

CTA CAG AAC TTC AAA GGT GAT TTC GTG GAC CCC TGC CTG GGG GAC CTG      1247
Leu Gln Asn Phe Lys Gly Asp Phe Val Asp Pro Cys Leu Gly Asp Leu
400                 405                 410                 415

GTC TCA ATT CTG AAG CTT CCC CAA TGG CTT AAA GGA CTG CTG GCC TTC      1295
Val Ser Ile Leu Lys Leu Pro Gln Trp Leu Lys Gly Leu Leu Ala Phe
                    420                 425                 430

CTG GTG AAG CCT CTG CTG CCA AGG CTG TCA GCT TTC CTC AGC AAC ATG      1343
Leu Val Lys Pro Leu Leu Pro Arg Leu Ser Ala Phe Leu Ser Asn Met
                435                 440                 445

AAG TCT CGT TCG GCT GGA AAA CTC TGG GAA CTG CAG CAC GAG ATC GAG      1391
Lys Ser Arg Ser Ala Gly Lys Leu Trp Glu Leu Gln His Glu Ile Glu
            450                 455                 460

GTG TAC CGC AAA ACC GTG ATT GCC CAG TGG AGG GCG CTG GAC CTG GAT      1439
Val Tyr Arg Lys Thr Val Ile Ala Gln Trp Arg Ala Leu Asp Leu Asp
        465                 470                 475

GTG GTG CTG ACC CCC ATG CTG GCC CCT GCT CTG GAC TTG AAT GCC CCA      1487
Val Val Leu Thr Pro Met Leu Ala Pro Ala Leu Asp Leu Asn Ala Pro
480                 485                 490                 495

GGC AGG GCC ACA GGG GCC GTC AGC TAC ACT ATG CTG TAC AAC TGC CTG      1535
Gly Arg Ala Thr Gly Ala Val Ser Tyr Thr Met Leu Tyr Asn Cys Leu
                    500                 505                 510

GAC TTC CCT GCA GGG GTG GTG CCT GTC ACC ACG GTG ACT GCT GAG GAC      1583
Asp Phe Pro Ala Gly Val Val Pro Val Thr Thr Val Thr Ala Glu Asp
                515                 520                 525

GAG GCC CAG ATG GAA CAT TAC AGG GGC TAC TTT GGG GAT ATC TGG GAC      1631
Glu Ala Gln Met Glu His Tyr Arg Gly Tyr Phe Gly Asp Ile Trp Asp
            530                 535                 540

AAG ATG CTG CAG AAG GGC ATG AAG AAG AGT GTG GGC CTG CCG GTG GCC      1679
Lys Met Leu Gln Lys Gly Met Lys Lys Ser Val Gly Leu Pro Val Ala
        545                 550                 555
```

```
GTG CAG TGT GTG GCT CTG CCC TGG CAA GAA GAG TTG TGT CTG CGG TTC    1727
Val Gln Cys Val Ala Leu Pro Trp Gln Glu Glu Leu Cys Leu Arg Phe
560                 565                 570                 575

ATG CGG GAG GTG GAG CGA CTG ATG ACC CCT GAA AAG CAG TCA TCC TGATGGCT1782
Met Arg Glu Val Glu Arg Leu Met Thr Pro Glu Lys Gln Ser Ser
                580                 585                 590

GGCTCCAGAG GACCTGAGAC TCACACTCTC TGCAGCCCAG CCTAGTCAGG GCACAGCTGC    1842

CCTGCTGCCA CAGCAAGGAA ATGTCCTGCA TGGGGCAGAG GCTTCCGTGT CCTCTCCCCC    1902

AACCCCCTGC AAGAAGCGCC GACTCCCTGA GTCTGGACCT CCATCCCTGC TCTGGTCCCC    1962

TCTCTTCGTC CTGATCCCTC CACCCCCATG TGGCAGCCCA TGGGTATGAC ATAGGCCAAG    2022

GCCCAACTAA CAGCCCCGGA ATT                                            2045

(2) INFORMATION FOR SEQ ID NO:43:

(i) SEQUENCE CHARACTERISTICS:
        (A) LENGTH: 590 amino acids
        (B) TYPE: amino acid
        (D) TOPOLOGY: linear (ii) MOLECULE TYPE: protein (xi) SEQUENCE DESCRIPTION: SEQ ID NO:43:

Pro Gly Gly Arg Gln Gln Gln Ala Glu Gly Ile Met Val Gln Tyr Glu
1               5                   10                  15

Leu Trp Ala Ala Leu Pro Gly Ala Ser Gly Val Ala Leu Ala Cys Cys
                20                  25                  30

Phe Val Ala Ala Val Ala Leu Arg Trp Ser Gly Arg Arg Thr Ala
            35                  40                  45

Arg Gly Ala Val Val Arg Ala Arg Gln Lys Gln Arg Ala Gly Leu Glu
        50                  55                  60

Asn Met Asp Arg Ala Ala Gln Arg Phe Arg Leu Gln Asn Pro Asp Leu
65                  70                  75                  80

Asp Ser Glu Ala Leu Leu Ala Leu Pro Leu Pro Gln Leu Val Gln Lys
                85                  90                  95

Leu His Ser Arg Glu Leu Ala Pro Glu Ala Val Leu Phe Thr Tyr Val
                100                 105                 110

Gly Lys Ala Trp Glu Val Asn Lys Gly Thr Asn Cys Val Thr Ser Tyr
            115                 120                 125

Leu Ala Asp Cys Glu Thr Gln Leu Ser Gln Ala Pro Arg Gln Gly Leu
        130                 135                 140

Leu Tyr Gly Val Pro Val Ser Leu Lys Glu Cys Phe Thr Tyr Lys Gly
145                 150                 155                 160

Gln Asp Ser Thr Leu Gly Leu Ser Leu Asn Glu Gly Val Pro Ala Glu
                165                 170                 175

Cys Asp Ser Val Val His Val Leu Lys Leu Gln Gly Ala Val Pro
                180                 185                 190

Phe Val His Thr Asn Val Pro Gln Ser Met Phe Ser Tyr Asp Cys Ser
            195                 200                 205

Asn Pro Leu Phe Gly Gln Thr Val Asn Pro Trp Lys Ser Ser Lys Ser
        210                 215                 220

Pro Gly Gly Ser Ser Gly Gly Glu Gly Ala Leu Ile Gly Ser Gly Gly
225                 230                 235                 240

Ser Pro Leu Gly Leu Gly Thr Asp Ile Gly Gly Ser Ile Arg Phe Pro
                245                 250                 255

Ser Ser Phe Cys Gly Ile Cys Gly Leu Lys Pro Thr Gly Asn Arg Leu
```

```
                260                 265                 270
Ser Lys Ser Gly Leu Lys Gly Cys Val Tyr Gly Gln Glu Ala Val Arg
            275                 280                 285

Leu Ser Val Gly Pro Met Ala Arg Asp Val Glu Ser Leu Ala Leu Cys
    290                 295                 300

Leu Arg Ala Leu Leu Cys Glu Asp Met Phe Arg Leu Asp Pro Thr Val
305                 310                 315                 320

Pro Pro Leu Pro Phe Arg Glu Glu Val Tyr Thr Ser Ser Gln Pro Leu
                325                 330                 335

Arg Val Gly Tyr Tyr Glu Thr Asp Asn Tyr Thr Met Pro Ser Pro Ala
                340                 345                 350

Met Arg Arg Ala Val Leu Glu Thr Lys Gln Ser Leu Glu Ala Ala Gly
            355                 360                 365

His Thr Leu Val Pro Phe Leu Pro Ser Asn Ile Pro His Ala Leu Glu
        370                 375                 380

Thr Leu Ser Thr Gly Gly Leu Phe Ser Asp Gly Gly His Thr Phe Leu
385                 390                 395                 400

Gln Asn Phe Lys Gly Asp Phe Val Asp Pro Cys Leu Gly Asp Leu Val
                405                 410                 415

Ser Ile Leu Lys Leu Pro Gln Trp Leu Lys Gly Leu Leu Ala Phe Leu
            420                 425                 430

Val Lys Pro Leu Leu Pro Arg Leu Ser Ala Phe Leu Ser Asn Met Lys
        435                 440                 445

Ser Arg Ser Ala Gly Lys Leu Trp Glu Leu Gln His Glu Ile Glu Val
    450                 455                 460

Tyr Arg Lys Thr Val Ile Ala Gln Trp Arg Ala Leu Asp Leu Asp Val
465                 470                 475                 480

Val Leu Thr Pro Met Leu Ala Pro Ala Leu Asp Leu Asn Ala Pro Gly
                485                 490                 495

Arg Ala Thr Gly Ala Val Ser Tyr Thr Met Leu Tyr Asn Cys Leu Asp
                500                 505                 510

Phe Pro Ala Gly Val Val Pro Val Thr Thr Val Thr Ala Glu Asp Glu
            515                 520                 525

Ala Gln Met Glu His Tyr Arg Gly Tyr Phe Gly Asp Ile Trp Asp Lys
        530                 535                 540

Met Leu Gln Lys Gly Met Lys Lys Ser Val Gly Leu Pro Val Ala Val
545                 550                 555                 560

Gln Cys Val Ala Leu Pro Trp Gln Glu Glu Leu Cys Leu Arg Phe Met
                565                 570                 575

Arg Glu Val Glu Arg Leu Met Thr Pro Glu Lys Gln Ser Ser
            580                 585                 590

(2) INFORMATION FOR SEQ ID NO:44:

(i) SEQUENCE CHARACTERISTICS:
        (A) LENGTH: 2045 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:44:
```

-continued

```
AATTCCGGGG CTGTTAGTTG GGCCTTGGCC TATGTCATAC CCATGGGCTG CCACATGGGG        60

GTGGAGGGAT CAGGACGAAG AGAGGGGACC AGAGCAGGGA TGGAGGTCCA GACTCAGGGA       120

GTCGGCGCTT CTTGCAGGGG GTTGGGGGAG AGGACACGGA AGCCTCTGCC CCATGCAGGA       180

CATTTCCTTG CTGTGGCAGC AGGGCAGCTG TGCCCTGACT AGGCTGGGCT GCAGAGAGTG       240

TGAGTCTCAG GTCCTCTGGA GCCAGAGCCA TCAGGATGAC TGCTTTTCAG GGGTCATCAG       300

TCGCTCCACC TCCCGCATGA ACCGCAGACA CAACTCTTCT TGCCAGGGCA GAGCCACACA       360

CTGCACGGCC ACCGGCAGCC CCACACTCTT CTTCATGCCC TTCTGCAGCA TCTTGTCCCA       420

GATATCCCCA AAGTAGCCCC TGTAATGTTC CATCTGGGCC TCGTCCTCAG CAGTCACCGT       480

GGTGACAGGC ACCACCCCTG CAGGGAAGTC CAGGCAGTTG TACAGCATAG TGTAGCTGAC       540

GGCCCCTGTG GCCCTGCCTG GGCATTCAA GTCCAGAGCA GGGGCCAGCA TGGGGGTCAG        600

CACCACATCC AGGTCCAGCG CCCTCCACTG GGCAATCACG GTTTTGCGGT ACACCTCGAT       660

CTCGTGCTGC AGTTCCCAGA GTTTTCCAGC CGAACGAGAC TTCATGTTGC TGAGGAAAGC       720

TGACAGCCTT GGCAGCAGAG GCTTCACCAG GAAGGCCAGC AGTCCTTTAA GCCATTGGGG       780

AAGCTTCAGA ATTGAGACCA GGTCCCCCAG GCAGGGGTCC ACGAAATCAC CTTTGAAGTT       840

CTGTAGGAAG GTGTGGCCAC CATCACTGAA GAGCCCACCT GTTGACAGGG TCTCCAGAGC       900

ATGGGGTATG TTGCTTGGCA AGAAGGGAAC CAGCGTGTGC CCCGCAGCCT CAAGGCTCTG       960

TTTGGTCTCC AGCACGGCCC GCCTCATGGC CGGGGAGGGC ATGGTATAGT TGTCAGTCTC      1020

ATAGTACCCC ACACGCAGGG GCTGAGAGCT GGTGTAGACC TCTTCTCTGA AGGGCAAGGG      1080

AGGCACAGTG GGGTCCAAGC GGAACATGTC CTCGCACAGC AGGGCTCGCA GGCACAGTGC      1140

CAGGCTCTCC ACGTCCCGGG CCATGGGGCC CACGGAGAGA CGCACTGCCT CCTGTCCATA      1200

GACACAGCCC TTCAGGCCAC TCTTGCTGAG GCGGTTCCCT GTGGGCTTGA GGCCGCAGAT      1260

GCCGCAGAAG GAGGAGGGGA AGCGGATGCT GCCTCCGATA TCAGTGCCTA AGCCCAGGGG      1320

GGAGCCTCCA GACCCGATGA GGGCCCCTTC ACCCCTGAG GAGCCCCCTG GCTTTTGGA       1380

GGACTTCCAT GGGTTCACGG TCTGGCCAAA GAGGGGGTTA CTGCAGTCAT AGCTGAACAT      1440

GGACTGTGGA ACATTGGTGT GCACGAAGGG CACGGCACCC TGCAGCTTCA GCACATGCAC      1500

CACTACGCTG TCGCACTCCG CCGGCACCCC TTCATTCAGG CTCAAGCCCA GCGTGGAGTC      1560

CTGGCCCTTG TAGGTGAAGC ACTCCTTGAG GCTCACAGGG ACGCCATAGA GCAGGCCCTG      1620

CCTTGGGGCC TGAGACAGCT GAGTCTCACA GTCAGCCAGA TAGGAGGTCA CACAGTTGGT      1680

CCCTTTGTTC ACTTCCCAGG CCTTTCCCAC ATAGGTGAAG AGCACGGCCT CAGGGGCCAG      1740

CTCTCTACTG TGTAACTTCT GCACCAGCTG AGGCAGGGGC AGGGCTAGCA GCGCCTCTGA      1800

GTCCAGGTCT GGGTTCTGGA GCCGGAAGCG CTGCGCCGCC CTGTCCATGT TCTCCAGGCC      1860

CGCTCGCTGC TTCTGTCGCG CCCGGACCAC CGCGCCCCGC GCCGTCCGGC GCCCGGACCA      1920

GCGCAGGGCC ACGGCCGCCG CCACGAAGCA GCAGGCCAGG GCGACCCCGG AGGCGCCAGG      1980

CAGCGCGGCC ACACAGCTCGT ACTGCACCAT GATCCCTTCA GCCTGCTGCT GCCTACCGCC     2040

CGGCA                                                                 2045
```

(2) INFORMATION FOR SEQ ID NO:45:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:45:

GCGGTACCAT GCGATGGACC GGGCGC                                              26

(2) INFORMATION FOR SEQ ID NO:46:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:46:

GGTCTGGCCA AAGAGAGG                                                       18

(2) INFORMATION FOR SEQ ID NO:47:

(i) SEQUENCE CHARACTERISTICS:
            (A) LENGTH: 32 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:47:

Gly Gly Ser Ser Gly Gly Glu Gly Ala Leu Ile Ala Gly Gly Ser
1               5                  10                  15

Leu Leu Gly Ile Gly Ser Asp Val Ala Gly Ser Ile Arg Leu Pro Ser
            20                  25                  30

(2) INFORMATION FOR SEQ ID NO:48:

(i) SEQUENCE CHARACTERISTICS:
            (A) LENGTH: 32 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:48:

Gly Gly Ser Ser Gly Gly Glu Gly Ala Leu Ile Gly Ala Gly Gly Ser
1               5                  10                  15

Leu Ile Gly Ile Gly Thr Asp Val Gly Gly Ser Val Arg Ile Pro Cys
            20                  25                  30

(2) INFORMATION FOR SEQ ID NO:49:

(i) SEQUENCE CHARACTERISTICS:
            (A) LENGTH: 32 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:49:

```
Gly Gly Ser Ser Gly Gly Glu Ser Ala Leu Ile Ser Ala Asp Gly Ser
1               5                   10                  15
Leu Leu Gly Ile Gly Gly Asp Val Gly Gly Ser Ile Arg Ile Pro Cys
            20                  25                  30
```

(2) INFORMATION FOR SEQ ID NO:50:

(i) SEQUENCE CHARACTERISTICS:
        (A) LENGTH: 32 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:50:

```
Gly Gly Ser Ser Gly Gly Glu Gly Ser Leu Ile Gly Ala His Gly Ser
1               5                   10                  15
Leu Leu Gly Leu Gly Thr Asp Ile Gly Gly Ser Ile Arg Ile Pro Ser
            20                  25                  30
```

(2) INFORMATION FOR SEQ ID NO:51:

(i) SEQUENCE CHARACTERISTICS:
        (A) LENGTH: 32 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:51:

```
Gly Gly Ser Ser Gly Gly Glu Gly Ala Ile Val Gly Ile Arg Gly Gly
1               5                   10                  15
Val Ile Gly Val Gly Thr Asp Ile Gly Gly Ser Ile Asp Val Pro Ala
            20                  25                  30
```

(2) INFORMATION FOR SEQ ID NO:52:

(i) SEQUENCE CHARACTERISTICS:
        (A) LENGTH: 32 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:52:

```
Gly Gly Ser Ser Gly Gly Val Ala Ala Ala Val Ala Ser Arg Leu Met
1               5                   10                  15
Leu Gly Gly Ile Gly Thr Asp Thr Gly Ala Ser Val Arg Leu Pro Ala
            20                  25                  30
```

(2) INFORMATION FOR SEQ ID NO:53:

(i) SEQUENCE CHARACTERISTICS:
        (A) LENGTH: 32 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:53:

```
Gly Gly Ser Ser Gly Gly Val Ala Ala Val Ala Ser Gly Ile Val
1               5                   10                  15

Pro Leu Ser Val Gly Thr Asp Thr Gly Gly Ser Ile Arg Ile Pro Ala
            20                  25                  30
```

(2) INFORMATION FOR SEQ ID NO:54:

(i) SEQUENCE CHARACTERISTICS:
        (A) LENGTH: 819 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:54:

```
CCAGGAGGTT CCTCAGGGGG TGAGGGGGCT CTCATTGGAT CTGGAGGTTC CCCTCTGGGT      60
TTAGGCACTG ACATTGGCGG CAGCATCCGG TTCCCTTCTG CCTTCTGCGG CATCTGTGGC     120
CTCAAGCCTA CTGGCAACCG CCTCAGCAAG AGTGGCCTGA AGGGCTGTGT CTATGGACAG     180
ACGGCAGTGC AGCTTTCTCT TGGCCCCATG GCCCGGGATG TGGAGAGCCT GGCGCTATGC     240
CTGAAAGCTC TACTGTGTGA GCACTTGTTC ACCTTGGACC CTACCGTGCC TCCCTTTCCC     300
TTCAGAGAGG AGGTCTATAG AAGTTCTAGA CCCCTGCGTG TGGGGTACTA TGAGACTGAC     360
AACTATACCA TGCCCAGCCC AGCTATGAGG AGGGCTCTGA TAGAGACCAA GCAGAGACTT     420
GAGGCTGCTG GCCACACGCT GATTCCCTTC TTACCCAACA ACATACCCTA CGCCCTGGAG     480
GTCCTGTCTG CGGGCGGCCT GTTCAGTGAC GGTGGCCGCA GTTTTCTCCA AAACTTCAAA     540
GGTGACTTTG TGGATCCCTG CTTGGGAGAC CTGATCTTAA TTCTGAGGCT GCCCAGCTGG     600
TTTAAAAGAC TGCTGAGCCT CCTGCTGAAG CCTCTGTTTC CTCGGCTGGC AGCCTTTCTC     660
AACAGTATGC GTCCTCGGTC AGCTGAAAAG CTGTGGAAAC TGCAGCATGA GATTGAGATG     720
TATCGCCAGT CTGTGATTGC CCAGTGGAAA GCGATGAACT TGGATGTGCT GCTGACCCCN     780
ATGYTNGGNC CNGCNYTNGA YYTNAAYACN CCNGGNMGN                            819
```

FATTY-ACID AMIDE HYDROLASE

CROSS REFERENCE TO RELATED APPLICATIONS

This application is a continuation-in-part of U.S. patent application Ser. No. 08/489,535, filed on Jun. 12, 1995, now abandoned, the disclosures of which is incorporated herein by reference.

STATEMENT OF GOVERNMENT RIGHTS

This invention was made with government support under a National Institutes of Health Shared Instrumentation grant No. 1 S10 RR07273-01. The government has certain rights in the invention.

TECHNICAL

The invention relates to an enzyme which catalyzes a hydrolytic conversion between soporific fatty acid primary amides and their corresponding fatty acids and is designated a fatty-acid amide hydrolase (FAAH), to methods for enzymatically catalyzing such conversions, and to methods for inhibiting the enzymatic catalysis of such conversions. More particularly, the invention relates to FAAH protein, in either isolated or recombinant form, and to its use and inhibition.

BACKGROUND

Sleep is a natural, periodic behavioral state during which the body rests itself and its physiological powers are restored. It is characterized by a loss of reactivity to the environment. During sleep, certain physiological processes of both the body and the brain function differently than they do during alert wakefulness. Normal sleep consists of at least two quite different behavioral states: synchronized sleep, during which the electroencephalogram consists of slow waves of high amplitude, and desynchronized sleep (DS) or activated sleep characterized by rapid eye movements (REM sleep), in which the electroencephalogram pattern is characterized by waves of high frequency and low amplitude. Synchronized sleep is further characterized by slow and regular respiration, by relatively constant heart rate and blood pressure, and by a predominance of delta waves. Synchronized sleep usually consists of four stages, followed by a period of activated sleep. Each cycle lasts between 80 and 120 minutes. In contrast, desynchronized sleep is further characterized by irregular heart rate and respiration, periods of involuntary muscular jerks and movements, and a higher threshold for arousal. Periods of desynchronized sleep last from 5–20 minutes and occur at about 90 minute intervals during a normal night's sleep.

Sleep disorders include sleep deprivation and paroxysmal sleep, i.e., narcolepsy. There has been no known pharmacological method for promoting or inhibiting the initiation of sleep or for maintaining the sleeping or waking state.

Cerebrospinal fluid (liquor cerebrosinalis) is a clear, colorless fluid that circulates within the four ventricles of the brain and the subarachnoid spaces surrounding the brain and spinal cord Cerebrospinal fluid originates as an ultrafiltrate of the blood secreted by the choroid plexus in the lateral third and fourth ventricles. Cerebrospinal fluid is also sometimes called neurolymph. After passing through the four ventricles and the subarachnoid spaces, cerebrospinal fluid is largely resorbetd into the venous system via the arachnoid villi. Cerebrospinal fluid serves as a medium for the removal of catabolites, excretions, and waste materials from the tissues bathed by it. To date, no factor derived from cerebrospinal fluid has been reported to correlate with sleep deprivation. What is needed is a method for analyzing cerebrospinal fluid for identifying a biochemical factor generated by subject that correlates with sleep deprivation.

Since the seminal discovery of prostaglandins, there has been increasing recognition of the role of fatty acids and their derivatives in important physiological processes, e.g., B. Samuelsson, *Les Prix Nobel* 1982, pp. 153–174.

Cis-9,10-Octadecenoamide has been isolated from the cerebrospinal fluid of sleep-deprived cats and has been shown to exhibit sleep-inducing properties when injected into rats. Other fatty acid primary amides in addition to cis-9,10-octadecenoamide were identified as natural constituents of the cerebrospinal fluid of cat, rat, and man, indicating that these compounds compose a distinct family of brain lipids. Together, these results teach that fatty acid primary amides represent a new class of biological signalling molecules that can be employed for inducing subjects to sleep. Preferrers fatty acid primary amides include an alkyl chain having an unsaturation and are represented by the following formula: $NH_2C(O)(CH_2)_{(6 \leq n \leq 11)}CH=CH(CH_2)_{(8 \leq n \leq 5)}CH_3$. Preferred soporific fatty acid primary amides have an unsaturation with a cis configuration within their alkyl chain. In addition to cis-9,10-octadecenoamide, other soporifically active fatty acid primary amides include cis-8,9-octadecenoamide, cis-11,12-octadecenoamide, and cis-13,14-docosenoamide.

Deutsch et al, *Biochem. Pharmacol.*, 46:791 (1993) has identified an amidase activity which catalyzes both the hydrolysis and synthesis of arachidonylethanolamide (anandamide) from the membrane subcellular fractions taken from neuroblastoma, glioma cells and crude homogenates of rat brain tissues. The study detected the uptake and enzymatic breakdown of arachidonylethanolamide (anandamide) to arachidonic acid (and vice versa) from the homogenates of tissues from brain, liver, kidney and lung but not from rat heart and skeletal muscles.

The active membrane fraction which displayed this amidase activity was prepared by either homogenizing the desired cell line and subsequently subjecting the crude homogenate to density centrifugation or by taking the crude homogenates of rat brains and directly incubating them with anandamide.

The uptake and degradation of arachidonylethanolamide (anandamide) was assayed by incubation of [$^3$H]-anandamide (NEN, NET-1073, 210 Ci/mmol) in the cell culture medium. It was found, by liquid scintillation counting of the aqueous and organic phases, that arachidonic acid and anaiidamide distributed in the organic phase. Thus, the organic extract of the cell medium was subsequently visualized using thin-layer chromatography, sprayed with a surfaces autoradiograph enhancer (EN$^3$HANCE, Dupont) and exposed to X-ray film (Kodak X-OMAT AR) at –80° C.

The serine protease inhibitor, phenylmethylsulfonyl fluoride at 1.5 mM concentration completely inhibited the amidase activity. Other inhibitors tested had little or no effect on the activity and included aprotinin, benzamidine, leupeptin, chymostatin and pepstatin.

In a second manuscript, Deusch et. al. (*J. Biol Chem.*, 1994, 269, 22937) reports the synthesis of several types of specific inhibitors of anandamide hydrolysis and their ability to inhibit anandamide breakdown in vitro. Four classes of compounds were synthesized and include fatty acyl ethanolamides, α-keto ethanolamides, α-keto ethyl esters and trifluoromethyl ketones. The most effective class of compounds were the trifluoromethyl ketones and α-keto esters. The least potent inhibitors were the α-keto amides and saturated analogs of anandamide.

As an example, when anandamide is incubated with neuroblastoma cells, it is rapidly hydrolyzed to arachidonate but in the presence of the inhibitor arachidonyl trifluoromethyl ketone, there is a 5 fold increase of anandamide levels. The study infers that polar carbonyls such as those found in trifluoromethyl ketones, may form stabilized hydrates that mimic the tetrahedral intermediates formed during the reaction between the nucleophilic residue and the carbonyl group of anandamide. Deutsch suggests that the nucleophilic residue may be the active site of a serine hydroxyl in the hydrolytic enzyme.

This enzyme is classified as an amidase (EC #3.5) where the enzyme acts on carbon nitrogen bonds other than peptide bonds. The amidase activity is inhibited by the serine protease inhibitor, PMSF and the action of trifluoromethyl ketone inhibitors (and others) directly affect the hydrolytic activity of the enzyme. Furthermore, Deutsch suggests that anandamide is cleaved by a mechanism that involves an active site serine hydroxyl group.

What is needed is an identification of enzymes within the brain tissue which catalyze the degradation of soporific compound found in the cerebrospinal, for mediating the soporific activity of these compounds. What is needed is an identification of inhibitors for inhibiting the activity of enzymes which degrade soporific compounds of the type found in cerebrospinal fluid.

BRIEF SUMMARY OF THE INVENTION

An enzyme is disclosed herein which degrades soporific fatty acid primary amides, and is designated fatty-acid amide hydrolase, or FAAH. FAAH is one of the enzymes which mediates the activity of fatty acid primary amides, including soporific fatty acid primary amides.

As disclosed herein, FAAH is characterized by an enzymic activity for catalyzing a conversion cis-9,10-octadecenoamide to oleic acid, among other substrates, as shown in Scheme 1 below, and therefor was originally identified as cis-9,10-octadecenoamidase. However, it is now shown that FAAH has activity to hydrolyse a variety of fatty acid primary amides, and therefore the amidase originally referred to as cis-9,10-octadecenoamidase is more appropriately reffered to as FAAH.

SCHEME 1

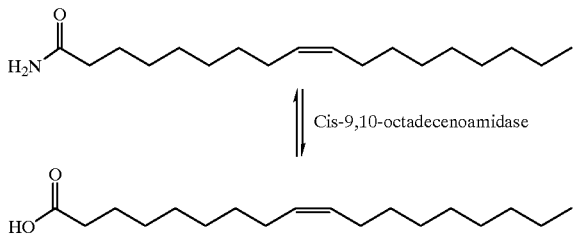

One aspect of the invention is directed to a purified form of FAAH. FAAH can be purified by a variety of methods, including a chromatographic methodology. Preferred chromatographic methodologies include affinity chromatography, electric chromatography, gel filtration chromatography, ion exchange chromatography, and partition chromatography. In affinity chromatography, a solid phase adsorbent contains groups that bind particular proteins because they resemble ligands for which the proteins have a natural affinity. In a preferred mode, the solid phase adsorbent contains one or more FAAH inhibitors which bind the enzyme. In antibody affinity chromatography, a solid phase immunoabsorbent having antibodies with a bind specificity with respect to FAAH are employed. In electric chromatography or electrophoresis, the FAAH is separated from other molecules according to its molecular weight or isoelectric point. In gel filtration, also known as gel permeation, molecular sieve, and exclusion chromatography, the solid phase creates a stationary phase of gel solvent and a mobile phase of excluded solvent. The FAAH is separated according to its molecular size as it partitions between the stationary and mobile phases. The gel particles are selected to have a exclusion size in excess of FAAH. In ion exchange chromatography, a solid phase ion exchanger is employed for separating the FAAH from other molecules according to its partitioning between ionic and nonionic forces. In partition chromatography, immiscible fluids having a stationary and mobile phases are employed for separating the FAAH according to its partitioning between the two immiscible phases. Preferred chromatographic methodologies include DEAE chromatography, affinity chromatography on a solid phase having attached Hg groups derivatized with an inhibitor of FAAH such as a trifluoroketone.

In a preferred mode, a crude source of FAAH is purified in four steps. In the first step, a crude source of FAAH is purified by exchange chromatography using a DEAE chromatography column to form a first elution product. In the second step, the elution product from the first step is further purified by partitioning by with affinity chromatography to form a second elution product. In the third step, elution product from the second step is further purified by partitioning with Heparin affinity chromatography to form a third elution product. In the fourth step, the elution product from the third step is further purified by partitioning with an stationary phase derivatized with a trifluoroketone inhibitor of FAAH. The eluant from the fourth step form the purified form of FAAH. FAAH can be isolated from any of a variety of mammalian species, including rat, mouse or human, as described herein.

Fatty-acid amid hydrolase (FAAH) is characterized by inclusion of an amino acid sequence selected from a group consisting of:

a.) GGSSGGEGALIGSGGSPLGLGTDIGGSIRFP (SEQ ID NO 5), b.) SPGGSSGGEGALIGS (SEQ ID NO 6), c.) ALIGSGGSPLGLGTD (SEQ ID NO 7),

-continued d.) GLGTDIGGSIRFPSA (SEQ ID NO 8), e.) RFPSAFCGICGLKPT (SEQ ID NO 9), f.) GLKPTGNRLSKSGLK (SEQ ID NO 10), g.) KSGLKGCVYGQTAVQ (SEQ ID NO 11), h.) QTAVQLSLGPMARDV (SEQ ID NO 12), i.) MARDVESLALCLKAL (SEQ ID NO 13), j.) CLKALLCEHLFTLDP (SEQ ID NO 14), k.) FTLDPTVPPFPFREE (SEQ ID NO 15), l.) PFREEVYRSSRPLRV (SEQ ID NO 16), m.) RPLRVGYYETDNYTM (SEQ ID NO 17), n.) DNYTMPSPAMRRALI (SEQ ID NO 18), o.) RRALIETKQRLEAAG (SEQ ID NO 19), p.) LEAAGHTLIPFLPNN (SEQ ID NO 20), q.) FLPNNIPYALEVLSA (SEQ ID NO 21), r.) EVLSAGGLFSDGGRS (SEQ ID NO 22), s.) DGGRSFLQNFKGDFV (SEQ ID NO 23), t.) KGDFVDPCLGDLILI (SEQ ID NO 24), u.) DLILILRLPSWFKRL (SEQ ID NO 25), v.) WFKRLLSLLLKPLFP (SEQ ID NO 26), w.) KPLFPRLAAFLNSMR (SEQ ID NO 27), x.) LNSMRPRSAEKLWKL (SEQ ID NO 28), y.) KLWKLQHEIEMYRQS (SEQ ID NO 29), z.) MYRQSVIAQWKAMNL (SEQ ID NO 30), aa.) KAMNLDVLLTPMLGP (SEQ ID NO 31), and ab.) PMLGPALDLNTPGR (SEQ ID NO 32).

Another aspect of the invention is directed to a method for catalyzing the hydrolysis of a fatty acid primary amide. In this hydrolysis method, the fatty acid primary amide is combined or contacted with a catalytic amount of purified form of FAAH. In a preferred mode, the fatty acid primary amide is of a type which includes an alkyl chain having an unsaturation or more particularly is represented by the following formula:

$$NH_2C(O)(CH_2)_{(6 \geq n \leq 11)}CH=CH(CH_2)_{(8 \geq n \leq 5)}CH_3,$$

More particularly, the unsaturation of the alkyl chain may have a cis configuration or may be identically cis-9,10-octadecenoamide, cis-8,9-octadecenoamide, cis-11,12-octadecenoamide, or cis-13,14-docosenoamide.

Another aspect of the invention is directed to a method for inhibiting an enzymatically catalyzed hydrolysis of fatty acid primary amides, such as cis-9,10-octadecenoamide, by FAAH. In this method, FAAH is combined or contacted with an inhibitor of FAAH. Preferred inhibitors include phenylmethylsulfonyl fluoride, $HgCl_2$, and a trifluoroketone having the following structure:

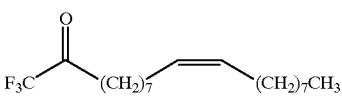

Another aspect of the invention is directed to a method for ascertaining the inhibitory activity of a candidate inhibitor of FAAH. Thus, FAAH is admixed with a candidate FAAH inhibitor to assess inhibitory capacity in a screening method.

In a preferred method for determining inhibitory activity of a candidate FAAH inhibitor, the contemplated method comprises five steps. In the first step, a mixture "A" is formed by combining FAAH and cis-9, 10-octadecenoamide substrate under reaction conditions. In the second step, a mixture "B" is formed by combining the mixture "A" with the candidate inhibitor. In the third step, the conversion of cis-9,10-octadecenoamide substrate to a hydrolysis product within mixture "A" is quantified. In the fourth step, the conversion of cis-9,10-octadecenoamide substrate to hydrolysis product within mixture "B" is quantified. In the fifth step, the inhibitory activity of the candidate inhibitor is ascertained by comparing the quantifications of steps three and four.

Another aspect of the invention is directed to a trifluoroketone inhibitor of FAAH represented by following structure:

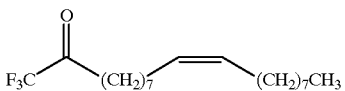

Another aspect of the invention is directed to one or more nucleotide sequences the encode part or all of FAAH. The complete nucleotide sequence that encodes human, mouse or rat FAAH are shown in SEQ ID Nos. 42, 39 or 35, respectively.

The partial nucleotide sequence of rat FAAH is represented as follows:

```
CCAGGAGGTTCCTCAGGGGGTGAGGGGCTC (SEQ ID NO 54)
TCATTGGATCTGGAGGTTCCCCTCTGGGTTT
AGGCACTGACATTGGCGGCAGCATCCGGTTC
CCTTCTGCCTTCTGCGGCATCTGTGGCCTCA
AGCCTACTGGCAACCGCCTCAGCAAGAGTGG
CCTGAAGGGCTGTGTCTATGGACAGACGGCA
GTGCAGCTTTCTCTTGGCCCCATGGCCCGGG
ATGTGGAGAGCCTGGCGCTATGCCTGAAAGC
TCTACTGTGTGAGCACTTGTTCACCTTGGAC
CCTACCGTGCCTCCCTTTCCCTTCAGAGAGG
AGGTCTATAGAAGTTCTAGACCCCTGCGTGT
GGGGTACTATGAGACTGACAACTATACCATG
CCCAGCCCAGCTATGAGGAGGGCTCTGATAG
AGACCAAGCAGAGACTTGAGGCTGCTGGCCA
CACGCTGATTCCCTTCTTACCCAACAACATA
CCCTACGCCCTGGAGGTCCTGTCTGCGGGCG
GCCTGTTCAGTGACGGTGGCCGCAGTTTTCT
CCAAAACTTCAAAGGTGACTTTGTGGATCCC
TGCTTGGGAGACCTGATCTTAATTCTGAGGC
TGCCCAGCTGGTTTAAAAGACTGCTGAGCCT
CCTGCTGAAGCCTCTGTTTCCTCGGCTGGCA
GCCTTTCTCAACAGTATGCGTCCTCGGTCAG
CTGAAAAGCTGTGGAAACTGCAGCATGAGAT
TGAGATGTATCGCCAGTCTGTGATTGCCCAG
TGGAAAGCGATGAACTTGGATGTGCTGCTGA
CCCCNATGYTNGGNCCNGCNYTNGAYYTNAA
YACNCCNGGNMGN
```

BRIEF DESCRIPTION OF THE DRAWINGS

FIG. 2 illustrates the determined partial amino acid sequence of the rat FAAH as described in Section B.4.

FIG. 3 illustrates a partial purification strategy involving isolation of a plasma membrane protein fraction from rat liver using 1) a sucrose gradient of the liver membrane followed by 2) a 100 mM sodium carbonate wash and 3) solubilization in trion-based buffer. The isolated liver plasma membrane is then purified by four consecutive chromatographic steps: 1) Ion exchane DEAE column, 2) Mercury inhibition column, 3) detergent exchange Heparin column followed by 4) an affinity column with a trifluoroketone inhibitor. The purified protein was determined to have a 20–30 fold enrichment of amidase activity from crude membrane protein fraction by visual comparison of the purified protein band intensity with the crude protein fraction. Estimated purified yield is 10–15% from crude liver plasma membrane protein.

FIG. 4 illustrates the affinity column purification strategy (step 4, FIG. 3) using a trifluoroketone inhibitor which is linked to a disulfide-derivatized solid support (pyridyl disulfide beads).

FIG. 9 illustrates the deduced encoded amino acid residue sequence of rat oleamide hydrolase also referred to as a fatty acid amide hydrolase or FAAH (SEQ ID NO: 36). The encoded rat FAAH is appropriately abbreviated rFAAH. Bold type indicates the putative transmembrane spanning domain as predicted by PSORT. The seven discontinuous underlined regions indicate the seven separate peptides, the designation of which is consecutive, obtained by HPLC purification of a trypsin digest of the enzyme. The double-underlined segment is the putative SH3-domain-binding sequence.

FIGS. 10-1 through 10-5 show the continuous double-stranded cDNA sequence for rat FAAH as described in Section D. The encoded amino acid sequence is also indicated beginning with the ATG start site encoding methionine (M). The stop codon is also shown as boxed. The top and bottom strands of the cDNA sequence are respectively listed in SEQ ID NOs 35 and 37 with the amino acid sequence listed with the nucleotide sequence in SEQ ID NO 35 and by itself in SEQ ID NO 36.

FIG. 11 illustrates the alignment of the amidase signature sequence region of the rat FAAH (SEQ ID NO 36 from amino acid residue 215 to and including 246) with several other representative amidases as further described in Section D1. Residues of the signature sequence that are completely conserved among the family members are shown in bold type and the relative amino acid position of the signature sequence of each member is given by the numbers just preceding and following the sequence information. From top to bottom, the sequences have the following respective SEQ ID NOs: 36 (from residue 215 to 246) ; 47, 48, 49, 50, 51, 52 and 53.

FIG. 12A and 12B show the respective results of Southern and Northern blots as probed with an internal 800 bp fragment of rat FAAH cDNA as further described in Section D.

FIGS. 13-1 through 13-4 show the continuous double-stranded cDNA sequence for mouse FAAH as described in Section D2. The encoded amino acid sequence is also indicated beginning with the ATG start site encoding methionine (M). The stop codon is also shown as boxed. The top and bottom strands of the cDNA sequence are respectively listed in SEQ ID NOs 39 and 41 with the amino acid sequence listed with the nucleotide sequence in SEQ ID NO 39 and by itself in SEQ ID NO 40.

FIGS. 14-1 through 14-5 show the continuous double-stranded cDNA sequence for human FAAH as described in Section D3. The encoded amino acid sequence is also indicated beginning with the ATG start site encoding methionine (M). The stop codon is also shown as boxed. The top and bottom strands of the cDNA sequence are respectively listed in SEQ ID NOs 42 and 44 with the amino acid sequence listed with the nucleotide sequence in SEQ ID NO 42 and by itself in SEQ ID NO 43.

FIG. 15A shows the expression of recombinant rat FAAH in COS-7 cells produced as described in Section E as performed by thin layer chromatography demonstrating the conversion of labeled oleamide to oleic acid as further described in Section F.

FIG. 15B shows the inhibition of recombinant rat FAAH by trifluoromethyl ketone also performed as described in FIG. 15A as further described in Section F.

FIG. 15C shows the results of Western blotting of recombinant rat FAAH with antibodies generated against peptide 2 as shown in FIG. 9 as shown in the four left lanes (1–4) and as competed with peptide 2 as shown in the four right lanes (5–8). Samples of untransfected COS-7 cell extract are shown in lanes 4 and 8, FAAH-transfected COS-7 cell extracts are shown in lanes 3 and 7, affinity-purified rat FAAH is shown in lanes 2 and 6 and a mixture of FAAH-transfected COS-7 cell extracts and affinity-purified FAAH is run in lanes 1 and 5. The proteins were probed with antibodies in the absence (lanes 1–4) or presence (lanes 5–8) of competing peptide antigen. The FAAH-transfected COS-7 cell extract but not the control contained an immunoreactive 60K–65K protein that was effectively competed away by preincubation of the antibodies with excess peptide antigen while the trace quantities of cross reactive protein observed in both transfected and untransfected COS-7 cell extracts were not competed by the peptide.

DETAILED DESCRIPTION OF THE INVENTION

Figure 1:
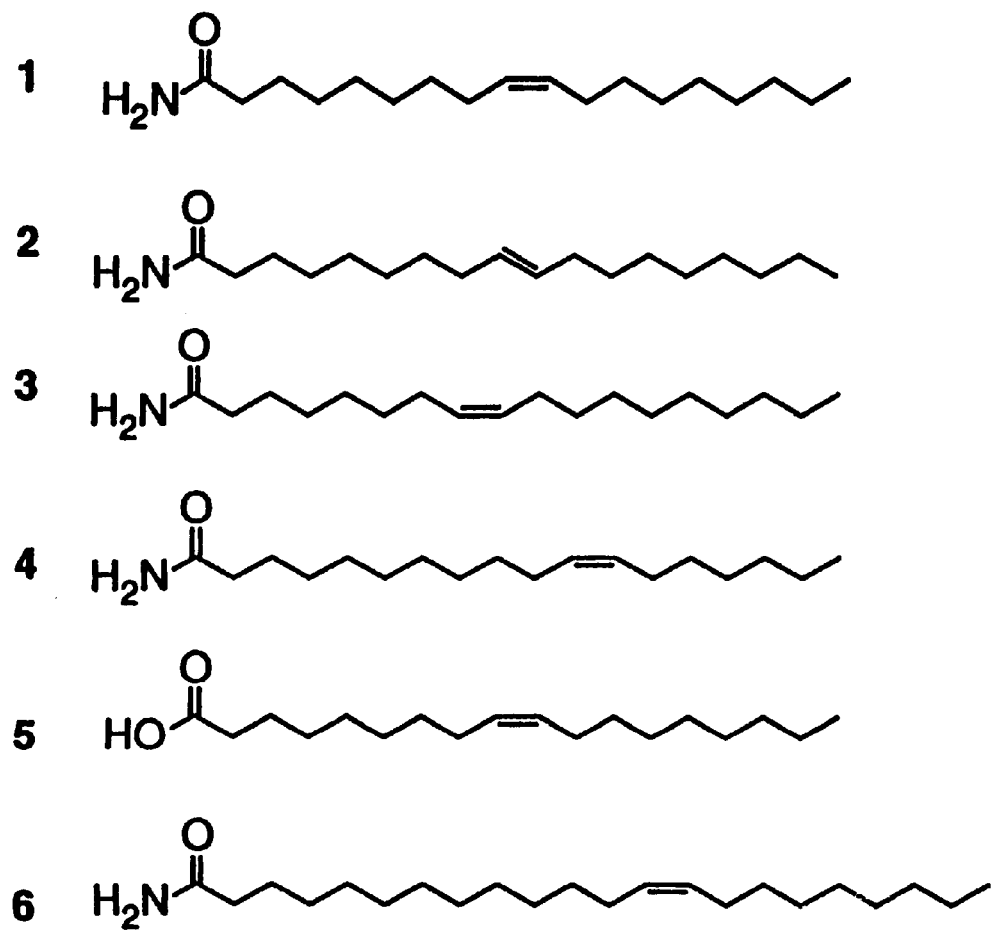
FIG. 1 illustrates the structures of natural agent, cis-9,10-octadecenoamide (1), related analogs (2-6). Compound 6 is the preferred structure for naturally occurring $C_{22}$ fatty acid amide.

A. Protocols for the Induction of Sleep

Synthetic cis-9,10-octadecenoamide was injected (ip) into rats in order to test its effect on spontaneous behavior at different doses: 1 (n=2), 2 (n=2), 5 (n=7), 10 (n=10), 20 (n=2), and 50 (n=2) mg, where n =number of rats tested. Rats were injected during a reversed dark period (12:12) two hours after the lights cycled off and were observed in their home cages. With the lower doses (1 and 2 mg), no overt effect on spontaneous behavior was witnessed. However, at a threshold of 5 mg and above there was a marked effect consisting of an induction of long-lasting motor quiescence associated with eyes closed, sedated behavior characteristic of normal sleep. Also as with normal sleep, the rats still responded to auditory stimuli with orienting reflex and sustained attention toward the source of stimulation. In addition, motor behavior was impaired. The latency to behavioral sedation following administration was about 4 minutes and subjects were normally active again after 1 hour (5 mg), 2 hour (10 mg), or 2.5 hour (20 mg and 50 mg).

We have compared cis-9,10-octadecenoamide to vehicle and the synthetic analogs listed in FIG. 1 to estimate the structural specificity of its sleep-inducing potential. Neither vehicle (5% ethanol in saline solution) nor oleic acid (5) showed any overt behavioral effect. Trans-9,10-octadecenoamide demonstrated similar pharmacological effects to its cis counterpart, but was much less potent as measured by the comparatively shorter duration time for its sleep-inducing properties (at 10 mg per rat, the biological effect lasted one hour for the trans isomer and two hours for the cis isomer). When the olefin was moved either direction along the alkyl chain (to the 8,9 (3) or 11,12 (4) positions) or the alkyl chain length was extended to 22 carbons (6), a substantial reduction in both the degree and duration of the pharmacological effects was observed, and while the mobility of the rats still decreased, their eyes remained open and their alertness appeared only slightly affected. Finally, polysomnographic studies on rats injected with cis-9,10-octadecenoamide show an increase in the total time of slow wave sleep (SWS) as well as in the mean duration of the SWS individual periods when compared to vehicle controls. More particularly, male Sprague-Dawley rats (300 g at the time of surgery) were implanted under halothane anesthesia (2–3%) with a standard set of electrodes for sleep recordings. This included two screw electrodes placed in the parietal bone over the hippocampus to record the subjects electroencephalogram (EEG) and two wire electrodes inserted in the neck musculature to record postural tone through electromyographic activity (EMG). Rats were housed individually with at libitum access to food and water. The dark-light cycle was controlled (12:12, lights on a 10:00 p.m.). One week after the surgery, rats were habituated to the recording conditions for at least three days. Upon the completion of the habituation period, rats received 2 milliliter (ip) of either: vehicle (5% ethanol/saline solution), cis-9,10-octadecenoamide (10 mg), or oleic acid (10 mg). Rats were continuously recorded for four hours after the ip injection (12:00 p.m.–4:00 p.m.) Rats were observed for spontaneous changes in behavior through a one-way window. Sleep recordings were visually scored and four stages were determined: wakefulness, slow-wave-sleep 1 (SWS1), slow-wave-sleep 2 (SWS2), and rapid eye movement (REM) sleep.

These increases with respect to slow wave sleep (SWS) were at the expense of waking. Distribution of REM sleep does not seem to be altered. Together, these data suggest that cis-9,10-octadecenoamide could play an important role in slow-wave sleep modulation.

The traditional view of lipid molecules as passive structural elements of cellular architecture is rapidly giving way to an ever increasing awareness of the active roles these agents play in transducing cell signals and modifying cell behavior, e.g., Liscovitch et al, *Cell,* 77:329 (1994). An intriguing feature of the fatty acid amides studied here is that they belong to a family of simple molecules in which a great deal of diversity may be generated by simply varying the length of the alkane chain and the position, stereochemistry, and number of its olefin(s). Interestingly, other neuroactive signalling molecules with amide modifications at their carboxy termini have been reported, from carboxamide terminal peptides to arachidonylethanolamide. Neuroactive signalling molecules employing carboxamide terminal peptides are disclosed by Eipper et al, *Annu. Rev. Neurosci.,* 15:57 (1992). Neuroactive signalling molecules employing arachidonylethanolamide is disclosed by Devane et al, *Science,* 258:1946 (1992). It is disclosed herein that cis-9,10-octadecenoamide is a member of a new class of biological effectors in which simple variations of a core chemical structure have unique physiological consequences.

B. Isolation and Assay of Integral Membrane Protein Fraction with FAAH Activity

1. Observations on Lipid Amidase Activity

Lipid amidase activity has been observed in brain, liver, lung, kidney and spleen tissues, but not in heart tissue. The activity is inhibited by 1 mM PMSF (phenylmethylsulfonyl fluoride) and 50 mM HgCl, which is a test for sulfhydryl group dependency of the reaction. Since the fractions are not solubilized by 100 mM sodium carbonate (pH 11.5), the sample is apparently a membrane protein, which has been identified in nuclear, microsomal, and plasma membrane subcellular fractions, but not in the cytosol.

Figure 6:
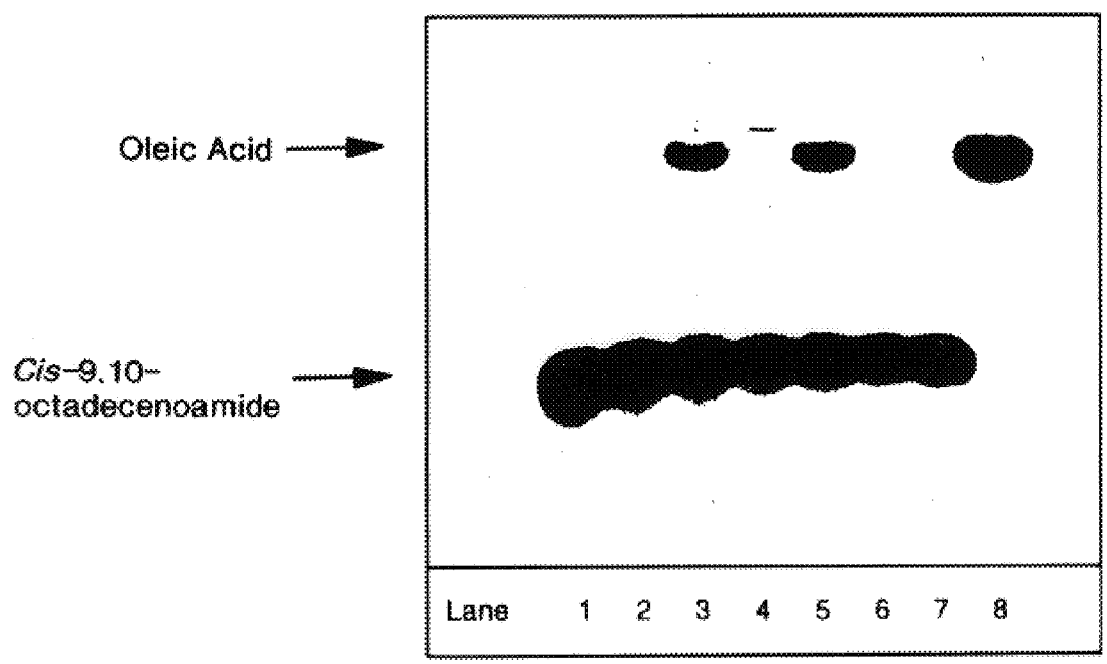
FIG. 6 represents an autoradiogram of a thin layer chromatography plate ($SiO_2$, 55% ethyl acetate/hexanes) illustrating the FAAH activity of a rat brain membrane fraction with respect to the hydrolysis of radio-labelled cis-9,10-octadecenoamide to oleic acid and its inhibition by phenylmethyl sulfonyl fluoride (PMSF). Lane number, content: lane 1, Cis- 9,10-octadecenoamide standard; lane 2, Cis-9,10-octadecenoamide with rat brain soluble fraction; lane 3, Cis-9,10-octadecenoamide with rat brain membrane fraction; lane 4, Cis-9,10-octadecenoamide with rat brain membrane fraction +1 mM phenylmethylsulfonyl fluoride (PMSF); lane 5, Cis-9,10-octadecenoamide with rat brain membrane fraction +5 mM EDTA; lane 6, Cis-9,10-octadecenoamide with rat pancreatic microsomes; lane 7, Cis-9,10-octadecenoamide with proteinase K (200 mg); lane 8, oleic acid standard.

The enzyme catalyzed hydrolysis of cis-9,10-octadecenoamide to oleic acid by purified cis-9,10-octadecenoamide and inhibition of this enzyme by PMSF is disclosed on an autoradiogram of a thin layer chromatographic plate (SiO2, 55% ethyl acetate/hexanes), illustrated in FIG. 6. In each case the enzymic reaction is performed is a separate reaction vessel and the product is spotted onto a TLC plate. The various reaction conditions for the reaction vessel corresponding to each lane are identified as follows:

lane 1: Cis-9,10-octadecenoamide standard;

lane 2: Cis-9,10-octadecenoamide with rat brain soluble fraction;

lane 3: Cis-9,10-octadecenoamide with rat brain membrane fraction;

lane 4: Cis-9,10-octadecenoamide with rat brain membrane fraction +1 mM PMSF;

lane 5: Cis-9,10-octadecenoamide with rat brain membrane fraction +5 mM EDTA;

lane 6: Cis-9,10-octadecenoamide with rat pancreatic microsomes;

lane 7: Cis-9,10-octadecenoamide with proteinase K (200 mg); and lane 8: oleic acid standard.

Figure 7:
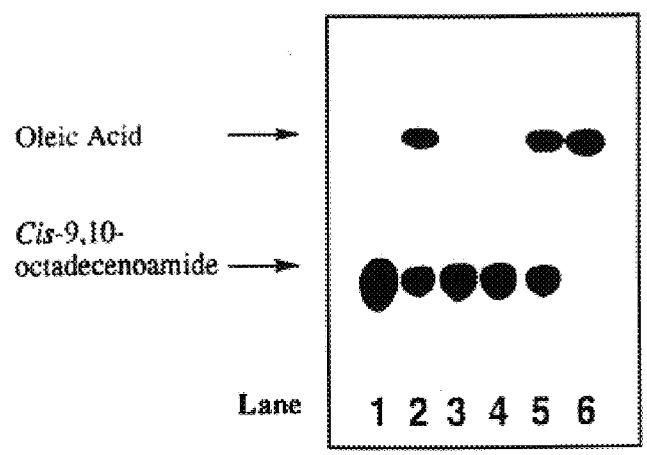
FIG. 7 represents an autoradiogram of a thin layer chromatography plate ($SiO_2$, 55% ethyl acetate/hexanes) illustrating the FAAH activity of a rat brain membrane fraction with respect to the hydrolysis of radio-labelled cis-9,10-octadecenoamide to oleic acid and its inhibition by mercuric chloride ($HgCl_2$). The optimal concentrations required for inhibition of amide hydrolysis activity lies between 50 mM and 5 mM $HgCl_2$. The various lanes of the TLC plate are identified as follows: lane 1, Cis-9,10-octadecenoamide standard; lane 2, Cis-9,10-octadecenoamide with rat brain soluble fraction; lane 3, Cis-9,10-octadecenoamide with rat brain membrane fraction and 500 mM $HgCl_2$; lane 4, Cis-9,10-octadecenoamide with rat brain membrane fraction and 50 mM $HgCl_2$; lane 5, Cis-9,10-octadecenoamide with rat brain membrane fraction and 5 mM $HgCl_2$; lane 6, oleic acid standard. A typical $HgCl_2$ inhibition study uses a 100 mM $HgCl_2$ stock (27 mg in 1mL Tris buffer (50 mM), pH 7.5) of $HgCl_2$.
Figure 8:
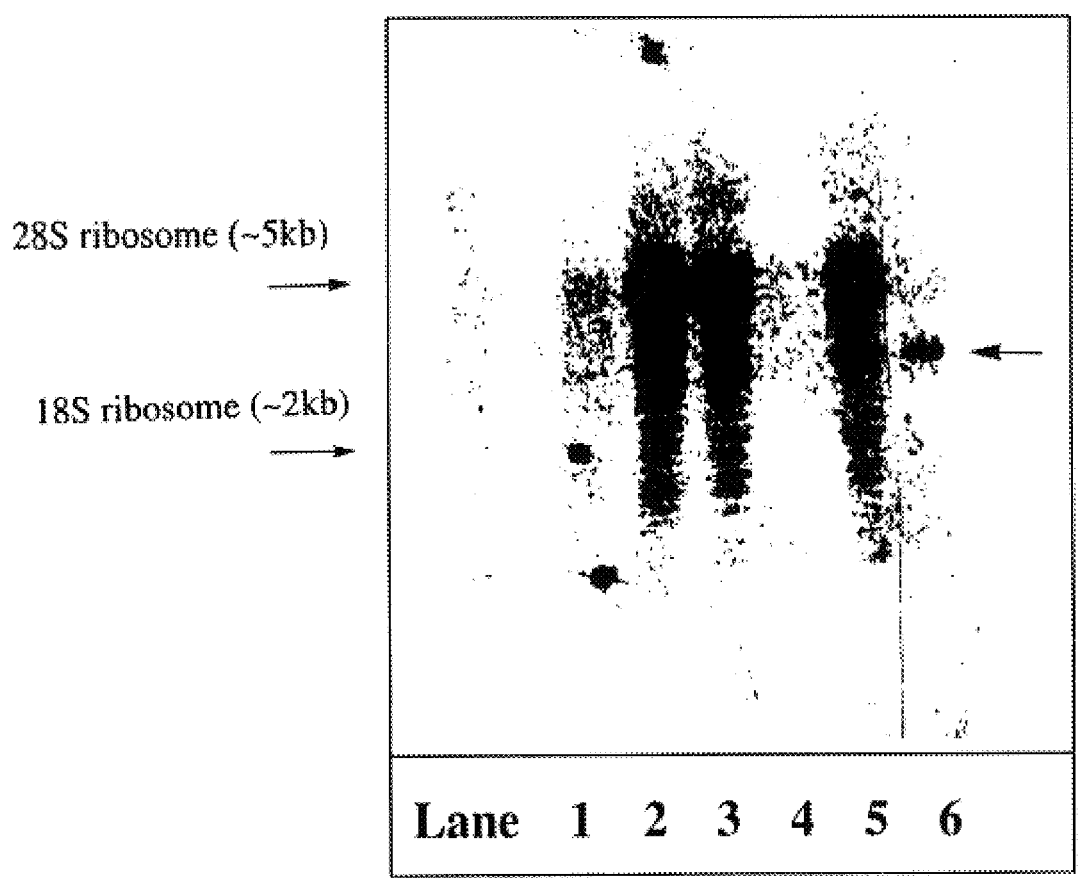
FIG. 8 represents a northern blot of mRNA obtained from cloning procedures. Ribosomal markers are shown by the arrows, next to lane 1, and indicate 5 kb and 2 kb bands. The arrow next to lane 6 points to a 3 kb band which is representative of the oleic amidase enzyme. Lane 1 is total RNA from rat brain; lane 2 is total RNA from rat lung; lane 3 is total RNA from rat kidney; lane 4 is total RNA from rat heart; lane 5 is total RNA from rat liver; lane 6 is mRNA from rat liver (mRNA loaded in lane 6 is approximately 500 ng); total respective RNA loaded in lanes 1–5 was approximately 15 μg.

Inhibition studies of Cis-9,10-octadecenoamide hydrolysis to oleic acid with $HgCl_2$ are illustrated in FIG. 7. Between 50 mM and 5 mM $HgCl_2$ lies the optimal concentrations required for inhibition of amide hydrolysis activity. The enzyme catalyzed hydrolysis of cis-9,10-octadecenoamide to oleic acid by purified cis-9,10-octadecenoamide and inhibition of this enzyme by $HgCl_2$ is performed in a series of reaction vessels and spotted onto a thin layer chromatographic plate (SiO2, 55% ethyl acetate/hexanes). A typical $HgCl_2$ inhibition study uses a 100 mM $HgCl_2$ stock (27 mg in lmL Tris buffer (50 mM), pH 7.5) of $HgCl_2$. The various reaction conditions for the reaction vessels corresponding to each lane are identified as follows:

lane 1: Cis-9,10-octadecenoamide standard;

lane 2: Cis-9,10-octadecenoamide with rat brain soluble fraction;

lane 3: Cis-9,10-octadecenoamide with rat brain membrane fraction and 500 mM $HgCl_2$;

lane 4: Cis-9,10-octadecenoamide with rat brain membrane fraction and 50 mM $HgCl_2$;

lane 5: Cis-9,10-octadecenoamide with rat brain membrane fraction and 5 mM $HgCl_2$;

SCHEME 2

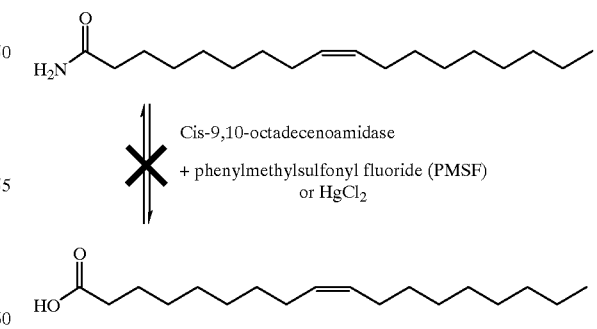

A unique enzymatic activity capable of degrading the putative effector molecule, cis-9,10-octadecenoamide has been identified and is disclosed herein. Rapid conversion of $^{14}C$-cis-9,10-octadecenoamide to oleic acid by rat brain membrane fractions was observed by TLC. The enzymatic activity was unaffected by 5 mM EDTA, but was completely inhibited by 1 mM phenylmethylsulfonyl fluoride (PMSF). Only trace amide hydrolysis activity was observed with rat brain soluble fractions, while rat pancreatic microsomes and proteinase K showed no significant capacity to hydrolyze cis-9,10-octadecenoamide to oleic acid.

2. Synthesis of Fatty Acid Primary Amides

Preferred protocols for synthesizing exemplary fatty acid primary amides are provided. The synthetic protocols differ only with respect to the chain length of the starting materials, the product yields, and the separation of the various cis and trans products. Accordingly, exemplary descriptions of synthetic protocols for the synthesis of cis-9,10-octadecenoamide and several other fatty acid primary amides are provided and serve to illustrate the synthetic protocol for the entire class of fatty acid primary amides.

3. Isolation of Rat Integral Membrane Protein Fraction with FAAH Activity

The protocol described herein is for about 5–10 g of tissue. The rat liver(s) are collected, weighed and then placed in 1 mM $NaHCO_3$ on ice. Next, the liver is cut up, rinsed (2×) with 1 mM $NaHCO_3$ and minced with a razor blade on a sheet of wax. It is then placed into 25 ml of 1 mM sodium bicarbonate and homogenized in a tissuemizer for 2 minutes at setting 6. A dilution to 100 ml with 1 mM sodium bicarbonate is subsequently performed, which is followed by a filtration through 4 layers of cheesecloth and then through 8 layers. The filtrate is then brought up to 100 ml and split into four JA-20 tubes and topped off with 1 mM sodium bicarbonate. The tubes are spun at 6,000 rpm (4500× g) for 12 minutes at 4° C. in the JA-20 rotor. Using a Pasteur pipette, the fat layer is sucked off and the supernatant layer is decanted and saved.

Next, the pellet is resuspended in the remaining supernatant layer with a syringe and needle. 20 mL fractions of the resuspension are then dounced 16 times with a 15 ml dounce homogenizer. The fractions are then combined into a single JA-20 tube and brought up to volume with 1 mM $NaHCO_3$. The tubes are next spun again at 6,000 rpm (4500×g) for 15 minutes at 4° C. in a JA-20 rotor and the supernatant is subsequently poured off and saved. The pellet is resuspended and dounced as before and then brought up to 10 ml volume with lmM sodium bicarbonate. Next, 20 mL of 67% sucrose solution is added to a final volume of 30 ml and the mixture is split into 2 tubes. An additional 25 mL of 30% sucrose is added to the top of each tube and spun at 27 K rpm for 1 hour 45 minutes at 4° C. in an ultracentrifuge. The fractions are collected from the sucrose gradient and the middle band from the sucrose gradient (plasma membrane band) is placed in a capped plastic tube and filled with 1 mM sodium bicarbonate. The tube is subsequently spun at 17,000 rpm for 35 minutes at 4° C.

The supernatant is discarded and the pellets are resuspended (with Douncing) in 100 mM of sodium carbonate. This solution is subsequently kept on ice for 1 hour and then spun at 100,000 g for 1 hour. The supernatant (solubilized peripheral membrane proteins) is discarded since no lipid amidase activity is present in this fraction and the pellet is resuspended (with Douncing) in 10% glycerol, 1% Triton, 0.1% phosphatidyl choline, 20 mM Hepes buffer and then stirred for two hours at 4° C. Finally the solution is spun at 100,000 g for 1 hour and the supernatant thus obtained is further purified as follows.

4. Purification Via 4 Step Column Chromatography Process

Step 1 DEAE column/ ion exchange (FIG. 3). The above solubilized supernatant batch is further purified. The supernatant batch is mixed with DEAE-Sephadex (Diethylaminoethyl-Sephadex, commercially available from Sigma chemical company) ion exchange resin for 1 hour at 40° C. The fraction which is bound to the DEAE resin, displays the lipid amidase activity (none in flow through). Solubilized rat liver plasma membrane (in BI: 10% glycerol, 1% Triton X-100, 1 mM EDTA, 20 mM Hepes, pH 7.2) is passed over DEAE Fast Flow column (Pharmacia) and washed with 5 column volumes of BI, 0.2% Triton. Then the amidase activity is eluted with 1 column volume each of 50 mM, 100 mM, and 200 mM NaCl in BI with 0.2% Triton.

Step 2 Hg Column (FIG. 3). The above eluent from the DEAE exchange, is mixed with p-chloromercuric benzoic acid resin (Commercially available from BioRad chemical company) for 1 hour at 4° C. The fraction which is bound to the above mercury resin, displays the lipid amidase activity (none in flow through), is washed with 5 column volumes of BI with 0.2% Triton, 5 column volumes of BI with 0.2% Triton and 150 mM NaCl, and eluted with 1.5 column volumes BI with 0.2% Triton, 150 mM NaCl, and 25 mM b-mercaptoethanol.

Step 3 Heparin column (FIG. 3). Hg-eluted amidase activity was passed over Heparin column (BioRad) and washed with 10 column volumes of BI with 0.7% CHAPS and 150 mM NaCl (detergent exchange). Elution was conducted with 1 column volume each of BI with 0.7% CHAPS and 300 mM, 400 mM, 500 mM, 650 mM, and 750 mM NaCl,respectively, with amidase activity eluting in the final two fractions.

Step 4 Affinity column (FIGS. 3 and 4). Heparin-eluted amidase activity was mixed with Triton X-100 for a final concentration of 0.2%, and then passed over $CF_3$-inhibitor linked to activated pyridyl disulphide beads (103: attachment of inhibitor to beads is described infra) and washed with 20 column volumes of BI with 0.2% Triton X-100. Elution was conducted by passing 3 column volumes of BI with 0.2% Triton and 20 mM DTT, and letting column stand at 4o C for 30 h. Then, washing column with 1.5 column volumes of BI with 0.2% Triton and 20 mM DTT eluted single protein of 60 kD in size.

Eluted 60 kd protein was digested with trypsin and peptides were sequenced as described infra.

The purity of the activity is then assessed after this procedure according to an assay protocol.

5. Assay for Fatty-Acid Amide Hydrolase Activity:

The following thin layer chromatography (TLC) protocol is used for assaying cis-9,10 octadecenoamide hydrolysis activity, also referred to as fatty-acid amide hydrolase activity. Oleamide is first labeled with $^{14}C$. To accomplish this, $^{14}C$-Oleic acid (1–10 $\mu M$, Moravek Biochemicals, 5–50 $\mu Ci/\mu M$) in $CH_2CL_2$ (200 $\mu L$, 0.005–0.05 M) at 0° C. was treated with excess oxalyl chloride and the reaction mixture was warmed to 25° C. for 6 hours. The reaction mixture was then concentrated under a constant stream of gaseous nitrogen and the remaining residue was cooled to 0° C. and treated with excess saturated aqueous ammonium hydroxide. After 5 minutes, the reaction mixture was partitioned between Et)Ac (1.5 mL) and 10% HCl (1.0 mL). The organic layer was then washed with water (1.0 mL) and concentrated under a constant stream of gaseous nitrogen to provide $^{14}C$-oleamide in quantitative yield as judged by TLC (60% EtOAc in hexanes; oleamide $R_f$-0.2; oleic acid $R_f$-0.8).

Approximately 1 $\mu Ci$ of $^{14}C$-oleamide (specific activity 5–50 $\mu Ci/M$) in ethanol was incubated at 37° C. for 1–2 hours with 70 $\mu L$ of 126 mM Tris-HCl, pH 9.0 (final concentration of ethanol was 2.0%). The reaction mixture was then partitioned between ethyl acetate (1.0 mL) and 0.07 M Hcl (0.6 mL). The ethyl acetate layer was concentrated under a constant stream of gaseous nitrogen and the remaining residue was resuspended in 15 μL of ethanol. Approximately 3 ML of this ethanol stock was then used for TLC analysis (60% EtOAc in hexanes: oleamide $R_f$-0.2; oleic acid $R_f$-0.8). Following exposure to solvent, TLC plates were air-dired, treated with EN³HANCE spray (Dupont NEN) according to manufacturer's guidelines and exposed to film at −78° C. for 1–2 hours.

The purified protein was determined to have a 20–30 fold enrichment of amidase activity from crude membrane protein fraction by visual comparison of the purified protein band intensity with the crude protein fraction. Estimated purified yield is 10–15% (FIG. 3)

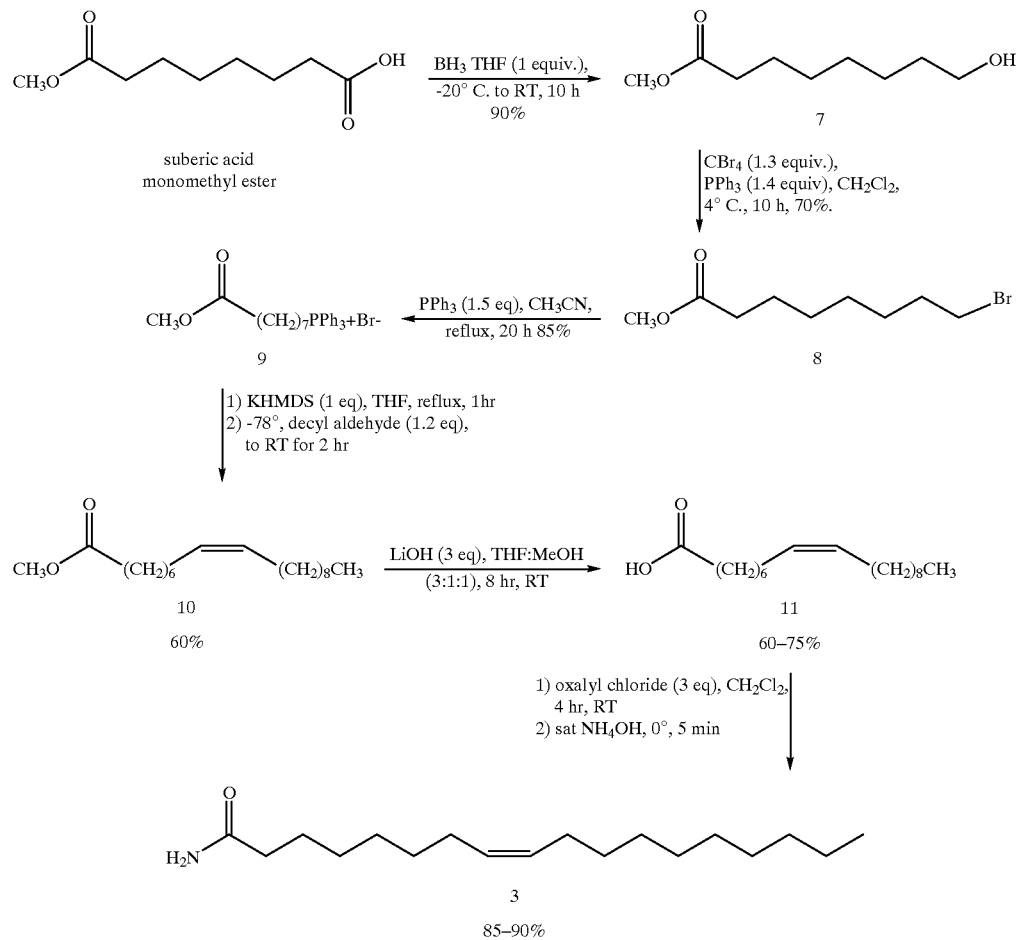

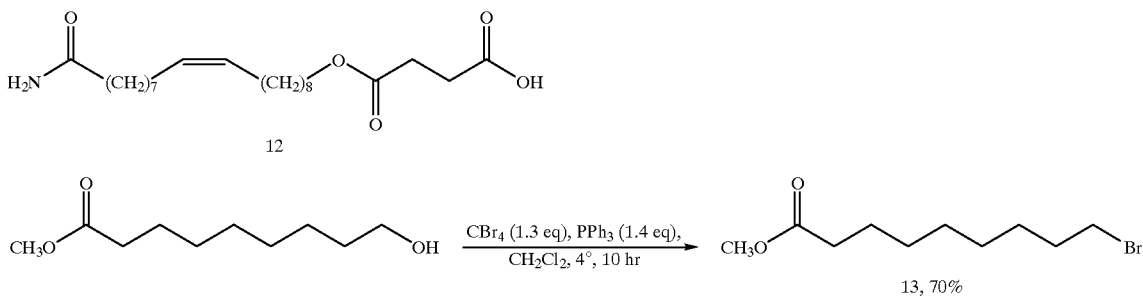

-continued

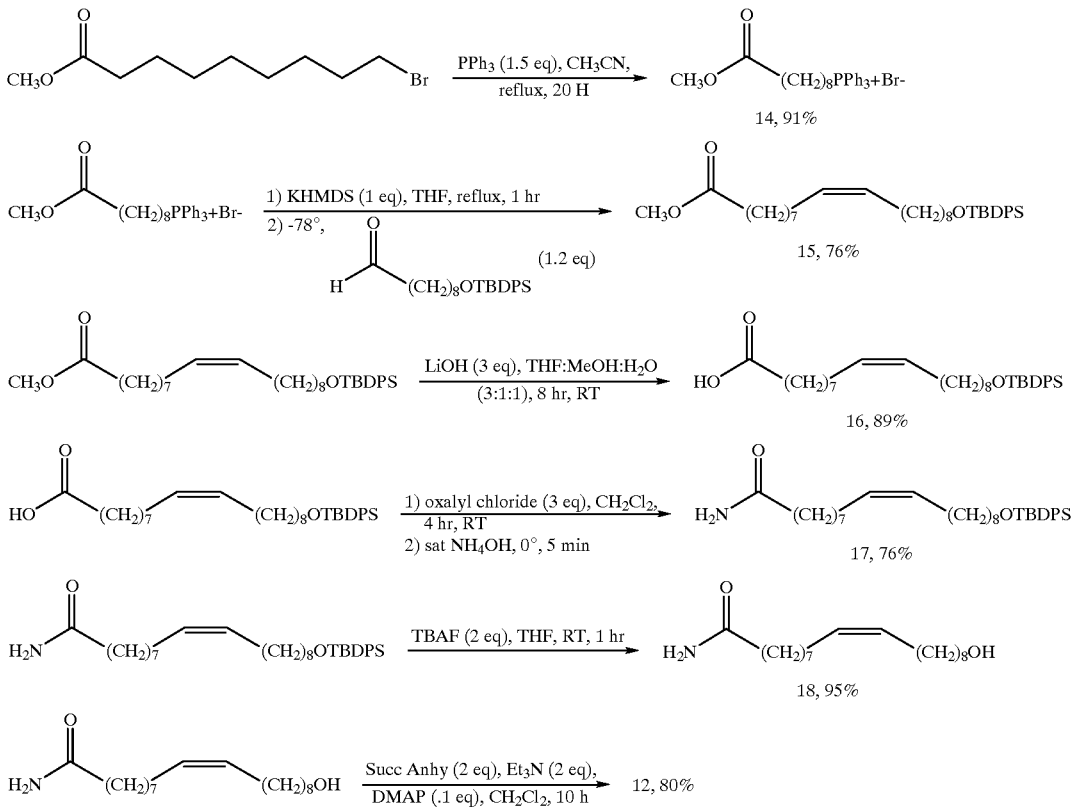

C. Synthetic Protocols

1. Cis-9,10-octadecenoamide (1: FIG. 1):

A solution of oleic acid (1.0 g, 3.55 mmol, 1.0 equiv.) in $CH_2Cl_2$ (8.9 mL, 0.4 M) at 0° C. was treated dropwise with oxalyl chloride (5.32 mL, 2.0 M solution in $CH_2Cl_2$, 10.64 mmol, 3.0 equiv.). The reaction mixture was stirred at 25° C. for 4 h, concentrated under reduced pressure, cooled to 0° C., and treated with saturated aqueous $NH_4OH$ (2.0 mL). The reaction mixture was then partitioned between ethyl acetate (EtOAc) (100 mL) and $H_2O$ (100 mL), and the organic layer was dried ($Na_2SO_4$) and concentrated under reduced pressure. Chromatography ($SiO_2$, 5 cm×15 cm, 40–100% EtOAc-hexanes gradient elution) afforded 1 as a white solid (0.810 g, 0.996 g theoretical, 81.3%): $^1$H NMR ($CDCl_3$, 250 MHz) δ 6.06 (bs, 1H, $NH_2C(O)$), 5.58 (bs, 1H, $NH_2C(O)$), 5.32 (m, 2H, CH=CH), 2.16 (t, 2H, J=7.5 Hz, $CH_2C(O)NH_2$), 2.02 (m, 4H, $CH_2CH=CHCH_2$), 1.61 (m, 2H, $CH_2CH_2C(O)NH_2$), 1.29 (b s, 14H, alkyl protons), 0.87 (t, 3H, $CH_3$); FABHRMS (NBA/NaI m/e 282.2804 ($C_{18}H_{35}NO+H^+$ requires 282.2797). The regions of the spectra that distinguish between the cis and trans isomers are the olefinic protons from δ 5.3 to 5.2 and allylic protons from δ 2.0 to 1.8. These regions identify the natural compound as cis-9,10-octadecenoamide.

2. Trans-9,10-octadecenlamide (2: FIG. 1)

A solution of elaidic acid (1.0 g, 3.55 mmol, 1.0 equiv.) in $CH_2Cl_2$ (8.9 mL, 0.4 M) at 0° C. was treated dropwise with oxalyl chloride (5.32 mL, 2.0 M solution in $CH_2Cl_2$, 10.64 mmol, 3.0 equiv.). The reaction mixture was stirred at 25° C. for 4 h, concentrated under reduced pressure, cooled to 0° C., and treated with saturated aqueous $NH_4OH$ (2.0 mL). The reaction mixture was then partitioned between ethyl acetate (EtOAc) (100 mL) and $H_2O$ (100 mL), and the organic layer was dried ($Na_2SO_4$) and concentrated under reduced pressure. Chromatography ($SiO_2$,5 cm×15 cm, 40–100% EtOAc-hexanes gradient elution) afforded 2 as a white solid. The regions of the spectra that distinguish between the cis and trans isomers are the olefinic protons from δ 5.3 to 5.2 and allylic protons from δ 2.0 to 1.8. These regions identify the compound as trans-9,10-octadecenoamide.

3. Cis-8,9-octadecenoamide (3: FIG. 1):

A solution of 11, synthesized infra, (0.130 g, 0.461 mmol, 1.0 equiv.) in $CH_2Cl_2$ (1.5 mL, 0.31 M) at 0° C. was treated dropwise with oxalyl chloride (0.69 mL, 2.0 M solution in $CH_2Cl_2$,1.38 mmol, 3.0 equiv.). The reaction mixture was stirred at 25° C. for 4 h, concentrated under reduced pressure, cooled to 0° C., and treated with saturated aqueous $NH_4OH$ (2.0 mL). The reaction mixture was then partitioned between ethyl acetate (EtOAc) (100 mL) and $H_2O$ (100 mL), and the organic layer was dried ($Na_2SO_4$) and concentrated under reduced pressure. Chromatography ($SiO_2$,5 cm×15 cm, 40–100% EtOAc-hexanes gradient elution) afforded 3 as a white solid. (0.105 g, 0.130 theoretical, 80.8%): $^1$H NMR ($CDCl_3$,250 MHz) δ 5.70–5.34 (m, 4H, $H_2NC(O)$ and CH=CH), 2.21 (t, 2H, J=7.5 Hz, $CH_2C(O)NH_2$), 2.00 (m, 4H, $CH_2CH=CHCH_2$), 1.63 (m, 2H, $CH_2CH_2C(O)NH_2$), 1.47–1.23 (m, 20H, alkyl protons), 0.87 (t, 3H, $RCH_3$); FABHRMS (NBA/CSI m/e 414.1762 ($C_{18}H_{35}NO+Cs^+$ requires 414.1773).

4. Cis-11,12-octadecenoamide (4: FIG. 1):

A solution of &11,12 octadecenoic acid (1.0 g, 3.55 mmol, 1.0 equiv.) in $CH_2Cl_2$ (8.9 mL, 0.4 M) at 0° C. was treated dropwise with oxalyl chloride (5.32 mL, 2.0 M solution in $CH_2Cl_2$,10.64 mmol, 3.0 equiv.). The reaction mixture was stirred at 25° C. for 4 h, concentrated under reduced pressure, cooled to 0° C., and treated with saturated aqueous NH₄OH (2.0 mL). The reaction mixture was then partitioned between ethyl acetate (EtOAc) (100 mL) and H₂O (100 mL), and the organic layer was dried (Na₂SO₄) and concentrated under reduced pressure. Chromatography (SiO₂,5 cm×15 cm, 40–100% EtOAc-hexanes gradient elution) afforded 4 as a white solid.

5. Oleic acid (5: FIG. 1)

Oleic acid was obtained from Aldrich chemical company, CAS #112-80-1.

6. Erucamide (6: FIG. 1)

Erucamide was obtained from Aldrich Chemical Company, CAS #28,057-7.

7. Methyl-8-hydroxy-octanoate (7: Scheme 3)

A solution of suberic acid monomethyl ester (1.5 g, 7.97 mmol, 1.0 equiv.) in tetrahydrofuran (THF) (32.0 mL, .25M) at −20° C. was treated dropwise with BH₃.THF (IM solution in THF, 7.97 mL, 7.97 mmol, 1.0 equiv.). The reaction mixture was stirred overnight and was subsequently allowed to reach room temperature. The reaction mixture was then diluted with ethyl acetate (100 mL) and quenched with methanol (10 mL) and 10% HCl (10 mL). Extraction with NaHCO₃ (1×20 mL), water (2×10 mL), and brine (1×10 mL), afforded methyl-8-hydroxy-octanoate (7) as a crude white solid.

8. Methyl-8-bromo-octanoate (8: Scheme 3)

A solution of crude methyl-8-hydroxy-octanoate (7, 1.24 g, 7.13 mmol, 1.0 equiv.) in CH₂Cl₂ (15 mL, 0.48 M) at 0° C. was treated successively with CBr₄ (3.07 g, 9.27 mmol, 1.3 equiv.) and PPh₃ (2.61 g, 9.98 mmol, 1.4 equiv.) and the reaction mixture was stirred at 4° C. for 10 h. The reaction mixture was then concentrated under reduced pressure and washed repeatedly with Et₂O (8×10 mL washes). The Et₂O washes were combined and concentrated under reduced pressure. Chromatography (SiO₂,5 cm×15 cm, hexanes) afforded 8 as a clear, colorless oil (1.25 g, 1.69 g theoretical, 74.0%): $^1$H NMR (CDCl₃,250 MHz) δ 3.64 (s, 3H, C(O)OCH₃), 3.38 (t, 2H, J=6.8 Hz, CH₂Br), 2.29 (t, 2H, J=7.4 Hz CH₂C(O)OCH₃), 1.83 (p, 2H, CH₂CH₂Br), 1.63 (m, 2H, CH₂CH₂C(O)OCH₃) 1.47–1.28 (m, 6H, alkyl protons).

9. Methyl-8-triphenylphosphoranyl-octanoate-bromide (9: Scheme 3)

A solution of 8 (1.25 g, 5.23 mmol, 1.0 equiv.) in CH₃CN (4.0 mL, 1.31 M) was treated with triphenylphosphine (1.52 g, 5.75 mmol, 1.1 equiv.) and stirred at reflux for 10 h. Additional triphenylphosphine (0.685 g, 2.61 mmol, 0.5 equiv.) was added to the reaction mixture and stirring was continued at reflux for 5 h. The reaction mixture was concentrated under reduced pressure and washed repeatedly with Et₂O (5×10 mL washes). The remaining residue was then solubilized in the minimum volume of CH₂Cl₂ and concentrated under reduced pressure to afford 9 as a colorless foam (2.20 g, 2.61 g theoretical, 84.3%): 1H NMR (CDCl₃,250 MHz) δ 7.82–7.51 (m, 15H, ArH), 3.70–3.46 (m, 5H, CH₃OC(O)R and CH₂PPh₃), 2.13 (t, 2H, J=7.4 Hz, CH₂C(O)OCH₃, 1.62–1.43 (m, 6H, alkyl protons), 1.30–1.02 (m, 4H, alkyl protons); FABHRMS (NBA) m/e 419.2154 (C₂₇H₃₂BrO2P—Br⁻ requires 419.2140).

10. Methyl-cis-8. 9-octadecenoate (10: Scheme 3

A solution of 9 (0.71 g, 1.42 mmol, 1.0 equiv.) in THF (7.0 mL, 0.2 M) at 25° C. was treated with KHMDS (3.0 mL, 0.5 M solution in THF, 1.5 mmol, 1.06 equiv.) and the reaction mixture was stirred at reflux for 1 h. The reaction mixture was then cooled to −78 ° C., treated with decyl aldehyde (0.321 mL, 1.71 mmol, 1.2 equiv.) warmed to 25° C., and stirred for an additional 30 min. The reaction mixture was then treated with saturated aqueous NH₄Cl and parti-tioned between EtOAc (100 mL) and H₂O (100 mL). The organic layer was dried (Na₂SO₄) and concentrated under reduced pressure. Chromatography (SiO₂,5 cm×15 cm, 0–2% EtOAc-hexanes gradient elution) afforded 10 as a colorless oil (0.290 g, 0.422 g theoretical, 68.7 %): $^1$H NMR (CDCl₃,250 MHz) δ 5.34 (m, 2H, CH═CH), 3.65 (s, 3H, CH₃OC(O)), 2.29 (t, 2H, J=7.4 Hz, CH₂C(O)OCH₃), 2.00 (m, 4H, CH₂CH═CHCH₂), 1.61 (m, 2H, CH₂CH₂C(O)OCH₃), 1.29 (bs, 20 H, alkyl protons), 0.86 (t, 3H, RCH₃).

11. Cis-8,9octadecenoic acid (11: Scheme 3)

A solution of 10 (0.245 g, 0.825 inmol, 1.0 equiv.) in THF-MeOH-H₂O (3-1-1 ratio, 4.1 mL, 0.2 M) at 0° C. was treated with LiOH.H₂O (0.104 g, 2.48 mrmol, 3.0 equiv.). The reaction mixture was warmed to 25° C., stirred for 8 h, and then partitioned between EtOAc (100 mL) and H₂O (100 mL). The organic layer was washed successively with 10% aqueous HCl (100 mL) and saturated aqueous NaCl (100 mL), dried, and concentrated under reduced pressure. Chromatography (SiO₂,5cm×15 cm, 10–30% EtOAc-hexanes gradient elution) afforded 11 as a colorless oil (0.156 g, 0.233 g theoretical, 67.0%): $^1$H NMR (CDCl₃,250 MHz) δ 5.34 (m, 2H, CH═CH), 2.34 (t, 2H, J=7.4 Hz, CH₂COOH), 2.01 (m, 4H, CH₂CH═CHCH₂), 1.61 (m, 2H, CH₂CH₂COOH), 1.47–1.23 (m, 20 H, alkyl protons), 0.87 (t, 3H, RCH₃).

12. 18-Hemisuccinate-cis-9,10-octadecenoamide (12: Scheme 4)

A solution of 18 (0.047 g, 0.160 M, 1.0 equiv) in CH₂Cl₂—CHCl₃ (3–1, 1.60 mL, 0.1M) was treated successively with Et₃N (0.045 mL, 0.320 mmol, 2.0 equiv), succinic anhydride (0.033 g, 0.320 mmol, 2.0 equiv) and DMAP (0.002 g, 0.016 mmol, 0.1 equiv), and the reaction mixture was stirred at 25° C. for 10 h. The reaction mixture was then partitioned between CH₂Cl₂ (50 mL) and H₂O (50 mL), and the organic layer was washed successively with 10% aqueous HCl (50 mL) and saturated aqueous NaCl (50 mL), dried (Na₂SO₄), and concentrated under reduced pressure. Chromatography (SiO₂,3 cm×15 cm, 0–10% MeOH-EtOAc) afforded 12 as a white solid (0.051 g, 0.063 theoretical, 80.3%): $^1$H NMR (CDCl₃,250 MHz) δ 6.95 (b s, 1H, H₂NC(O)), 5.72 (b s, 1H, H₂NC(O)), 5.34 (m, 2H, CH═CH), 4.08 (t, 3H, J=6.6 Hz, CH₂OC(O)R), 2.61 (m, 4H, ROC(O)CH₂CH₂COOH), 2.21 (t, 2H, J=7.5 Hz, CH₂C (O)NH₂), 2.00 (m, 4H, CH₂CH═CHCH₂), 1.70–1.52 (m, 4H, CH2CH₂C(O)NH₂ and CH₂CH₂OH), 1.29 (b s, 18H, alkyl protons); FABHRMS (NBA) m/e 398.2893 (C₂₂H₃₉NO₅ +H+requires 398.2906).

13. Methyl-9-bromo-nonanoate (13: Scheme 4)

A solution of methyl-9-hydroxy-nonanoate (1.1 g, 5.85 mmol, 1.0 equiv) in CH₂Cl₂ (30 mL, 0.2 M) at 0° C. was treated successively with CBr₄ (2.5 g, 7.54 mmol, 1.3 equiv) and PPh₃ (2.15 g, 8.19 mmol, 1.4 equiv) and the reaction mixture was stirred at 4° C. for 10 h. The reaction mixture was then concenctrated under reduced pressure and washed repeatedly with Et₂O (8×10 mL washes). The Et₂o washes were combined and concentrated under reduced pressure. Chromatography (SiO₂,5 cm×15 cm, hexanes) afforded 13 as a clear, colorless oil (1.02 g, 1.47 g theoretical, 69.5 %): $^1$H NMR (CDCl₃,250MHz) d 3.64 (s, 3H, C(O)OCH₃), 3.38 (t, 2H, J=6.8 Hz, CH₂Br), 2.29 (t, 2H, J=7.4 Hz CH₂C(O) OCH₃), 1.83 (p, 2H, CH₂CH₂Br), 1.63 (m, 2H, CH₂CH₂C (O)OCH₃) 1.47–1.28 (m, 8H, alkyl protons).

14. Methyl-9-triphenylphosphoranyl-nonanoate-bromide (14: Scheme 4)

A solution of 13 (1.02 g, 4.06 mmol, 1.0 equiv) in CH₃CN (3.5 mL, 1.16 M) was treated with triphenylphosphine (1.17 g, 4.47 mmol, 1.1 equiv) and stirred at reflux for 10 h.

Additional triphenylphosphine (0.532 g, 2.03 mmol, 0.5 equiv) was added to the reaction mixture and stirring was continued at reflux for 5 h. The reaction mixture was concentrated under reduced pressure and washed repeatedly with $Et_2O$ (5×10 mL washes). The remaining residue was then solubilized in the minimum volume of $CH_2Cl_2$ and concentrated under reduced pressure to afford 14 as a colorless foam (1.90 g, 2.08 g theoretical, 91.3%): $^1$H NMR ($CDCl_3$, 250 MHz) δ 7.82–7.51 (m, 15H, ArH), 3.70–3.46 (m, 5H, $CH_3OC(O)R$ and $CH_2PPh_3$), 2.13 (t, 2H, J=7.4 Hz, $—CH_2C(O)OCH_3$), 1.62–1.02 (m, 12H, alkyl protons); FABHRMS (NBA) m/e 433.2312 ($C_{28}H_{34}BrO_2P—Br^-$ requires 433.2296).

15. Methyl-18-t-butyldiphenysilyloxy-cis-9,10 octadecenoate (15: Scheme 4)

A solution of 14 (1.0 g, 1.95 mmol, 1.0 equiv) in THF (6.5 mL, 0.3 M) at 25° C. was treated with KHMDS (3.9 mL, 0.5 M solution in THF, 1.95 mmol, 1.0 equiv) and the reaction mixture was stirred at reflux for 1 h. The reaction mixture was then cooled to −78° C., treated with 3 (0.93 g, 2.35 mmol, 1.2 equiv), warmed to 25° C., and stirred for an additional 30 min. The reaction mixture was then treated with saturated aqueous $NH_4Cl$ and partitioned between EtOAc (100 mL) and $H_2O$ (100 mL). The organic layer was dried ($Na_2SO_4$) and concentrated under reduced pressure. Chromatography ($SiO_2$, 5 cm×15 cm, 0–2% EtOAc-hexanes gradient elution) afforded 15 as a colorless oil (0.82 g, 1.07 g theoretical, 76.3%): $^1$H NMR ($CDCl_3$, 250 MHz) δ 7.67 (m, 4H, ArH), 7.41 (m, 6H, ArH), 5.34 (m, 2H, CH=CH), 3.65 (m, 5H, $CH_3OC(O)$ and $CH_2OTBDPS$), 2.29 (t, 2H, J=7.4 Hz, $CH_2C(O)OCH3$), 2.00 (m, 4H, $CH_2CH=CHCH_2$), 1.55 (m, 4H, $CH_2CH_2C(O)OCH_3$ and $CH_2CH_2OTBDPS$), 1.29 (b s, 18H, alkyl protons), 1.04 (s, 9H, $(CH_3)_3C$).

16. 18-T-butyldiphenylsilyloxy-cis-9,10-octadecenoic acid (16: Scheme 4)

A solution of 5 (0.81 g, 1.47 mmol, 1.0 equiv) in THF-MeOH-$H_2O$ (3-1-1 ratio, 7.3 mL, 0.2 M) at 0° C. was treated with $LiOH\cdot H_2O$ (0.188 g, 4.48 mmol, 3.0 equiv). The reaction mixture was warmed to 25° C., stirred for 8 h, and then partitioned between EtOAc (100 mL) and $H_2O$ (100 mL). The organic layer was washed successively with 10% aqueous HCl (100 mL) and saturated aqueous NaCl (100 mL), dried, and concentrated under reduced pressure. Chromatography ($SiO_2$, 5 cm×15 cm, 10–30% EtOAc-hexanes gradient elution) afforded 16 as a colorless oil (0.700 g, 0.790 g theoretical, 88.7%): $^1$H NMR ($CDCl_3$, 250 MHz) δ 7.67 (m, 4H, ArH), 7.41 (m, 6H, ArH), 5.34 (m, 2H, CH=CH), 3.65 (t, 3H, J=6.5 Hz, $CH_2OTBDPS$), 2.34 (t, 2H, J=7.4 Hz, $CH_2COOH$), 2.00 (m, 4H, $CH_2CH=CHCH_2$), 1.65–1.50 (m, 4H, $CH_2CH_2COOH$ and $CH_2CH_2OTBDPS$), 1.47–1.23 (m, 18H, alkyl protons), 1.05 (s, 9H, $(CH3)_3C$); FABHRMS (NBA/CsI) m/e 669.2772 ($C_{34}H_{52}O_3Si+Cs^+$ requires 669.2740).

17. 18-T-butyldiphenylsilyloxy-cis-9,10-octadecenoamide (17: Scheme 4)

A solution of 16 (0.685 g, 1.28 mmol, 1.0 equiv) in $CH_2Cl_2$ (4.3 mL, 0.3 M) at 0° C. was treated dropwise with oxalyl chloride (1.92 mL, 2 M solution in $CH_2Cl_2$, 3.84 mmol, 3.0 equiv). The reaction mixture was stirred at 25° C. for 4 h, concentrated under reduced pressure, cooled to 0° C., and treated with saturated aqueous $NH_4OH$ (2.0 mL). The reaction mixture was then partitioned between EtOAc (100 mL) and $H_2O$ (100 mL), and the organic layer was dried ($Na_2SO_4$) and concentrated under reduced pressure. Chromatography ($SiO_2$, 5 cm×15 cm, 40–100% EtOAc-hexanes gradient elution) afforded 17 as a colorless oil (0.520 g, 0.684 g, 76.0%): $^1$H NMR ($CDCl_3$, 250 MHz) δ 7.67 (m, 4H, ArH), 7.41 (m, 6H, ArH), 5.70–5.34 (m, 4H, $H_2NC(O)$ and CH=CH), 3.65 (t, 3H, J=6.5 Hz, $CH_2OTBDPS$), 2.21 (t, 2H, J=7.5 Hz, $CH_2C(O)NH_2$), 2.00 (m, 4H, $CH_2CH=CHCH_2$), 1.65–1.50 (m, 4H, $CH_2CH_2C(O)NH_2$ and $CH_2CH_2OTBDPS$), 1.47–1.23 (m, 18H, alkyl protons), 1.05 (s, 9H, $(CH_3)_3C$); FABHRMS (NBA/CsI m/e 668.2929 ($C_{34}H_{53}O_2NSi+Cs^+$ requires 668.2900).

18. 18-Hydroxy-cis-9,10-octadecenoamide (18: Scheme 4)

A solution of 17 (0.185 g, 0.345 mmol, 1.0 equiv) in THF (1.1 mL, 0.31 M) was treated with tetrabutylammoniumfluoride (0.69 mL, 1.0 M solution in THF, 0.69 mmol, 2.0 equiv) and the reaction mixture was stirred at 25° C. for 2 h. The reaction mixture was then partitioned between EtOAc (50 mL) and $H_2O$ (50 mL), and the organic layer was dried ($Na_2SO_4$) and concentrated under reduced pressure . Chromatography ($SiO_2$, 3 cm×15 cm, 0–5% MeOH-EtOAc gradient elution) afforded 18 as a white solid (0.097 g, 0.103 g theoretical, 94.6%): $^1$H NMR ($CDCl_3$, 250 MHz) δ 5.65–5.34 (m, 4H, $H_2NC(O)$ and CH=CH), 3.62 (t, 3H, J=6.5 Hz, $CH_2OH$), 2.21 (t, 2H, J=7.5 Hz, $CH_2C(O)NH_2$), 2.00 (m, 4H, $CH_2CH=CHCH_2$), 1.65–1.50 (m, 4H, $CH_2CH_2C(O)NH_2$ and $CH_2CH_2OH$), 1.29 (b s, 18H, alkyl protons); FABHRMS (NBA) 298.2732 ($C_{18}H_{35}NO_2+H^+$ requires 298.2746).

Figure 5:
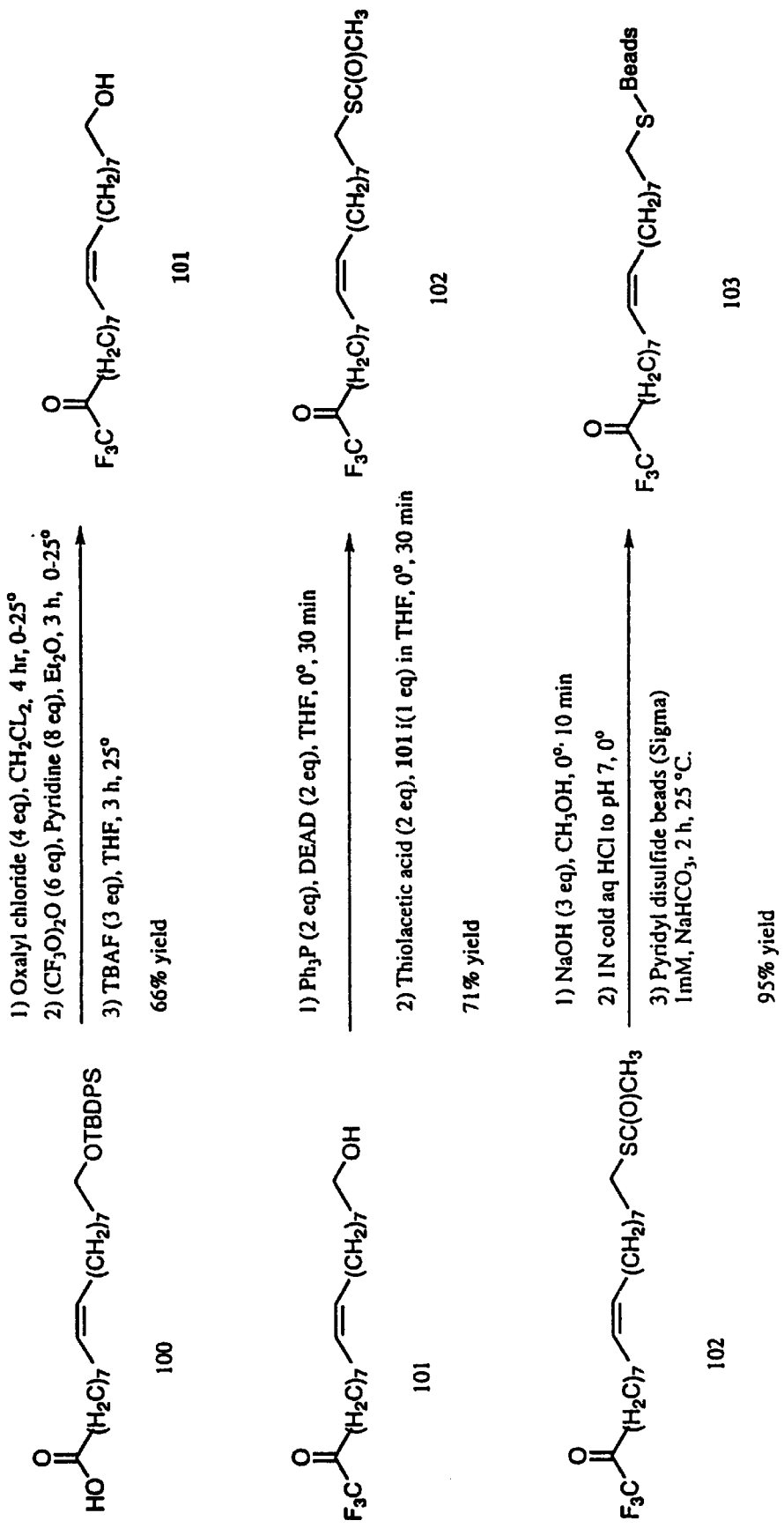
FIG. 5 illustrates the synthetic protocol for the synthesis of the trifluoroketone inhibitor and subsequent attachment of the inhibitor to the disulfide-derivatized solid support using pyridyl disulfide beads.

19. Synthesis of Compound 100 (FIG. 5)

Methyl-9-t-butyldiphenylsilyloxy-nonanoate (intermediate for compound 100: FIG. 5). A solution of methyl-9-hydroxy-nonanoate (0.838 g, 4.46 mmol, 1.0 equiv: Aldrich) in $CH_2Cl_2$ (15 mL, 0.3 M) was treated successively with $Et_3N$ (0.75 mL, 5.38 mmol, 1.2 equiv), t-butylchlorodiphenylsilane (1.28 mL, 4.93 mmol, 1.1 equiv), and DMAP (0.180 g, 1.48 mmol, 0.33 equiv), and the reaction mixture was stirred at 25° C. for 12 h. Saturated aqueous $NH_4Cl$ was added to the reaction mixture and the mixture was partitioned between $CH_2Cl_2$ (100 mL) and $H_2O$ (100 mL). The organic layer was dried ($Na_2SO_4$) and concentrated under reduced pressure. Chromatography ($SiO_2$, 5 cm×15 cm, 0–5% EtOAc-hexanes gradient elution ) afforded the intermeidate as a clear, colorless oil (1.22g, 1.831 theoretical, 64.1%): $^1$H NMR ($CDCl_3$, 250 MHz) δ 7.66 (m, 4H, ArH), 7.38 (m, 6H, ArH), 3.67–3.62 (m, 5H, $C(O)OCH_3$ and $CH_2OTBDPS$), 2.30 (t, 2H, J=7.4 Hz, $CH_2C(O)OCH_3$), 1.58 (m, 4H, $CH_2CH_2OTBDPS$ and $CH_2CH_2C(O)OCH_3$), 1.28 (b s, 8H, alkyl protons), 1.05 (s, 9H, $C(CH_3)_3$)

20. Methyl-9-bromo-nonanoate (Intermediate for Compound 100: FIG. 5)

A solution of methyl-9-hydroxy-nonanoate (1.1 g, 5.85 mmol, 1.0 equiv) in $CH_2Cl_2$ (30 mL, 0.2 M) at 0° C. was treated successively with $CBr_4$ (2.5 g, 7.54 mmol, 1.3 equiv) and $PPh_3$ (2.15 g, 8.19 mmol, 1.4 equiv) and the reaction mixture was stirred at 4° C. for 10 h. The reaction mixture was then concenctrated under reduced pressure and washed repeatedly with $Et_2O$ (8×10 mL washes). The $Et_2O$ washes were combined and concentrated under reduced pressure. Chromatography ($SiO_2$, 5 cm×15 cm, hexanes) afforded the intermediate as a clear, colorless oil (1.02 g, 1.47 g theorectical, 69.5 %): $^1$H NMR ($CDCl_3$, 250 MHz) d 3.64 (s, 3H, $C(O)OCH_3$), 3.38 (t, 2H, J=6.8 Hz, $CH_2Br$), 2.29 (t, 2H, J=7.4 Hz $CH_2C(O)OCH_3$), 1.83 (p, 2H, $CH_2CH_2Br$), 1.63 (m, 2H, $CH_2CH_2C(O)OCH_3$) 1.47–1.28 (m, 8H, alkyl protons).

21. 9-T-butyldiphenylsilyloxy-nonanal (Intermediate for Compound 100: FIG. 5)

A solution of 1 (1.25 g, 2.93 mmol, 1.0 equiv) in toluene (9.80 mL, 3.0 N) at −78° C. was treated dropwise with DIBAL-H (4.40 mL, 1.0 M solution in hexanes, 4.40 mmol, 1.5 equiv). The reaction mixture was stirred at −78° C. for 30 min. The reaction mixture was then treated dropwise with MeOH (2 mL) and partitioned between EtOAc (100 mL) and $H_2O$ (100 mL). The organic layer was washed with 10 % aqueous HCl (100 mL), dried ($Na_2SO_4$), and concentrated under reduced pressure. Chromatography ($SiO_2$,5 cm×15 cm, 0–5 % EtOAc-hexanes gradient elution) afforded 3 as a colorless oil (1.1 g, 94.9 %): $^1$H NMR ($CDCl_3$,250 MHz) δ 9.76 (t, 1H, J=1.8 Hz, HC(O)R), 7.67 (m, 4H, ArH), 7.40 (m, 6H, ArH), 3.65 (t, 2H, J=6.4 Hz, $CH_2OTBDPS$), 2.41 (t of d, 2H J=1.8 and 7.3 Hz, $CH_2C(O)H$), 1.58 (m, 4H, $CH_2CH_2OTBDPS$ and $CH_2CH_2C(O)H$), 1.29 (b s, 8H, alkyl protons), 1.05 (s, 9H, $(CH_3)_3C$); FABHRMS (NBA/CsI) m/e 529.1560 ($C25H36O2Si+Cs^+$ requires 529.1539).

22. Methyl-9-triphenylphosphoranyl-nonanoate Bromide (Intermediate for Compound 100: FIG. 5)

A solution of 9-T-butyldiphenylsilyloxy-nonanal (1.02 g, 4.06 mmol, 1.0 equiv) in $CH_3CN$ (3.5 mL, 1.16 M) was treated with triphenylphosphine (1.17 g, 4.47 mmol, 1.1 equiv) and stirred at reflux for 10 h. Additional triphenylphosphine (0.532 g, 2.03 mmol, 0.5 equiv) was added to the reaction mixture and stirring was continued at reflux for 5 h. The reaction mixture was concentrated under reduced pressure and washed repeatedly with $Et_2O$ (5×10 mL washes). The remaining residue was then solubilized in the minimum volume of $CH_2Cl_2$ and concentrated under reduced pressure to afford the intermediate as a colorless foam (1.90 g, 2.08 g theoretical, 91.3%): $^1$H NMR ($CDCl_3$, 250 MHz) δ 7.82–7.51 (m, 15H, ArH), 3.70–3.46 (m, 5H, $CH_3OC(O)R$ and $CH_2PPh_3$), 2.13 (t, 2H, J=7.4 Hz, $CH_2C(O)OCH_3$), 1.62–1.02 (m, 12H, alkyl protons); FABHRMS (NBA) m/e 433.2312 ($C_{28}H_{34}BrO_2P$—$Br^-$ requires 433.2296).

23. Methyl-18-t-butyldiphenysilyloxy-cis-9,10-octadecenoate (Intermediate for Compound 100: FIG. 5)

A solution of (1.0 g, 1.95 mmol, 1.0 eguiv) in THF (6.5 mL, 0.3 M) at 25 ° C. was treated with KHMDS (3.9 mL, 0.5 M solution in THF, 1.95 mmol, 1.0 equiv) and the reaction mixture was stirred at reflux for 1 h. The reaction mixture was then cooled to −78 ° C., treated with 3 (0.93 g, 2.35 mmol, 1.2 equiv), warmed to 25° C., and stirred for an additional 30 min.

The reaction mixture was then treated with saturated aqueous $NH_4Cl$ and partitioned between EtOAc (100 mL) and $H_2O$ (100 mL). The organic layer was dried ($Na_2SO_4$) and concentrated under reduced pressure. Chromatography ($Sio_2$,5 cm×15 cm, 0–2% EtOAc-hexanes gradient elution) afforded the intermediate as a colorless oil (0.82 g, 1.07 g theoretical, 76.3%): $^1$H NMR ($CDCl_3$,250 MHz) δ 7.67 (m, 4H, ArH), 7.41 (m, 6H, ArH), 5.34 (m, 2H, CH═CH), 3.65 (m, 5H, $CH_3OC(O)$ and $CH_2OTBDPS$), 2.29 (t, 2H, J=7.4 Hz, $CH_2C(O)OCH_3$), 2.00 (m, 4H, $CH_2CH$═$CHCH_2$), 1.55 (m, 4H, $CH_2CH_2C(O)OCH_3$ and $CH_2CH_2OTBDPS$), 1.29 (b s, 18H, alkyl protons), 1.04 (s, 9H, $(CH_3)_3C$).

24. 18-T-butyldiphenylsilyloxy-cis-9,10-octadecenoic acid (Compound 100: FIG. 5)

A solution of Methyl-18-t-butyldiphenysilyloxy-cis-9,10-octadecenoate (0.81 g, 1.47 mmol, 1.0 equiv) in THF-MeOH-$H_2O$ (3-1-1 ratio, 7.3 mL, 0.2 M) at 0° C. was treated with LiOH.$H_2O$ (0.188 g, 4.48 mmol, 3.0 equiv). The reaction mixture was warmed to 25° C., stirred for 8 h, and then partitioned between EtOAc (100 mL) and $H_2O$ (100 mL). The organic layer was washed successively with 10% aqueous HCl (100 mL) and saturated aqueous NaCl (100 mL), dried, and concentrated under reduced pressure. Chromatography ($SiO_2$,5 cm×15 cm, 10–30% EtOAc-hexanes gradient elution) afforded 100 as a colorless oil (0.700 g, 0.790 g theoretical, 88.7%): $^1$H NMR ($CDCl_3$,250 MHz) δ 7.67 (m, 4H, ArH), 7.41 (m, 6H, ArH), 5.34 (m, 2H, CH═CH), 3.65 (t, 3H, J=6.5 Hz, $CH_2OTBDPS$), 2.34 (t, 2H, J=7.4 Hz, $CH_2COOH$), 2.00 (m, 4H, $CH_2CH$═$CHCH_2$), 1.65–1.50 (m, 4H, $CH_2CH_2COOH$ and $CH_2CH_2OTBDPS$), 1.47–1.23 (m, 18H, alkyl protons), 1.05 (s, 9H, $(CH_3)_3C$); FABHRMS (NBA/CsI) m/e 669.2772 ($C_{34}H_{52}O_3Si+Cs^+$ requires 669.2740). 25. Synthesis of Compound 101 (FIG. 5)

Step 1.

A solution of 100 (1.0 equiv) in $CH_2Cl_2$ (0.3 M) at 0° C. was treated dropwise with oxalyl chloride (4.0 equiv). The reaction mixture was stirred at 25° C. for 4 h, concentrated under reduced pressure, cooled to 0° C., and treated with saturated aqueous $NH_4OH$ (2.0 mL). The reaction mixture was then partitioned between EtOAc (100 mL) and $H_2O$ (100 mL), and the organic layer was dried ($Na_2SO_4$) and concentrated under reduced pressure.

Step 2.

A solution of the above step 1 intermediate compound (1.0 equiv) in ether (0.3 M) at 0° C. was treated dropwise with pyridine (8.0 equiv.) followed by trifluoroaceticanhydride (6.0 equiv; Aldrich). The reaction mixture was stirred at 25° C. for 3 h, concentrated under reduced pressure, cooled to 0° C., and treated with saturated aqueous $NH_4OH$ (2.0 mL). The reaction mixture was then partitioned between EtOAc (100 mL) and $H_2O$ (100 mL), and the organic layer was dried ($Na_2SO_4$) and concentrated under reduced pressure.

Step 3.

A solution of the above step 2 intermediate compound (1.0 equiv) in THF (0.31 M) was treated with tetrabutylammoniumfluoride (1.0 M solution in THF, 3.0 equiv) and the reaction mixture was stirred at 25° C. for 3 h. The reaction mixture was then partitioned between EtOAc (50 mL) and $H_2O$ (50 mL), and the organic layer was dried ($Na_2SO_4$) and concentrated under reduced pressure. Product was purified by standard chromatographic conditions and yielded compound 101 in 66% overall yield for the 3 steps.

26. Synthesis of Compound 102 (FIG. 5)

Step 1.

A solution of 101 (1.0 equiv.) in THF (0.1 M) was treated with triphenylphosphine (2.0 equiv.), followed by diethylazodicarboxylate solution (1.0 THF solution, DEAD, 2.0 equiv., Aldrich) and at 0° C. for 30 minutes. The reaction mixture was concentrated under reduced pressure and washed repeatedly with $Et_2O$ (5×10 mL washes). The remaining residue was then solubilized in the minimum volume of $CH_2Cl_2$ and concentrated under reduced pressure.

Step 2.

A solution of the above step 1 compound (1.0 equiv.) in THF (0.10 M) was treated with thiolacetic acid (2.0 equiv.; Aldrich) at 0° C. for 30 minutes. The reaction mixture was concentrated under reduced pressure and washed repeatedly with $Et_2O$ (5×10 mL washes). The remaining residue was then solubilized in the minimum volume of $CH_2Cl_2$ and concentrated under reduced pressure. Product was purified by standard chromatographic conditions and yielded compound 102 in 71% overall yield for the 2 steps.

27. Synthesis of Compound 103 (FIGS. 4 & 5)

Step 1.

A solution of 102 (1.0 equiv) in MeOH/Water (2:1 mixture, total concentration 0.20 M) at 0° C. was treated with NaOH (3.0 equiv) and stirred for 10 minutes, and then partitioned between EtOAc (100 mL) and water (100 mL). The organic layer was washed successively with 10% aqueous HCl (100 mL) and saturated aqueous NaCl (100 mL), dried, and concentrated under reduced pressure.

Step 2.

A solution of the above step 1 compound (1.0 equiv) in aqueous 1N HCl at 0° C. was stirred until the reaction mixuture achieved a pH of 7.0, and then the mixture was partitioned between EtOAc (100 mL) and water (100 mL). The organic layer was washed successively with saturated aqueous NaCl (100 mL), dried, and concentrated under reduced pressure.

Step 3. A solution of the above step 2 compound (1.0 equiv.) in aqeos 1 mM $NaHCO_3$ at 25° C. was treated with Pyridyl disulfide beads (1.1 equiv. Aldrich) and stirred for 2 hours. The beads were subsequently washed with excess saturated $NaHCO_3$(3×), water (3×) and brine (1×). Standard filtration obtained the activated beads (compound 103) which were then packed into the column for affinity chromatography of the enzyme as discussed supra using this CF3-inhibitor linked to activated pyridyl disulphide beads.

D. Cloning of Cis-9,10-Octadecenoamidase cDNA

1. Cis-9,10-Octadecenoamidase cDNA Obtained from Rat Liver mRNA

To obtain a CDNA clone for cis-9,10-octadecenoamidase from CDNA library generated from rat liver mRNA, degenerate oligonucleotide primers were designed based on the amino acid residue sequence of cis-9,10-octadecenoamidase polypeptide fragment obtained from a trypsin digest. Briefly, the cis-9,10-octadecenoamidase, purified as described above, was subjected to a trypsin digest to form internal polypeptide fragments as performed by Worchester Foundation, Worchester, Pa. The resultant polypeptide fragments were purified by HPLC and seven HPLC fractions showing discrete peptide masses as measured by Matrix-Assisted-Laser-Desorption-Ionization with Time-of-Flight (MALDI TOF, PerSeptive Biosystems Linear Instrument) mass spectrometry were selected for microsequencing. Seven polypeptide fragments were microsequenced having lengths ranging from 12 to 25 amino acid residues as indicated in FIG. 9 indicated by seven discontinuous singly underlined regions in the complete rat cis-9,10-octadecenoamidase amino acid residue sequence. Each peptide possessed the required lysine or arginine residue at its C-terminus indicating that the tryptic digest proceeded with the anticipated selectivity.

The degenerate oligonucleotide primers were designed to incorporate a unique restriction site into the 5' ends of the primers that functioned as either forward and the backward primers. The forward primers are also referred to as upstream, sense or 5' primers. The backward primers are also referred to as downstream, anti-sense or 3' primers. The restriction sites were incorporated into the polymerase chain reaction (PCR) products to allow for insertion into the multiple cloning site of a sequencing vector as described below.

The synthesized 5' and 3' degenerate oligonucleotides were designed respectively corresponding to portions of sequenced peptides 1 and 2 as shown in FIG. 9 as indicated by the first two discontinuous singly underlined amino acid residue sequences. The degenerate nucleotides are indicated by IUPAC codes N=A, C, G or T and R =A or G. The nucleotide sequence of the 5' degenerate primer corresponding to peptide 1 was 5' CGGAATTCGGNGGNGARG-GNGC3' (SEQ ID NO 3) incorporating an EcoRI restriction site and translating into the amino acid sequence GGEGA (SEQ ID NO 4). The nucleotide sequence of the 3' degenerate primer that corresponded to peptide 2 was 5' CGG-GATCCGGCATNGTRTARTTRTC3' (SEQ ID NO 33) incorporating an BamHI restriction site and translating into the amino acid sequence DNYTMP (SEQ ID NO 34).

To amplify regions of cDNA encoding cis-9,10-octadecenoamidase, rat liver mRNA was reversed transcribed into cDNA for use a template in PCR with selected pairs of degenerate oligonucleotide primers described above. PCR was performed under conditions well known to one of ordinary skill in the art with each cycle of 40 total cycles having the temperatures 94° C. for 30 seconds, 60° C. for 45 seconds and 72° C. for 60 seconds.

Of the cloned PCR fragments, three were selected for sequencing. The three PCR fragments were 350 base pairs (bp), 400 bp and 750 bp. Sequencing of these cis-9,10-octadecenoamidase-encoding cDNA fragments showed that the 750 bp fragment contained the sequences of both the 350 and 400 bp fragments.

The 350 bp cDNA fragment obtained by PCR was then labeled internally and used as a probe for Northern analysis on electrophoresed rat liver mRNA. The probe hybridized to a fragment approximately 2.5 to 3.0 kilobases (kb) in length, which is the expected size of the cis-9,10-octadecenoamidase mRNA that encodes a 60 kDa protein.

To isolate a cDNA clone encoding the complete cis-9,10-octadecenoamidase protein, the 350 bp probe was then internally labeled with $^{32}P$ used to screen a λgtll cDNA library from rat liver mRNA obtained from Clontech (Palo Alto, Calif.). For screening, the amplified 350 bp fragment was first digested with EcoRI and BamHI for directional cloning into a similarly digested pBluescript II SK(−) (Stratagene, La Jolla, CA). The resultant sequence indicated that the 350 bp fragment encoded the peptides 1 and 2 from which the degenerate oligonucleotide primers were designed confirming the accuracy of the PCR and amplification of the desired clone. The methods for cloning the cis-9,10-octadecenoamidase cDNA of this invention are techniques well known to one of ordinary skill in the art and are described, for example, in "Current Protocols in Molecular Biology", eds. Ausebel et al., Wiley & Sons, Inc., New York (1989), the disclosures of which are hereby incorporated by reference.

Four positive clones were identified from a screening of $4.5 \times 10^5$ plaques. Two clones of 2.7 kb in length and 1 of 2.0 kb in length, were obtained. The partial sequence of one of the 2.7 kb clones, designated p60, indicates that the clone does contain cis-9,10-octadecenoamidase-specific sequences.

The rat liver cDNA clone designated p60 obtained above has been deposited with American Type Culture Collection (ATCC) on or before Jun. 12, 1996 and has been assigned the ATCC accession number 97605. This deposit was made under the provisions of the Budapest Treaty on the International Recognition of the Deposit of Microorganisms for the Purpose of Patent Procedure and the Regulations thereunder (Budapest Treaty). This assures maintenance of a viable plasmid for 30 years from the date of each deposit. The plasmid will be made available by ATCC under the terms of the Budapest Treaty which assures permanent and unrestricted availability of the progeny of the plasmid to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the plasmid deposit should die or be lost or destroyed when cultivated under suitable conditions, it will be promptly replaced on notification with a viable specimen of the same plasmid. Availability of the deposit is not to be construed as a license to practice the invention in contravention of the rights granted under the authority of any government in accordance with its patent laws.

A partial nucleotide sequence of the top strand of the p60 cDNA clone containing 780 nucleotides described above is listed in SEQ ID NO 1 along with the deduced amino acid residue sequence. The encoded amino acid residue sequence is listed separately in SEQ ID NO 2. In order to show the amino acid residue encoded by each triplet codon in the Sequence Listing, a stop codon, TAA, was added at positions 781 to 783 to allow for the coding sequence (CDS) function in the Patentin program used to prepare the Sequence Listing. In other words, the stop codon is artificially inserted into the nucleotide sequence shown in SEQ ID NO 1 to facilitate the translation of the cDNA coding sequence into an amino acid sequence.

The actual position of the cis-9,10-octadecenoamidase nucleotide position within a complete cDNA clone is evident from the complete cDNA sequence as described below.

The two largest positive cDNA clones were then cloned into pBluescript II SK(+) and sequenced. One clone encoded a partially processed transcript containing the full coding sequence of the oleamide amidase with an additional 200 bp of intronic sequence. The other clone encoded a fully processed oleamide amidase transcript but fused to the 5' end of the clone was a 300 bp fragment encoding rRNA. Fusion of the two clones through an internal overlapping HindIII restriction site generated the full-length rat cis-9,10-octadecenoamidase also referred to as fatty acid amide hydrolase abbreviated as FAAH. The clone was sequenced with sequencing primers that were synthesized on a Beckman Oligo1000M Synthesizer.

The resultant full length rat cDNA FAAH clone, also referred to as rFAAH cDNA, contained 2473 bp, which contained a single 1.73 kb open reading frame encoding 63.3 kDa of protein sequence as shown in FIGS. 10-1 to 10-5. The double-stranded rat FAAH cDNA sequence is available by GenBank with Accession Number U72497. The encoded rat FAAH protein is also referred to as rFAAH protein. The clone contained 50 bp of sequence 5' to the first ATG designation the start of the open reading frame. The clone also contained 685 bp of 3' untranslated region between the first stop codon indicating the end of the open reading frame and the poly A tail.

In FIGS. 10-1 through 10-5, the encoded amino acid residue is positioned directly underneath the second nucleotide of a triplet codon. For example, at the initiation site where ATG encodes methionine (M), the A nucleotide begins at nucleotide position 50 and the G nucleotide is 52. The encoded M is located underneath the T nucleotide at nucleotide position 51. As presented in the figure, thus, the indicated triplet codons are not as indicated. The top and bottom strands of the cDNA sequence are also respectively listed as SEQ ID NOs 35 and 37. The encoded amino acid sequence is shown in with the top strand in SEQ ID NO 35 and again by itself in SEQ ID NO 36.

Although the 50 bases of nucleotide sequence upstream of the first ATG did not possess an in-frame stop codon, the following several lines of evidence supported the 2.47 kb CDNA encoding the complete oleamide hydrolase protein sequence: 1) The size of the cDNA matched closely the predicted size of the mRNA transcript as estimated by Northern blot (FIG. 12B as discussed below); 2) The sequence surrounding the first ATG possessed the required consensus sequence for eukaryotic translation initiation sites, in particular, an A is present at the −3 position and a G is present at the +4 position; and 3) When transiently transfected with oleamide hydrolase cDNA, COS-7 cells translated a functional protein product that comigrated with affinity isolated oleamide hydrolase on SDS-PAGE (FIG. 12B, lane 1 and discussed below).

Database searches with the oleamide amidase protein sequence (FAAH) identified strong homology to several amidase enzyme sequences from organisms as divergent as *Agrobacterium tumefaciens* (Klee et al., *Proc. Nat . Acad. Sci., USA,* 81:1728–1732, 1984), *Pseudomonas savastanoi* (Yamada et al., *Proc. Natl. Acad. Sci., USA,* 82:6522–6526, 1985); *Aspergillus nidulans* (Corrick et al., *Gene,* 53:63–71, 1987), *Saccharomyces cerevisiae* (Chang et al., *Nuc. Acids Res.,* 18:7180, 1990), *Caenorhabditis elegans* (Wilson et al., *Nature,* 368:32–38, 1994), and *Gallus domesticus* (Ettinger et al., *Arch. Biochem. Biophys.,* 316:14–19, 1995). These amidases collectively compose a recently defined enzyme family (Mayaux et al., *J. Bacteriol.,* 172:6764–6773, 1990) whose members all share a common signature sequence as shown in FIG. 11. The encoded amino acids beginning at position 215 and extending through 246 of the rat fatty acid amide hydrolase (oleamide hydrolase or FAAH) contain residues that are found in a family of D M amidases. The sequence in the cis-9,10-octadecenoamidase rat protein of this invention has is shown in SEQ ID NO 36 at amino acid positions 215 to 246. The alignment over the amidase signature sequence region of the rat FAAH with several other representative amidases reveals that the signature sequence is completely conserved among the amidase family members. Those amino acids are shown in bold faced type in the figure and the relative amino acid position of the signature sequence in each amidase is given by the numbers just preceding and following the sequence information. The assigned SEQ ID NOs for each of the sequences are listed in the legend to the Figure in Brief Description of the Figures.

To our knowledge an, oleamide amidase also referred to as FAAH is the first mammalian member of this enzyme family to have been molecularly characterized.

Hydropathicity plot and transmembrane domain searches (TMpred and PSORT programs) of the rat FAAH sequence were conducted, and each search indicated a strong putative transmembrane domain from amino acids 13–29 (bold type in FIG. 9). The 50 amino acid region surrounding and encompassing the putative transmembrane domain of rat FAAH shares no homology with protein sequences of other amidase family members, indicating that one of the unique modifications of the rat amidase may be its integration into the membrane. Interestingly, additional analysis of the FAAH sequence revealed a polyproline segment, amino acids 307–315 (double underlined in FIG. 9), that contains a precise match from positions 310 to 315 to the consensus class II SH3 domain binding sequence, PPLPXR (SEQ ID NO 38) Feng et al, *Science,* 266:1241–1246, 1994), suggesting that other proteins may interact with FAAH to regulate its activity (Pawson, *Nature,* 373:573–580, 1995) and/or subcellular localization (Rotin et al, *EMBO J.,* 13:4440–4450, 1994).

Southern and Northern blot analyses were conducted with an internal 800 bp fragment of the rat FAAH CDNA to evaluate the genomic copy number and tissue distribution of FAAH, respectively.

For the Southern blot, 10 Mg of rat genomic DNA was digested with the indicated restriction enzymes (100 units each) for 12 hours and then run on a 0.8% agarose gel. Rat genomic DNA was first isolated from rat liver as follows: approximately 500 mg of rat liver was shaken overnight at 55° C. in 2 ml of 100 mM Tris (pH 8.0), 0.2% SDS, 200 mM NaCl, and 0.2 mg/ml of proteinase K. The mixture was then spun at 15,000 rpm for 15 minutes and the supernatant was removed and treated with an equal volume of isopropanol. The precipitated genomic DNA was removed, partially dried, and resuspended in water by heating at 55° C. for 4 hours. 10 Mg of the DNA was digested with the indicated restriction enzymes (100 units each) for 12 hours, and then run on a 0.8% agarose gel. The DNA was then transferred under capillary pressure to a GeneScreenPlus hybridization transfer membrane (DuPont NEN) for use in Southern blot analysis. The blot was handled according to manufacturer's (Clontech) guidelines and subjected to the following post-hybridization washes: one 20 minute wash in a solution of 1% SDS and 0.2×SSC (30 mM NaCl, 3.0 mM sodium citrate, pH 7.0) at 25° C., followed by two 20 minute washes in a solution of 0.1% SDS and 0.2×SSC at 65° C. and one additional post-hybridization wash (0.1% SDS, 0.1×SSC, pH 7.0) at 65° C. for 1 hour. The blot was then exposed to X-ray film for 12 hours at −78° C.

Southern blot studies showed that the FAAH probe hybridized primarily to single DNA fragments using several different restriction digests of the rat genome (FIG. 12A). As expected, two hybridizing bands were observed in the HindIII digested DNA, as the FAAH probe contained an internal HindIII site. These results are most consistent with the FAAH gene being a single copy gene.

For Northern analyses, blots obtained from Clontech were handled according to manufacturer's guidelines, except that an additional post-hybridization wash with a solution of 0.1% SDS and 0.1×SSC (15 mM NaCl, 1.5 mM sodium citrate, pH 7.0) at 65° C. for 1 hour was conducted to ensure removal of nonspecific hybridization. The resulting blot was exposed to X-ray film for 6 hours at −78° C.

Northern blot analysis with the FAAH probe identified a single major mRNA transcript of approximately 2.5 kb in size that is most abundant in liver and brain, with lesser amounts present in spleen, lung, kidney, and testes (FIG. 12B). This transcript was not detectable in either heart or skeletal muscle, consistent with previously reported biochemical studies identifying no anandamide hydrolase activity in these two tissues (Deutsch et al, *Biochem. Pharmacol.*, 46:791–796, 1993). The Northern blot also contained low level hybridization of the FAAH cDNA probe to a few larger transcripts present only in those tissues expressing the 2.5 kb transcript as well. These transcripts may be either unprocessed or alternatively spliced forms of the 2.5 kb mRNA. In addition, the regional distribution of the rat FAAH transcript in the rat brain was examined by Northern analysis revealing highest level of the hippocampus and thalamus with lower levels of transcript detectable in other regions of the brain, including olfactory bulb, cortex, cerebellum and pituitary. Preliminary in situ hybridization analysis of rat brain slices has also identified high expression levels for rat FAAH in both hippocampus and hypothalamus. Lastly, Northern analysis of mouse FAAH expression levels at various stages in mouse embryonic development was performed where the mouse FAAH was first observed between days 11 and 15 with levels continuing to increase dramatically from day 15 to 17.

2. Cis-9,10-Octadecenoamidase cDNA Obtained from Mouse Liver MRNA

The mouse homolog of the rat cis-9,10-Octadecenoamidase cDNA was obtained from screening a mouse liver 5'-stretch plus cDNA library (Clontech) using the same conditions as described above for obtaining the rat cDNA with the one exception that the entire rat cDNA (FIG. 10-1 through 10-5) was used as the labeled probe.

The resultant mouse double-stranded 1959 bp cDNA homolog and encoded amino acid residue is shown in FIG. 13-1 through 13-4 with the ATG start site beginning at nucleotide position 7 indicated with the boxed methionine (M) residue. The stop codon, TGA, is similarly boxed as shown on FIG. 13-4 at nucleotide positions 1744 to 1746 followed by the 3' untranslated region. The top and bottom strands of the cDNA sequence are also respectively listed as SEQ ID Nos 39 and 41. The encoded amino acid sequence is shown in with the top strand in SEQ ID NO 39 and again by itself in SEQ ID NO 40.

3. Cis-9,10-Octadecenoamidase CDNA Obtained from Human Liver mRNA

A cDNA clone for the human homolog of cis-9,10-octadecenoamidase was similarly obtained as described above for the rat by screening a human liver 5' stretch plus cDNA library (Clontech) with the exception that the entire rat cDNA prepared above was used as the labeled probed and less stringent hybridization (25% instead of 50% formamide in the manufacturer's recommended hybridization buffer) was employed. Washing conditions also included 2×SSC containing 0.1% SDS at 500C instead of 1×SSC containing 0.1% SDS at 65° C.

The resultant human double-stranded 2045 bp cDNA homolog and encoded amino acid residue is shown in FIGS. 14-1 through 14-5 with the ATG start site beginning at nucleotide position 36 indicated with the boxed methionine (M) residue. The stop codon, TGA, is similarly boxed as shown on FIG. 14-4 at nucleotide positions 1773 to 1775 followed by the 3' untranslated region. The top and bottom strands of the cDNA sequence are also respectively listed as SEQ ID Nos 42 and 44. The encoded amino acid sequence is shown in with the top strand in SEQ ID NO 42 and again by itself in SEQ ID NO 43.

E. Preparation of Expressed Recombinant the Fatty Acid Amide Hydrolase Cis-9,10-Octadecenoamidase:

For preparing recombinant FAAH proteins for use in this invention, the rat, mouse and human cDNAs obtained above were separately cloned into the eukaryotic expression vector pcDNA3 for transient expression studies in COS-7 cells.

For preparing the rat, mouse and human FAAH recombinant protein, the corresponding FAAH cDNAs were excised from the Bluescript II vectors and separately ligated into the eukaryotic expression vector, pcDNA3 (Invitrogen, San Diego, Calif.). 100 mm dishes of COS-7 cells were grown at 37° C. to 70% confluency in complete medium (DMEM with L-glutamine, non-essential amino acids, sodium pyruvate and fetal bovine serum). The COS-7 cells were'then washed with serum-free medium and treated with 5 ml of transfection solution (5–6 μg of FAAH-pcDNA3 vector were preincubated with transfectamine (Gibco-BRL) for 30 minutes in 1 ml of serum free medium, then diluted to a final volume of 5 ml with serum free medium). The COS-7 cells were incubated at 37° C. for 5 hours, at which point 10 ml of complete medium was added to the cells and incubation was continued at 37° C. for 12 hours. The transfection solution was then aspirated away from the COS-7 cells, and the cells were incubated in a fresh batch of complete medium for another 24 hours. The COS-7 cells were harvested with a cell scraper, pelleted at low speed, washed twice with 1 mM NaHCO$_3$, and resuspended in 200 μl of 1 mM NaHCO$_3$. The resuspended COS-7 cells were dounce homogenized 12 times and 20 μl of the resulting cell extract was used to assay for oleamide hydrolase activity (assay is detailed above in Section B6) with the results as described below in Section F. Control COS-7 cells were prepared identically except that the pcDNA3 vector used for transfection contained the FAAH cDNA in reverse orientation.

The resultant expressed recombinant FAAH proteins for rat, human and mouse are then used as described below to assess specificity and enzymatic activity.

F. Fatty Acid Amide Hydrolase Specifificty and Activity of the Expressed Recombinant Fatty Acid Amide Hydrolases As described above, the transfected COS-7 cells were lysed to generate a cell extract for each of the recombinant expressed rat, mouse and human FAAH proteins of this invention.

Figure 16:
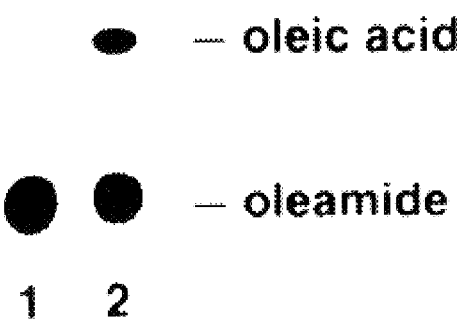
FIG. 16 shows the ability of human recombinant expressed FAAH to hydrolyze oleamide to oleic acid, as further described in FIG. 15A with thin layer chromatography and in Section F.

While untransfected COS-7 cells contained negligible amounts of oleamide hydrolase activity, COS-7 cells transfected with the rat FAAH cDNA expressed high levels of oleamide hydrolase activity (FIG. 15A). The assay was performed as described in Section B where by TLC the conversion of oleamide to oleic acid was assessed. As shown in FIG. 15A, COS-7 cells transiently tranfected with rat oleamide hydrolase cDNA in expression vector pcDNA 3 shown in lane 3 but not in untransfected COS-7 cells (lane 1) or control transfected cells (lane 2, transfected with pcDNA3 containing the oleamide hydrolase cDNA in reverse orientation), were effective at converting labeled oleamide to oleic acid. Similar results were obtained with COS-7 cells transiently transfected with human oleamide hydrolase as shown in FIG. 16 where the conversion to oleic acid is seen only in lane 2 as compared to control COS-7 cells in lane 1.

This enzyme activity, like the rat liver plasma membrane oleamide hydrolase activity, was inhibited by trifluoromethyl ketone as evidenced in FIG. 15B as shown in lane 2 of the figure the rat oleamide hydrolase-transfected COS-7 cells in the presence of 50 $\mu$M trifluoromethyl ketone as compared to the untreated extract in lane 1.

To confirm specificity of the expressed recombinant proteins, Western blot analyses with anti-FAAH polyclonal antibodies alone or in the presence of competing peptides were performed. Samples of cell extract from rat FAAH-transfected and untransfected COS-7 cells with approximately equal protein amounts were heated to 65° C. for 10 minutes in loading buffer with 2% SDS and 5% β-mercaptoethanol. The samples indicated above were then run on an 8–16% polyacrylamide gradient Tris-glycine gel, and transferred to nitrocellulose for Western blotting. The nitrocellulose blot was blocked with 5% Blotto in TBS-Tween overnight at 4° C., and then incubated with polyclonal antibodies generated against peptide 2 as previously described (15 $\mu$g/ml in TBS-Tween) generated against an internal FAAH peptide sequence for 2 hours at 25° C. The blot was then washed in TBS-Tween (0.1%), incubated with a secondary antibody-horseradish peroxidase conjugate for 30 minutes at 25° C., washed again in TBS-Tween, and developed with Stable Peroxide Solution and Luminol/Enhancer Solution (Pierce). Peptide competition experiments were conducted by preincubating 1000-fold molar excess of the peptide antigen corresponding to peptide 2 as previously described with polyclonal antibodies for 30 minutes prior to addition of antibodies to the blot.

Western blotting of the rat cDNA transfected COS-7 cell extract with polyclonal antibodies generated against the internal peptide 2 sequence of FAAH showed a 60–65 kDa immunoreactive band that comigrated with affinity-isolated FAAH on SDS-PAGE (FIG. 15C). Untransfected COS-7 cell extract contained no detectable immunoreactive protein band of this size. Additionally, the immunoreactivity of the 60–65 kDa protein was effectively competed away by pre-incubation of the antibodies with excess peptide antigen (FIG. 15C), while the trace quantities of cross reactive protein observed in both the transfected and untransfected COS-7 cell extracts were not competed by this peptide.

Previous work suggested that the enzyme activity that hydrolyzes oleamide may be the same activity that converts anandamide (arachidonyl ethanolamine) to arachidonic acid. Therefore, COS-7 cells transfected with the rat FAAH cDNA were assayed for anandamide hydrolase activity. To assess the enzymatic activity of the expressed recombinant fatty acid amide hydrolases of this invention on labeled anandamide, the following enzymatic assay was performed. $^{14}$C-anandamide was synthesized as follows: 12.5 $\mu$Ci (specific activity of 50 $\mu$Ci/AM) of $^{14}$C arachidonic acid (Moravek Biochemicals) was dissolved in 100 $\mu$l $CH_2Cl_2$, cooled to 0° C., and treated with excess oxalyl chloride. The reaction mixture was stirred at 25° C. for 6 hours, after which time the solvent was evaporated. The remaining residue was cooled to 0° C., treated with a large excess of ethanolamine, and stirred at 25° C. for 15 minutes. The reaction mixture was then partitioned between ethyl acetate and 2 M HCl, and the organic layer was washed with water and then evaporated to dryness. The resulting $^{14}$C-anandamide was diluted with unlabeled anandamide to a final specific activity of 5 $\mu$Ci/$\mu$M in ethanol. Approximately 1 $\mu$Ci of $^{14}$C-anandamide and 20 $\mu$l of dounce homogenized COS-7 cell extract were used for each anandamide hydrolase assay as detailed above for the oleamide hydrolase assays. Briefly, FAAH hydrolysis assays were conducted in triplicate with 100 $\mu$M substrate, 35 $\mu$g of rat transfected COS-7 cell protein for 5 minutes at 37° C. (except in the case of stearic amide, where due to low solubility, 20 $\mu$M substrate comparison to oleamide were conducted). Products were separated on TLC as described previously, scraped into scintillation fluid, and radioactivity was quantitated by scintillation counting. Substrate hydrolysis in the presence of equal amounts of untransfected COS-7 cell protein extract served as background control in all cases and was substracted from FAAH hydrolysis rates to give the data as presented below.

Figure 17:
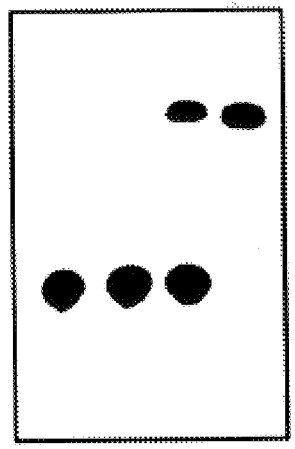
FIG. 17 shows the results of thin layer chromatography demonstrating the conversion of labeled anandamide to arachidonic acid in rat FAAH-transfected COS-7 cells as shown in lane 3 but not in control untransfected cells (lane 2). TLC standards of anandamide and arachidonic acid are shown in lanes 1 and 4, respectively.

The results of the anandamide assays showed that while untransfected COS-7 cells contained negligible quantities of anandamide hydrolase activity, transfected COS-7 cells produced high levels of anandamide hydrolase activity (FIG. 17). Thus, FAAH has the capacity to hydrolyze both oleamide and anandamide, indicating that the amidase may act as a general degradative enzyme for the fatty acid amide family of signaling molecules. The substrate promiscuity of FAAH is reminiscent of the monoamine oxidase enzymes which serve to oxidize a variety of amine-containing neurotransmitters.

To further assess the substrate specificity spectrum of enyzmatic hydolytic activity of the recombinant expressed proteins of this invention, other $^{14}$C-labeled fatty acid amides were synthesized as described in Section B6 and above for $^{14}$C-oleamide, with the exception of anandamide as described.

The results showed that while recombinant expressed rat FAAH catalyzes the hydrolysis of oleamide and anandamide at approximately equal rates, FAAH does discriminate among fatty acid amides, as FAAH hydroylzes other representative fatty acid amides, including myristic amide, palmitic amide and stearic amide at a significantly reduced rate as compared to that seen with oleamide or anandamide as shown in Table 1 below. Where indicated in the table the anandamide and oleamide hydrolysis rates are considered to be 100% of FAAH activity to which other fatty acid amide hydrolysis rates are compared.

TABLE 1

| Substrate | Rate of Hydrolysis* | % |
|---|---|---|
| Anandamide (100 μM) | 333 +/- 30 | 100 |
| Oleamide (100 μM) | 242 +/- 20 | 72.6 |
| Myristic Amide (100 μM) | 81 +/- 7 | 24.3 |
| Palmitic Amide (100 μM) | 33 +/- 2 | 9.9 |
| Oleamide (20 μM) | 41 +/- 2 | 100 |
| Stearic Amide (20 μM) | 2.3 +/- 1 | 5.8 |

* Rate is measured in nmol/min/mg for each

Comparable assays are performed with the mouse and human recombinant homologs to the rat enzyme as used above.

Thus, as shown above, the rat FAAH enzyme was not without substrate preference, albeit it did exhibit activity against a number of amide substrates. The degree to which FAAH showed substrate selectivity is best exemplified by the nearly twenty fold rate difference between the enzyme's hydrolysis of oleamide and steric amide, two compounds that only differ by a single degree of unsaturation at the Δ9 position. This pattern was also confirmed with assays with the inhibitor trifluoromethyl ketone that was a twenty fold stronger inhibitor of FAAH than for the corresponding trifluoromethyl ketone analog of stearic amide. Thus, FAAH significantly favors the bent alkyl chain of oleamide over the straight alkyl chain of stearic amide.

A deletion mutant for generating a soluble form of the FAAH molecules of this invention was also prepared. A construct was created in which the putative transmembrane domain was deleted resulting in a truncated FAAH beginning at amino acid residue 30 of the encoded protein rather than 1. To prepare this construct, the following primers were designed for PCR amplification of the 5' end of rat FAAH cDNA lacking the first 140 bp encoding the amino terminal 30 amino acids of FAAH. The 5' and 3' primers had the respective nucleotide sequences 5'GCGGTACCATGC-GATGGACCGGGCGC3' (SEQ ID NO 45) encoding amino acids 30–35 and containing a KpnI site and an artificial stop codon and 5'GGTCTGGCCAAAGAGAGG3' (SEQ ID NO 46) where its reverse complement encodes amino acids 199–204.

The amplified transmembrane deleted rat FAAH cDNA fragment was then digested with the appropriate restriction enzymes (KpnI and HindIII) and cloned into the similarly digested FAAH-pBluescript vector replacing the original cDNA 5' end. The deleted construct was confirmed by sequencing and then excised and transferred to pcDNA3 for expression studies as described herein.

For expression, the transfected COS-7 cell extract was separated into soluble and membrane fractions as follows: the extract was spun at 2500 rpm for 5 minutes at 25° C. and the supernatant was transferred to an airfuge tube and spun in an ultracentrifuge (30 psi for 40 minutes at 4° C.) for preparing soluble supernatant. The pellet contained the membrane bound fraction that was then resuspended in a volume of 1 mM $NaHCO_3$ equal to the volume of the supernatant.

The transmembrane-deleted expressed recombinant FAAH was functional in COS-7 cell expression assays as described above. The mouse and human transmembrane truncation homologs of the rat cDNA are similarly prepared and used in practicing this invention.

Given the increasing number of studies demonstrating biological activities for various members of the fatty acid amide family of signaling molecules, the discovery of a family of fatty acid amide hydrolases (FAAH) having homology between rat, mouse and human as described herein provides a valuable invention for ongoing studies dedicated to understanding the regulation, mechanism, and pharmacology of the metabolic process that inactivates the fatty acid amides. In addition, the cloned FAAH gene in conjunction with potent FAAH inhibitors provides the ability in both elucidating the physiological pathways affected by the fatty acid amide family and developing systematic approaches towards the pharmacological intervention of these biological processes.

What is claimed is:

1. An isolated and purified polypeptide that has the amino acid residue sequence shown in SEQ ID NO 36.

2. The polypeptide of claim 1 that hydrolyzes myristic amide, palmitic amide and stearic amide.

3. An isolated and purified polypeptide that has the amino acid residue sequence shown in SEQ ID NO 40.

4. The polypeptide of claim 3 that hydrolyzes myristic amide, palmitic amide and stearic amide.

5. An isolated and purified polypeptide that has the amino acid residue sequence shown in SEQ ID NO 43.

6. The polypeptide of claim 5 that hydrolyzes myristic amide, palmitic amide and stearic amide.

* * * * *